United States Patent
Asano et al.

(10) Patent No.: US 12,202,908 B2
(45) Date of Patent: *Jan. 21, 2025

(54) COMPLEX HAVING ANTI-HUMAN MUC1 ANTIBODY FAB FRAGMENT, PEPTIDE LINKER AND/OR LIGAND

(71) Applicant: Astellas Pharma Inc., Chuo-ku (JP)

(72) Inventors: Toru Asano, Tokyo (JP); Yorikata Sano, Tokyo (JP); Akifumi Morinaka, Tokyo (JP); Hiroki Shirai, Tokyo (JP); Kazunori Hirayama, Tokyo (JP); Michinori Akaiwa, Tokyo (JP); Hiroyoshi Yamada, Tokyo (JP); Nobuyuki Shiraishi, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 1101 days.

This patent is subject to a terminal disclaimer.

(21) Appl. No.: 17/055,799

(22) PCT Filed: May 17, 2019

(86) PCT No.: PCT/JP2019/019663
§ 371 (c)(1),
(2) Date: Jun. 21, 2021

(87) PCT Pub. No.: WO2019/221269
PCT Pub. Date: Nov. 21, 2019

(65) Prior Publication Data
US 2021/0340276 A1    Nov. 4, 2021

(30) Foreign Application Priority Data
May 17, 2018    (JP) .................. 2018-095461

(51) Int. Cl.
*C07K 16/30* (2006.01)
*A61K 47/54* (2017.01)
*A61K 47/65* (2017.01)
*A61K 51/04* (2006.01)
*A61K 51/10* (2006.01)

(52) U.S. Cl.
CPC .......... *C07K 16/3092* (2013.01); *A61K 47/54* (2017.08); *A61K 47/65* (2017.08); *A61K 51/0482* (2013.01); *A61K 51/1045* (2013.01); *A61K 51/1093* (2013.01); *C07K 2317/55* (2013.01)

(58) Field of Classification Search
CPC .......... C07K 16/3092; C07K 2317/55; C07K 19/00; A61K 47/54; A61K 47/65; A61K 51/0482; A61K 51/1045; A61K 51/1093; A61K 47/6851; A61K 2039/505; A61P 35/00

See application file for complete search history.

(56) References Cited

U.S. PATENT DOCUMENTS

| | | | |
|---|---|---|---|
| 8,623,367 B2 | 1/2014 | Momm et al. | |
| 10,517,966 B2* | 12/2019 | Morinaka | C12N 15/85 |
| 11,679,166 B2* | 6/2023 | Morinaka | A61K 49/0032 |
| | | | 424/1.49 |
| 2002/0146750 A1 | 10/2002 | Hoogenboom et al. | |
| 2005/0118167 A1 | 6/2005 | Okada et al. | |
| 2005/0244333 A1 | 11/2005 | Yazaki et al. | |
| 2007/0031402 A1 | 2/2007 | Zhang et al. | |
| 2007/0086979 A1 | 4/2007 | Chevrier et al. | |
| 2008/0069816 A1 | 3/2008 | Yazaki et al. | |
| 2009/0081213 A1 | 3/2009 | Chevrier et al. | |
| 2009/0081231 A1 | 3/2009 | Chevrier et al. | |
| 2012/0040375 A1 | 2/2012 | Nishimura et al. | |
| 2012/0128676 A1 | 5/2012 | Goletz et al. | |
| 2012/0251529 A1 | 10/2012 | Hofer et al. | |
| 2012/0328514 A1 | 12/2012 | Cesati et al. | |
| 2013/0045543 A1 | 2/2013 | Nishimura et al. | |
| 2013/0123471 A1 | 5/2013 | Yang et al. | |
| 2013/0202626 A1 | 8/2013 | Linke et al. | |
| 2014/0212408 A1 | 7/2014 | Hofer et al. | |
| 2015/0005474 A1 | 1/2015 | Goletz et al. | |
| 2015/0056134 A1 | 2/2015 | Sawada et al. | |
| 2015/0078997 A1 | 3/2015 | Cesati et al. | |
| 2015/0165067 A1 | 6/2015 | Balderes et al. | |
| 2016/0011217 A1 | 1/2016 | Matsumura et al. | |

(Continued)

FOREIGN PATENT DOCUMENTS

| | | |
|---|---|---|
| CA | 3 115 747 A1 | 4/2020 |
| CN | 102482701 B | 5/2015 |

(Continued)

OTHER PUBLICATIONS

Alirezapour et al. Development of [64Cu]-DOTA-PR81 radioimmunoconjugate for MUC-1 positive PET imaging. 2016. Nuclear Medicine and Biology. 43: 73-80. (Year: 2016).*

English translation of JP6164556B2 downloaded from patentscope Apr. 17, 2024. (Year: 2017).*

Uehara et al. (67/68)Ga-labeling agent that liberates (67/68)Ga-NOTA-methionine by lysosomal proteolysis of parental low molecular weight polypeptides to reduce renal radioactivity levels. Bioconjug Chem. Nov. 19, 2014;25(11):2038-45. (Year: 2014).*

(Continued)

*Primary Examiner* — Brad Duffy
*Assistant Examiner* — Amber K Faust
(74) *Attorney, Agent, or Firm* — Oblon, McClelland, Maier & Neustadt, L.L.P.

(57) ABSTRACT

Provided are a conjugate comprising an anti-human MUC1 antibody Fab fragment and a peptide linker and/or a ligand, a composition for diagnosis and/or a pharmaceutical composition comprising the conjugate, a method for diagnosing and/or treating a cancer using the conjugate, and the like. In the conjugate used, the anti-human MUC1 antibody Fab fragment is bound to the ligand via the peptide linker or the like.

25 Claims, 1 Drawing Sheet

Specification includes a Sequence Listing.

(56) References Cited

U.S. PATENT DOCUMENTS

| | | |
|---|---|---|
| 2016/0075777 A1 | 3/2016 | Carayon et al. |
| 2016/0108131 A1 | 4/2016 | Berne et al. |
| 2016/0130337 A1 | 5/2016 | Gekkieva et al. |
| 2016/0229923 A1 | 8/2016 | Hofer et al. |
| 2016/0340420 A1 | 11/2016 | Zhang et al. |
| 2017/0028062 A1 | 2/2017 | Amsberry et al. |
| 2017/0145100 A1 | 5/2017 | Linke et al. |
| 2017/0198056 A1 | 7/2017 | Nishimura et al. |
| 2018/0022817 A1 | 1/2018 | Berne et al. |
| 2018/0079827 A1 | 3/2018 | Hofer et al. |
| 2018/0221512 A1 | 8/2018 | Yazaki et al. |
| 2018/0298092 A1 | 10/2018 | Gekkieva et al. |
| 2018/0371094 A1 | 12/2018 | Linke et al. |
| 2019/0091353 A1 | 3/2019 | Arano et al. |
| 2019/0185583 A1 | 6/2019 | Hofer et al. |
| 2019/0269804 A1 | 9/2019 | Morinaka et al. |
| 2019/0381172 A1 | 12/2019 | Amsberry et al. |
| 2020/0102401 A1 | 4/2020 | Berne et al. |
| 2020/0123270 A1 | 4/2020 | Doihara et al. |
| 2020/0231680 A1 | 7/2020 | Linke et al. |
| 2020/0268913 A1 | 8/2020 | Arano et al. |
| 2020/0270336 A1 | 8/2020 | Zhang et al. |
| 2021/0340242 A1 | 11/2021 | Gekkieva et al. |
| 2021/0395370 A1 | 12/2021 | Linke et al. |

FOREIGN PATENT DOCUMENTS

| | | | |
|---|---|---|---|
| EP | 2 351 777 A1 | 8/2011 | |
| EP | 2 567 982 A1 | 3/2013 | |
| EP | 3 543 337 A1 | 9/2019 | |
| EP | 3 795 590 A1 | 3/2021 | |
| EP | 3 865 154 A1 | 8/2021 | |
| EP | 3 909 606 A1 | 11/2021 | |
| EP | 3 909 608 A1 | 11/2021 | |
| JP | 2010-505775 A | 2/2010 | |
| JP | 2012-511540 A | 5/2012 | |
| JP | 2012-532868 A | 12/2012 | |
| JP | 2013-500703 A | 1/2013 | |
| JP | 2013-505702 A | 2/2013 | |
| JP | 2013-510093 A | 3/2013 | |
| JP | 2013-517487 A | 5/2013 | |
| JP | 2016-506370 A | 3/2016 | |
| JP | 2016-534735 A | 11/2016 | |
| JP | 6164556 B2 * | 7/2017 | ......... A61K 51/1093 |
| WO | WO 00/66160 A1 | 11/2000 | |
| WO | WO 01/75110 A2 | 10/2001 | |
| WO | WO 2005/086875 A2 | 9/2005 | |
| WO | WO 2007/019232 A2 | 2/2007 | |
| WO | WO 2007/019232 A3 | 2/2007 | |
| WO | WO 2008/040362 A2 | 4/2008 | |
| WO | WO 2010/050528 A1 | 5/2010 | |
| WO | WO 2010/066762 A1 | 6/2010 | |
| WO | WO 2011/005322 A2 | 1/2011 | |
| WO | WO 2011/012309 A1 | 2/2011 | |
| WO | WO 2011/056983 A1 | 5/2011 | |
| WO | WO 2011/135869 A1 | 11/2011 | |
| WO | WO 2012/015912 A1 | 2/2012 | |
| WO | WO 2012/117002 A1 | 9/2012 | |
| WO | WO 2013/081091 A1 | 6/2013 | |
| WO | WO 2014/079886 A1 | 5/2014 | |
| WO | WO 2014/133093 A1 | 9/2014 | |
| WO | WO 2014/177568 A1 | 11/2014 | |
| WO | WO 2015/053871 A2 | 4/2015 | |
| WO | WO 2015/094900 A1 | 6/2015 | |
| WO | WO 2015/157286 A1 | 10/2015 | |
| WO | WO 2015/166934 A1 | 11/2015 | |
| WO | WO 2016/073915 A1 | 5/2016 | |
| WO | WO 2016/130726 A1 | 8/2016 | |
| WO | WO 2017/150549 A1 | 9/2017 | |
| WO | WO 2018/092885 A1 | 5/2018 | |
| WO | WO 2019/009388 A1 | 1/2019 | |
| WO | WO 2019/065774 A1 | 4/2019 | |
| WO | WO 2019/221269 A1 | 11/2019 | |
| WO | WO 2020/075746 A1 | 4/2020 | |
| WO | WO 2020/145227 A1 | 7/2020 | |

OTHER PUBLICATIONS

Combined Russian Office Action and Search Report issued Jan. 13, 2023, in corresponding Russian Patent Application No. 2021112023/10(025710) (with English Translation), 18 pages.

Wang W. et al., "Antibody Structure, Instability, and Formulation", Journal of pharmaceutical sciences, 2007, v .96, No. 1, pp. 1-26, DOI: 10.1002/JPS.207270.

Wang, W., "Instability, stabilization, and formulation of liquid protein pharmaceuticals", International Journal of Pharmaceutics, 1999, 185(2), p. 129-188, doi: S10.1016=0378-5173 (99)00152-0).

Jorgensen, L., et al. "Recent trends in stabilising peptides and proteins in pharmaceutical formulation—considerations in the choice of excipients", Expert Opinion on Drug Delivery, 2009, v.6, 11, p. 1219-1230, doi:10.1517/17425240903199143.

Office Action issued Aug. 11, 2023, in corresponding Russian Patent Application No. 2020141476 (with English Translation), 16 pages.

Weineisen et al., "Synthesis and preclinical evaluation of DOTAGA-conjugated PSMA ligands for functional imaging and endoradiotherapy of prostate cancer", EJNMMI Research, 2014, vol. 4:63, pp. 1-15.

Zeglis et al., "The Bioconjugation and Radiosynthesis of $^{89}$Zr-DFO-labeled Antibodies", Journal of Visualized Experiments, 2015, vol. 96, e52521, pp. 1-8.

Moon et al., "Deferoxamine inhibits TRAIL-mediated apoptosis via regulation of autophagy in human colon cancer cells", Oncology Reports, 2015, vol. 33, pp. 1171-1176.

Parmiani et al., "Unique Human Tumor Antigens: Immunobiology and Use in Clinical Trials", J. Immunol., 2007, vol. 178 (4): pp. 1975-1979.

Extended European Search Report issued Oct. 7, 2022 in European Patent Application No. 19870506.3, 14 pages.

Gaozhong Zhu, et al., "Formulation and protein- and peptide-based parenteral products," Parental Medications Third Edition, XP055874783, 2010, 34 pages.

Steven Shire, "Formulation of proteins and monoclonal antibodies (mAbs)," Monoclonal Antibodies, XP009192951, 2015, pp. 93-120.

Combined Taiwanese Office Action and Search Report issued May 27, 2022 in Patent Application No. 107123231 (with English language translation), 12 pages.

Combined Russian Office Action and Search Report issued Nov. 25, 2022 in Russian Patent Application No. 2020141476/10 (with English translation), 20 pages.

Nakada et al., "Novel antibody drug conjugates containing exatecan derivative-based cytotoxic payloads", Bioorganic & Medicinal Chemistry Letters, 2016, vol. 26, pp. 1542-1545.

Lu et al., "Linkers Having a Crucial Role in Antibody-Drug Conjugates", International Journal of Molecular Sciences, 2016, vol. 17, pp. 1-22.

Ambrosini et al., "$^{68}$Ga-DOTA-peptides in the Diagnosis of NET", PET Clin., 2014, vol. 9, pp. 37-42.

U.S. Appl. No. 16/681,306, filed Nov. 12, 2019, US 2020/0261603 A1, Akifumi Morinaka, et al.

Extended European Search Report issued Apr. 5, 2022 in European Patent Application No. 19804452.1, 14 pages.

Juan C. Almagro, et al., "Humanization of Antibodies" Frontiers in Bioscience, XP009126790, vol. 13, Jan. 1, 2008, pp. 1619-1633.

David V. Gold, et al., "Combined 90Yttrium-DOTA-Labeled PAM4 Antibody Radioimmunotherapy and Gemcitabine Radiosensitization for the Treatment of a Human Pancreatic Cancer Xenograft" International Journal of Cancer, XP071282184, vol. 109, Jan. 14, 2004, pp. 618-626.

International Search Report issued Sep. 18, 2018 in PCT/JP2018/025618 (submitting English translation only), 2 pages.

Extended European Search Report issued Feb. 22, 2021 in European Patent Application No. 18827622.4, 11 pages.

International Search Report issued Dec. 24, 2019 in PCT/JP2019/039793 (submitting English translation only), 2 pages.

Paul J. Yazaki, et al., "Humanization of the Anti-CEA T84.66 Antibody Based on Crystal Structure Data" Protein Engineering Design & Selection, vol. 17, No. 5, 2004, pp. 481-489.

Takashi Kamigaki, et al., "Improved Tumor Detection by Anti-CEA Chimeric Fab Oligomers with Disulfide Linkages in a Pancreatic-Carcinoma-Xenograft Model" International Journal of Cancer, vol. 66, No. 2, Apr. 10, 1996, pp. 261-267.

(56) References Cited

OTHER PUBLICATIONS

Stefanie Nittka et al., "Radioimmunoimaging of Liver Metastases with PET Using a $^{64}$Cu-Labeled CEA Antibody in Transgenic Mice" PLOS ONE, vol. 9, No. 9, Apr. 17, 2014, pp. 1-8.

Imabori, Kazutomo, et al., "HEPES" Biochemical Dictionary, 3rd edition, Tokyo Kagaku Dojin K. Jul. 1, 2002, p. 1267.

Susumu Uchiyama, et al., "Solution Properties of Antibody Pharmaceuticals" Journal of Pharmaceutical Science and Technology, Japan, vol. 74, No. 1, Jan. 2014, pp. 12-18.

Susumu Uchiyama, et al., "(1) Relationship between composition and stability of protein solution" "Analytical Tips for Biopharmaceutics: Foundation and Application for Quality Assessment, Part 6th: Properties of Protein Solution" Pharm Tech Japan, vol. 34, No. 1, Jan. 2018, pp. 109-120.

Tsutomu Arakawa, "How do Additives Stabilize Proteins in Freezing Operations, Protein, Nucleic Acid and Enzyme" Protein Biophysics, Amgen, Thousand Oaks, vol. 37, No. 9, Jul. 1, 1992, pp. 1517-1523.

Floor C. J. Van De Watering, et al., "Zirconium-89 Labeled Antibodies: a New Tool for Molecular Imaging in Cancer Patients" BioMed Research International, 2014, vol. 2014, Article ID 203601, 13 pages.

Lars R. Perk, et al., "p-Isothiocyanatobenzyl-Desferrioxamine: a New Bifunctional Chelate for Facile Radiolabeling of Monoclonal Antibodies with Zirconium-89 for Immuno-PET Imaging" European Journal of Nuclear Medicine and Molecular Imaging, vol. 37, No. 2, 2010, pp. 250-259.

Lin Li, et al., "A Versatile Bifunctional Chelate for Radiolabeling Humanized Anti-CEA Antibody with In-111 and Cu-64 at Either Thiol or Amino Groups: PET Imaging of CEA-Positive Tumors with Whole Antibodies" Bioconjugate Chem., vol. 19, No. 1, 2008, pp. 89-96.

Kevin Hughes, et al., Use of Carcinoembryonic Antigen Radioimmunodetection and Computed Tomography for Predicting the Resectability of Recurrent Colorectal Cancer Annals of Surgery, vol. 226, No. 5, 1997, pp. 621-631.

Petra Willkomm, et al., "FDG PET and Immunoscintigraphy with $^{99m}$Tc-Labeled Antibody Fragments for Detection of the Recurrence of Colorectal Carcinoma" The Journal of Nuclear Medicine, vol. 41, No. 10, Oct. 2000, pp. 1657-1663.

Kenneth T. Cheng, "$^{99m}$Tc-Arcitumomab", [online], Update: Mar. 17, 2008., Molecular Imaging and Contrast Agent Database, [searched on May 17, 2017], internet URL:https://www.ncbi.nlm.nih.gov/books/NBK23676/, 6 pages.

"CEA-SCAN® For the Preparation of Technetium Tc 99m Arcitumomab. Sterile, Non-Pyrogenic, Lyophilized Powder for Intravenous Use Only" package insert URL https://pharmacyce.unm.edu/nuclear_program/neolibrary/libraryfiles/package_inserts/cea-scan.pdf, 11 pages.

Eben L. Rosenthal, et al., "Sensitivity and Specificity of Cetuximab-IRDye800CW to Identify Regional Metastatic Disease in Head and Neck Cancer" Clinical Cancer Research, vol. 23, No. 16, Aug. 15, 2017, pp. 4744-4752.

Search Report and Written Opinion issued Oct. 17, 2022, in corresponding Singapore Application No. 11202103670X, 11 pages.

Van Brummelen et al., "$^{89}$Zr-labeled CEA-targeted IL-2 variant immunocytokine in patients with solid tumors: CEA-mediated tumor accumulation and role of IL-2 receptor-binding", Oncotarget, vol. 9, No. 37, May 15, 2018, pp. 24737-24749.

Russian Federation Office Action issued Aug. 20, 2021 in Russian Federation Patent Application No. 2019118653/10(035813) (with English translation), 7 pages.

Yarilin, A. A. "Fundamentals of Immunology: Textbook" M.: Medicine, 1999, 608s, pp. 171-173.

Opposition issued Dec. 15, 2021 in corresponding Colombian Patent Application No. NC2021/0010115 (with English Translation), 32 pages.

International Search Report issued Mar. 24, 2020 in PCT/JP2020/000036 (submitting English translation only), 3 pages.

International Search Report issued Apr. 7, 2020 in PCT/JP2020/000037 (submitting English translation only), 3 pages.

Tomoya Uehara, et al., "A Gallium-67/68-Labeled Antibody Fragment for Immuno-SPECT/PET Shows Low Renal Radioactivity Without Loss of Tumor Uptake" Clinical Cancer Research, vol. 24, No. 14, Jul. 15, 2018, pp. 3309-3316.

M. Araki et al., "27PA-am401" Abstract of the 138th Annual Meeting of the Pharmaceutical Societ of Japan, vol. 138, 2018, 1 page.

Giuseppe Giannini, et al., Synthesis and Preliminary in Vitro Evaluation of DOTA-Tenatumomab Conjugates for Theranostic Applications in Tenascin Expressing Tumors Bioorganic & Medicinal Chemical, vol. 27, 2019, pp. 3248-3253.

"Study to Evaluate the Safety and Preliminary Efficacy of 177 Lu-OPS201 in NETs" ClinicalTrials.gov Identifier: NCT02592707, Oct. 30, 2015, 8 pages.

Patrice Chevallier, et al., "BCR-ABL1 Molecular Remission After $^{90}$Y-epratuzumab Tetraxetan Radioimmunotherapy in CD22$^+$ Ph$^+$ B-ALL: Proof of Principle" European Journal of Hematology, vol. 91, vol. 6, 2013, pp. 552-556.

S.W. Tsai, et al., "Metabolism and Renal Clearance of $^{111}$In-Labeled DOTA-Conjugated Antibody Fragments" Bioconjugate Chem, vol. 12, No. 2, 2001, pp. 264-270.

Lin Li, et al., "Reduction of Kidney Uptake in Radiomental Labeled Peptide Linkers Conjugated to Recombinant Antibody Fragments. Site-Specific Conjugation of DOTA-Peptides to a Cys-Diabody" Bioconjugate Chem., vol. 13, No. 5, 2002, pp. 985-995.

Hiromichi Akizawa, et al., "Renal Brush Border Enzyme-Cleavable Linkages for Low Renal Radioactivity Levels of Radiolabeled Antibody Fragments" Bioconjugate Chemisthry, vol. 24, 2013, pp. 291-299.

Yasushi Arano, et al., "Chemical Design of Radiolabeled Antibody Fragments for Low Renal Radioactivity Levels" Cancer Research, vol. 59, Jan. 1, 1999, pp. 128-134.

Tomoya Uehara, et al., "Design, Synthesis, and Evaluation of [$^{188}$Re]Organorhenium-Labeled Antibody Fragments with Renal Enzyme-Cleavable Linkage for Low Renal Radioactivity Levels" Bioconjugate Chem., vol. 18, No. 1, 2007, pp. 190-198.

Tomoya Uehara, et al., "$^{67/68}$Ga-Labeling Agent That Liberates $^{67/68}$Ga-NOTA-Methionine by Lysosomal Proteolysis of Parental Low Molecular Weight Polypeptides to Reduce Renal Radioactivity Levels" Bioconjugate Chem., vol. 25, 2014, pp. 2038-2045.

Chuanchu Wu, et al., "Biodistribution and Catabolismof Ga-67-Labeled Anti-Tac dsFv Fragment" Bioconjugate Chem, vol. 8, 1997, pp. 365-369.

Extended European Search Report issued Jul. 6, 2020 in European Patent Application No. 17870672.7, 7 pages.

Kiyoshi, M., et al., "Affinity Improvement of a Therapeutic Antibody by Structure-Based Computational Design: Generation of Electrostatic Interactions in the Transition State Stabilizes the Antibody-Antigen Complex", PLOS One, Jan. 2014, vol. 9, issue 1, XP055213871, pp. 1-9.

Shirai, H., et al., "High-resolution modeling of antibody structures by a combination of bioinformatics, expert knowledge, and molecular simulations", Proteins: Structure, Function, and Bioinformatics, vol. 82, No. 8, May 13, 2014, XP055394189, pp. 1624-1635.

International Search Report issued Feb. 13, 2018 in PCT/JP2017/041486 filed Nov. 17, 2017, pages.

International Search Report issued on Aug. 13, 2019 in PCT/JP2019/019663 filed on May 17, 2019, 3 pages.

Lavrsen, K. et al., "Aberrantly glycosylated MUC1 is expressed on the surface of breast cancer cells and a target for antibody-dependent cell-mediated cytotoxicity," Glycoconj J, vol. 30, 2013, pp. 227-236.

Danielczyk, A. et al., "PankoMab: a potent new generation anti-tumour MUC1 antibody," Cancer Immunol Immunother, vol. 55, 2006, pp. 1337-1347.

Akizawa, H. et al., "Renal uptake and metabolism of radiopharmaceuticals derived from peptides and proteins," Advanced Drug Delivery Reviews, vol. 60, 2008, pp. 1319-1328.

\* cited by examiner

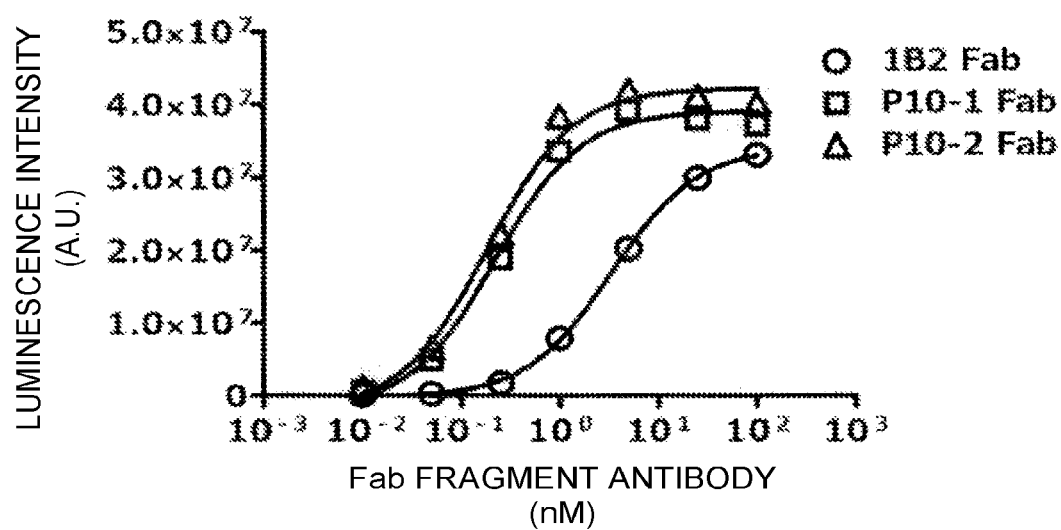
| ANTIBODY NAME | 1B2 Fab | P10-1 Fab | P10-2 Fab |
|---|---|---|---|
| Kd (nM) | 3.19 | 0.35 | 0.29 |
| <95% CI> | <2.89-3.51> | <0.19-0.63> | <0.15-0.56> |

COMPLEX HAVING ANTI-HUMAN MUC1 ANTIBODY FAB FRAGMENT, PEPTIDE LINKER AND/OR LIGAND

TECHNICAL FIELD

The present invention relates to a conjugate comprising an anti-human MUC1 antibody Fab fragment and a peptide linker and/or a ligand. The present invention also relates to a composition for diagnosis and/or a pharmaceutical composition comprising the conjugate, and a method for diagnosing and/or treating a cancer using the conjugate.

BACKGROUND ART

Mucin 1 (MUC1) is a membrane-bound glycoprotein that is expressed on the lumen side of epithelial cells constituting the epithelial tissues of the mammary gland, the trachea and the gastrointestinal tract, etc. (Nat. Rev. Cancer, 2004 January; 4 (1): 45-60). MUC1 is overexpressed in cancer cells of breast cancer (Mod. Pathol., 2005 October; 18 (10): 1295-304), lung cancer (Hum. Pathol., 2008 January; 39 (1): 126-36), colorectal cancer (Int. J. Oncol., 2000 January; 16 (1): 55-64), bladder cancer (PLoS One, 2014 March; 9 (3): e92742), skin cancer (Histopathology, 2000 September; 37 (3): 218-23), thyroid gland cancer (J. Pathol., 2003 July; 200 (3): 357-69), stomach cancer (J. Pathol., 2000 March; 190 (4): 437-43), pancreatic cancer (Int. J. Oncol., 2004 January; 24 (1): 107-13), kidney cancer (Mod. Pathol., 2004 February; 17 (2): 180-8), ovary cancer (Gynecol. Oncol., 2007 June; 105 (3): 695-702) and uterine cervical cancer (Am. J. Clin. Pathol., 2004 July; 122 (1): 61-9), etc. MUC1 is useful as a target molecule for detecting a cancer lesion (Nat. Rev. Cancer, 2004 January; 4 (1): 45-60; and Pathol. Res. Pract., 2010 Aug. 15; 206 (8): 585-9).

MUC1 undergoes the O-glycosylation of threonine at position 9 of a 20-amino acid tandem repeat sequence HGVTSAPDTRPAPGSTAPPA (SEQ ID NO: 15) present in an extracellular domain. In cancer cells, this O-glycosylation is incomplete, and O-glycosylation such as T(Galβ1-3GalNAcα1-O-Ser/Thr), Tn(GalNAcα1-O-Ser/Thr) and 2,3ST(Neu5Acα2-3Galβ1-3GalNAcα-O-Ser/Thr) is known to occur in a cancer-specific manner (PTL 1 and NPL 1). Since MUC1 in normal tissues does not undergo such cancer-specific O-glycosylation, human cancer-specific MUC1 is particularly useful as a target molecule for treating various cancers in humans. For example, a 1B2 antibody (PTL 1), a PankoMab antibody (NPL 2), and a 5E5 antibody (PTL 2) are known as antibodies against such human cancer-specific MUC1. Among these antibodies, the 1B2 antibody has been reported to have high specificity for human cancer-specific MUC1 as compared with the PankoMab antibody (PTL 1).

There are also great needs for the visualization or early detection of cancer lesion. Further, there are also the needs for the differentiation between a cancer lesion and a benign lesion. From such needs, it is also useful to visualize cancer lesion by molecular imaging techniques such as γ-ray imaging (PET and SPECT) using an antibody specifically binding to human cancer-specific MUC1 as an in vivo diagnostic drug. Furthermore, antibody drugs containing an antibody conjugated with a cancer therapeutic drug have also received attention.

Meanwhile, in general, antibodies have a long half-life in blood and require a period as long as 4 days to 5 days for reaching a tumor-to-blood ratio that confers a signal-to-background ratio sufficient for visualizing a cancer, after administration into the body (Clin. Pharmacol. Ther., 2010 May; 87 (5): 586-92). Also, the Fc regions of antibodies cause a pharmacological effect such as antibody-dependent cellular cytotoxicity (ADCC) or complement-dependent cytotoxicity (CDC) (NPL 1; and Curr. Opin. Biotechnol., 2002 December; 13 (6): 609-14). Furthermore, antibodies highly accumulate in the liver regardless of a target, and cancer cells such as breast cancer are highly to metastasize to the liver. The accumulation in the liver interfere with the detection of hepatic metastasis at the time of diagnosis of systemic cancer foci due to distant metastasis (Clin. Pharmacol. Ther., 2010 May; 87 (5): 586-92).

By contrast, low-molecular antibody fragments such as Fab, scFv, diabody, and minibody are expected to be utilized as therapeutic antibodies because of easy reaching to foci with their high tissue penetration and low cost production by using an expression system in E. coli or yeast. Also, in general, antibody fragments such as Fab are suitable for utilization as diagnostic drug because of their short half-lives in blood and the characteristics of renal excretion (Nat. Biotechnol., 2005 September; 23 (9): 1126-36).

CITATION LIST

Patent Literature

PTL 1: WO2010/050528
PTL 2: WO2008/040362

Non Patent Literature

NPL 1: Glycoconj. J., 2013 April; 30 (3): 227-36
NPL 2: Cancer Immunol Immunother, 2006 November; 55 (11): 1337-47

SUMMARY OF INVENTION

Technical Problem

Monovalent Fab fragments have a molecular weight of approximately 50 kDa, which is smaller than antibodies which have a molecular weight of approximately 150 kDa, are eliminated by renal excretion, and also have a short half-life in blood. Hence, they reach a tumor-to-blood ratio that confers a signal-to-background ratio sufficient for visualizing a cancer, within 2 to 32 hours after administration. They lack an Fc region and therefore cause neither ADCC nor CDC. The Fab fragments are typically eliminated by renal excretion and therefore, do not interfere with the detection of hepatic metastasis. From these features, the Fab fragments can be expected to be more effective as in vivo diagnostic drugs as compared with antibodies.

However, the binding activity of the Fab fragments is often attenuated because of being monovalent, not divalent. Antibodies must be labeled with a detectable substance such as a fluorescent dye or a contrast medium for their utilization as in vivo diagnostic drugs or drugs for use in photoimmunotherapy methods. A further problem is the attenuation of their binding activity due to labeling with such a substance.

An object of the present invention is to provide a conjugate comprising an anti-human MUC1 antibody Fab fragment, a peptide linker and a ligand, and a conjugate comprising an anti-human MUC1 antibody Fab fragment and a ligand, the conjugates having excellent binding activity against human cancer-specific MUC1 equivalent to that of the anti-human MUC1 antibody Fab fragment. Another object of the present invention is to provide a composition for diagnosis comprising the conjugate and a diagnosis method using the same, and to provide a pharmaceutical composition comprising the conjugate and a treatment method using the same.

Solution to Problem

The present inventors have prepared an anti-human MUC1 antibody Fab fragment having favorable affinity for human cancer-specific MUC1 and conducted diligent studies, and consequently prepared a conjugate by binding the anti-human MUC1 antibody Fab fragment to a ligand via (or without the mediation of) a peptide linker. The conjugate has affinity for human cancer-specific MUC1 equivalent to that of the anti-human MUC1 antibody Fab fragment itself. Specifically, the present invention provides a conjugate comprising an anti-human MUC1 antibody Fab fragment, a peptide linker and a ligand, and a conjugate comprising an anti-human MUC1 antibody Fab fragment and a particular ligand. The conjugate has been further confirmed to be free from the attenuation of the binding activity against human cancer-specific MUC1 even by the binding of a labeling moiety and to retain favorable binding activity against human cancer-specific MUC1. On the basis of these results, a diagnosis approach and a treatment approach using the conjugate of the present invention are provided.

Specifically, in one aspect, the present invention can be as follows:

[1] A conjugate represented by the following formula (I):

(Y—S$_1$—X)$_p$-Fab        (I)

wherein

Fab is an anti-human MUC1 antibody Fab fragment selected from the group consisting of the following (a) and (b):

(a) an anti-human MUC1 antibody Fab fragment comprising a heavy chain fragment comprising a heavy chain variable region consisting of the amino acid sequence represented by SEQ ID NO: 8 or SEQ ID NO: 10 and a light chain comprising a light chain variable region consisting of the amino acid sequence represented by SEQ ID NO: 12, and (b) an anti-human MUC1 antibody Fab fragment comprising a heavy chain fragment comprising a heavy chain variable region derived from a heavy chain variable region consisting of the amino acid sequence represented by SEQ ID NO: 8 or SEQ ID NO: 10 by the modification of glutamine at amino acid position 1 of SEQ ID NO: 8 or SEQ ID NO: 10 into pyroglutamic acid, and a light chain comprising a light chain variable region consisting of the amino acid sequence represented by SEQ ID NO: 12;

X is a peptide linker or a bond;
S$_1$ is a spacer or a bond;
Y is a ligand; and
p is a natural number of 1 to 25;
provided that when X is a bond, S$_1$ is —CH$_2$-(1,4-phenylene)-NH—C(=S)— or a bond, and Y is 1,4,7,10-tetraazacyclododecane-1,4,7,10-tetraacetic acid (DOTA).

[2] The conjugate according to [1], wherein Fab is selected from the group consisting of the following (a) and (b):

(a) an anti-human MUC1 antibody Fab fragment comprising a heavy chain fragment consisting of the amino acid sequence represented by SEQ ID NO: 2 or SEQ ID NO: 4 and a light chain consisting of the amino acid sequence represented by SEQ ID NO: 6; and (b) an anti-human MUC1 antibody Fab fragment comprising a heavy chain fragment derived from a heavy chain fragment consisting of the amino acid sequence represented by SEQ ID NO: 2 or SEQ ID NO: 4 by the modification of glutamine at amino acid position 1 of SEQ ID NO: 2 or SEQ ID NO: 4 into pyroglutamic acid, and a light chain consisting of the amino acid sequence represented by SEQ ID NO: 6.

[3] The conjugate according to [1], wherein Fab is selected from the group consisting of the following (a) and (b):

(a) an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12; and (b) an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12.

[4] The conjugate according to [2], wherein Fab is selected from the group consisting of the following (a) and (b):

(a) an anti-human MUC1 antibody Fab fragment comprising a heavy chain fragment consisting of the amino acid sequence represented by SEQ ID NO: 4 and a light chain consisting of the amino acid sequence represented by SEQ ID NO: 6; and (b) an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

[5] The conjugate according to [4], wherein Fab is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6.

[6] The conjugate according to [4], wherein Fab is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

[7] The conjugate according to any of [1] to [6], wherein X is a peptide linker comprising a 2- to 4-amino acid peptide and having an amino acid sequence cleavable with a renal brush boarder membrane enzyme or a lysosomal enzyme.

[8] The conjugate according to [7], wherein S$_1$ is —C(=O)—CH$_2$O-(1,3-phenylene)-C(=O)—, —C(=S)—NH-(1,4-phenylene)-NH—C(=S)—, —NH—CH$_2$-(1,3-phenylene)-C(=O)—, —C(=O)—

(CH₂CH₂O)₄-(1,3-phenylene)-C(=O)—, —CH₂-(1,4-phenylene)-NH—C(=S)—, —NH—(CH₂)₂—C(=O)—, —C(=O)-(1,4-phenylene)-C(=O)—, —C(=O)-(1,3-phenylene)-C(=O)—, —C(=O)—(CH₂)₂—C(=O)—, or a bond, and X is a peptide linker selected from the group consisting of the following (1) to (9):
(1) -Met-Ile-NH—(CH₂)₂—Z₁—,
(2) -Gly-Lys-Z₂—,
(3) -Gly-Phe-Lys-Z₂—,
(4) -Met-Val-Lys-Z₂—,
(5) -Gly-Tyr-CH₂—C(=O)—NH—(CH₂)₂—Z₁—,
(6) -Gly-Lys-Lys-Z₂—,
(7) -Gly-Arg-Lys-Z₂—,
(8) -Gly-Lys-C(=S)—NH-(1,4-phenylene)-NH—C(=S)—, and
(9) -Met-Ile-NH—(CH₂)₂—NH—C(=S)—NH-(1,4-phenylene)-NH—C(=S)—, wherein Met represents methionine, Ile represents isoleucine, Gly represents glycine, Lys represents lysine, Phe represents phenylalanine, Val represents valine, Tyr represents tyrosine, Arg represents arginine, Z₁ represents a group represented by the following formula (II), -Lys-Z₂— represents a group represented by the following formula (III), -Tyr-CH₂— represents a group represented by the following formula (IV), and -Lys-C(=S)— represents a group represented by the following formula (V):

[Chemical Formula 1]

(II)

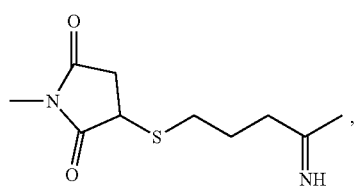

(III)

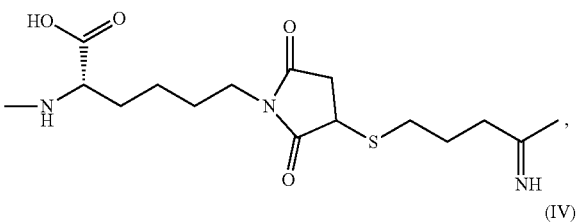

(IV)

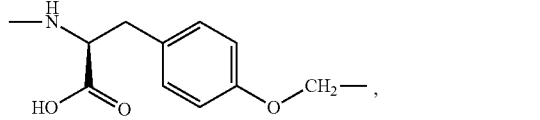

(V)

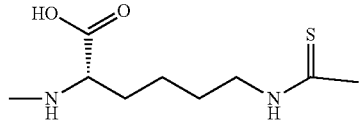

[9] The conjugate according to any one of [1] to [8] wherein Y is deferoxamine (DFO) or 1,4,7,10-tetraazacyclododecane-1,4,7,10-tetraacetic acid (DOTA).

[10] The conjugate according to any one of [1] to [9], wherein Y is DFO.

[11] The conjugate according to any of [1] to [9], wherein Y is DOTA.

[12] The conjugate according to any of [1] to [6], wherein Y is DOTA,
S₁ is —CH₂-(1,4-phenylene)-NH—C(=S)— or a bond, and
X is a bond.

[13] The conjugate according to [10], wherein (Y—S₁—X)ₚ-Fab is selected from the group consisting of

[Chemical Formula 2]

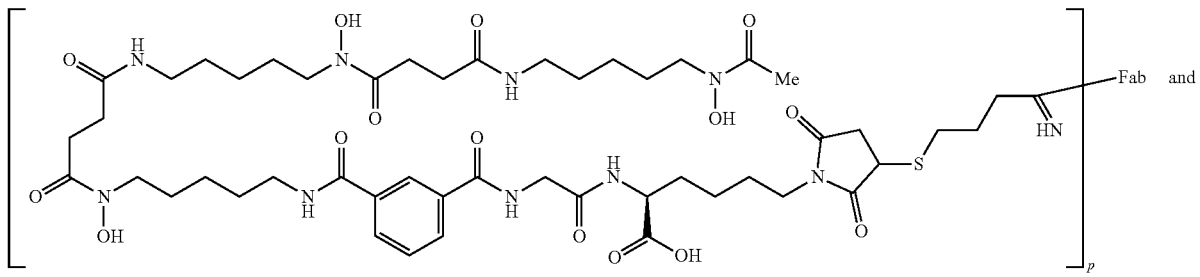

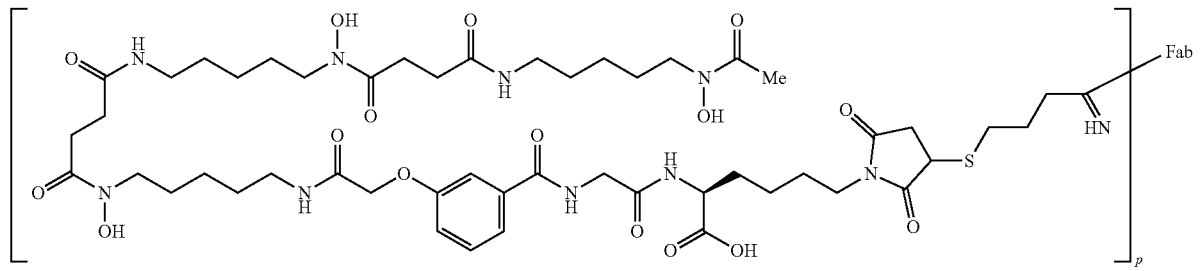

and the nitrogen atom of an amino group contained in Fab is banded to the carbon atom of the terminal C(=NH) group of X.
[14] The conjugate according to [11], wherein (Y—S$_1$—X)$_p$-Fab is selected from the group consisting of
[Chemical Formula 3]
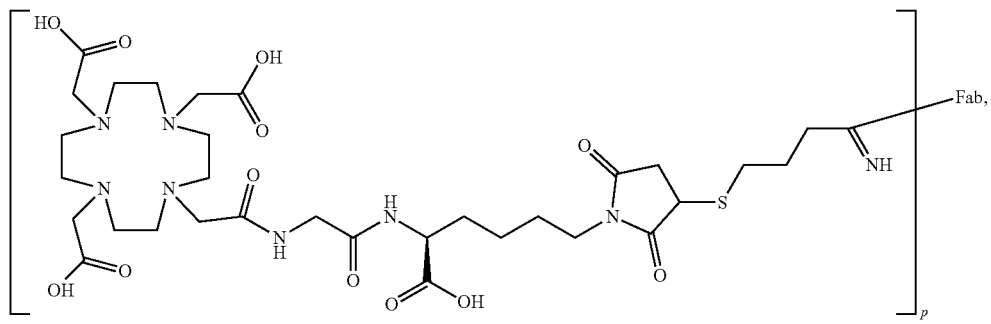
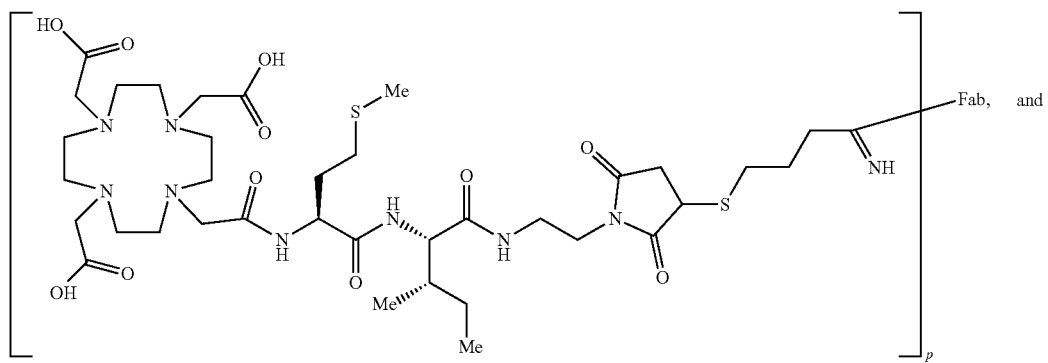
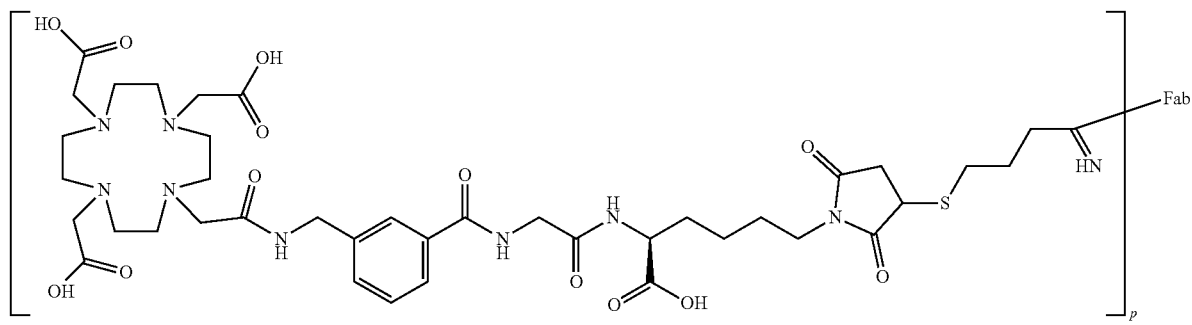

and the nitrogen atom of an amino group contained in Fab is bonded to the carbon atom of the terminal C(=NH) group of X,

[15] The conjugate according to [12], wherein (Y—S$_1$—X)$_p$-Fab is selected from the group consisting of

[Chemical Formula 4]

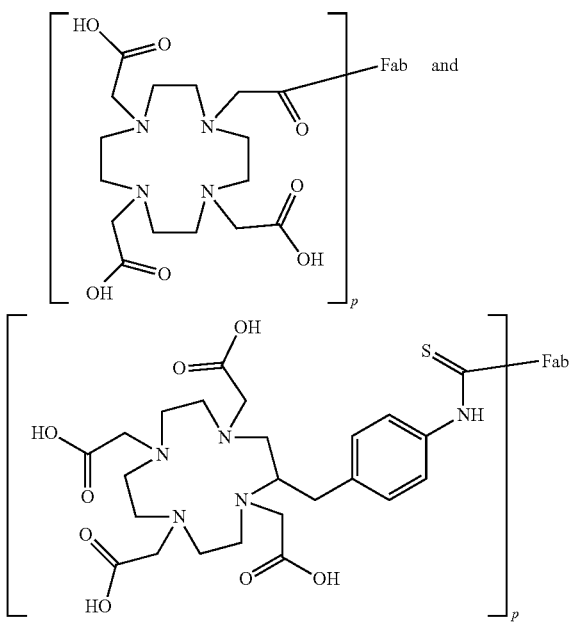

and the nitrogen atom of an amino group contained in Fab is bonded to the carbon atom of the terminal C(=O) group or C(=S) group.

[16] The conjugate according to [13] to [15], wherein p is a natural number of 1 to 4

[17] The conjugate according to any of [1] to [16], further comprising a metal.

[18] The conjugate according to [17], wherein the metal is a metal radioisotope.

[19] The conjugate according to [18], wherein the metal is $^{89}$Zr.

[20] The conjugate according to any of [18] to [19] which is a PET tracer.

[21] A composition for diagnosis comprising one or more conjugate according to any of [17] to [20], and a pharmaceutically acceptable carrier.

[22] The composition for diagnosis according to [21] which is an early diagnostic drug, a staging drug, or an intraoperative diagnostic drug.

[23] The composition for diagnosis according to [21] or [22] which is used in the diagnosis of a cancer expressing human MUC1.

[24] The composition for diagnosis according to [23], wherein the cancer is breast cancer, lung cancer, colorectal cancer, bladder cancer, thyroid gland cancer, stomach cancer, pancreatic cancer, kidney cancer, ovary cancer, or uterine cervical cancer.

[25] A pharmaceutical composition comprising one or more conjugate according to any of [17] to [20], and a pharmaceutically acceptable carrier.

[26] The pharmaceutical composition according to [25] which is a pharmaceutical composition for treating a cancer expressing human MUC1.

[27] The pharmaceutical composition according to [26], wherein the cancer is breast cancer, lung cancer, colorectal cancer, bladder cancer, skin cancer, thyroid gland cancer, stomach cancer, pancreatic cancer, kidney cancer, ovary cancer, or uterine cervical cancer.

[28] Use of the conjugate according to any of [17] to [20] for the production of a composition for the diagnosis of cancer and/or a pharmaceutical composition for treating cancer.

[29] The conjugate according to any of [17] to [20] for use in the diagnosis of a cancer and/or treatment of a cancer.

[30] A method for diagnosing a cancer, comprising administering a diagnostically effective amount of the conjugate according to any of [17] to [20] to a subject.

[31] A method for treating a cancer, comprising administering a therapeutically effective amount of the conjugate according to any of [17] to [20] to a subject.

[32] Use of the conjugate according to any of [17] to [20] for the diagnosis of a cancer and/or treatment of a cancer.

Advantageous Effects of Invention

The conjugate comprising an anti-human MUC1 antibody Fab fragment, a peptide linker and a ligand, and the conjugate comprising an anti-human MUC1 antibody Fab fragment and a particular ligand according to the present invention have excellent binding activity against human cancer-specific MUC1. Hence, the conjugate of the present invention further comprising a metal is expected to be useful in the diagnosis and/or treatment of cancers.

BRIEF DESCRIPTION OF DRAWINGS

FIG. 1 is a graph and a table showing the binding activity of P10-1 Fab, P10-2 Fab and 1B2 Fab of Comparative Example against human cancer-specific MUC1.

DESCRIPTION OF EMBODIMENTS

Hereinafter, the present invention will be described in detail. However, the present invention is not limited thereby. Scientific terms and technical terms used in relation to the present invention have meanings generally understood by those skilled in the art, unless otherwise specified herein.

1. Conjugate of Present Invention

The conjugate of the present invention is a conjugate represented by the following formula (I):

wherein

Fab is an anti-human MUC1 antibody Fab fragment;

X is a peptide linker or a bond;

S$_1$ is a spacer or a bond;

Y is a ligand; and p is a natural number of 1 to 25;

provided that when X is a bond, S$_1$ is —CH$_2$-(1,4-phenylene)-NH—C(=S)— or a bond, and Y is 1,4,7,10-tetraazacyclododecane-1,4,7,10-tetraacetic acid (DOTA).

1-1. Anti-Human MUC1 Antibody Fab Fragment (Fab)

The anti-human MUC1 antibody Fab fragment represented by "Fab" in formula (I) will be described.

The basic structure of an antibody molecule is common among classes and is constituted by heavy chains having a molecular weight of 50000 to 70000 and light chains having a molecular weight of 20000 to 30000. The heavy chain usually consists of a polypeptide chain comprising approximately 440 amino acids, has a structure characteristic of each class, and is called γ, μ, α, δ, and ε chains corresponding to IgG, IgM, IgA, IgD, and IgE. IgG further has IgG1, IgG2, IgG3, and IgG4 which are called γ1, γ2, γ3, and γ4, respectively. The light chain usually consists of a polypeptide chain comprising approximately 220 amino acids and known as two types, L and K types, which are called λ and κ chains, respectively. As for the peptide configuration of the basic structure of the antibody molecule, two homologous heavy chains and two homologous light chains are linked through disulfide bonds (S—S bonds) and non-covalent bonds to form a molecular weight of 150000 to 190000. The two light chains can pair with any of the heavy chains. An individual antibody molecule is constantly made up of two identical light chains and two identical heavy chains.

Four (or five for μ and ε chains) and two intrachain S—S bonds are present in the heavy chain and the light chain, respectively, and each constitute one loop per 100 to 110 amino acid residues. This conformation is similar among the loops and is called structural unit or domain. For both the heavy chain and the light chain, a domain positioned at the N terminus does not have a constant amino acid sequence even among preparations from the same classes (subclasses) of animals of the same species, and is thus called variable region. The respective domains are called heavy chain variable region ($V_H$) and light chain variable region ($V_L$). An amino acid sequence on the C-terminal side therefrom is almost constant on a class or subclass basis and called constant region. The respective domains are represented by $C_H1$, $C_H2$, $C_H3$ and $C_L$.

The binding specificity of the antibody for an antigen depends on the amino acid sequence of a moiety constituted by $V_H$ and $V_L$. On the other hand, biological activity such as binding to complements or various cells reflects the difference in structure among the constant regions of Igs of respective classes. It is known that the variability of the heavy chain and light chain variable regions is limited substantially by three small hypervariable regions present in both the chains. These regions are called complementarity determining regions (CDRs; CDR1, CDR2, and CDR3 in order from the N-terminal side). The remaining moieties of the variable region are called framework regions (FRs) and are relatively constant.

A region between the $C_H1$ domain and the $C_H2$ domain of the heavy chain constant region of an antibody is called hinge region. This region is rich in proline residues and contains a plurality of interchain S—S bonds that connect two heavy chains. For example, the hinge regions of human IgG1, IgG2, IgG3, and IgG4 contain 2, 4, 11, and 2 cysteine residues, respectively, which constitute S—S bonds between the heavy chains. The hinge region is a region highly sensitive to a proteolytic enzyme such as papain or pepsin. In the case of digesting an antibody with papain, the heavy chains are cleaved at a position on the N-terminal side from the inter-heavy chain S—S bonds of the hinge region and thus decomposed into two Fab fragments and one Fc fragment. The Fab fragment is constituted by a light chain and a heavy chain fragment comprising a heavy chain variable region ($V_H$), a $C_H1$ domain and a portion of the hinge region. The Fab fragment comprises variable regions and has antigen binding activity.

In one embodiment, the anti-human MUC1 antibody Fab fragment contained in the conjugate of the present invention is a Fab fragment having the following feature:

an anti-human MUC1 antibody Fab fragment comprising a heavy chain fragment comprising a heavy chain variable region consisting of the amino acid sequence represented by SEQ ID NO: 8 or SEQ ID NO: 10 and a light chain comprising a light chain variable region consisting of the amino acid sequence represented by SEQ ID NO: 12.

In one embodiment, the anti-human MUC1 antibody Fab fragment contained in the conjugate of the present invention is an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12.

Any constant region of Igγ1, Igγ2, Igγ3 or Igγ4, etc. is selectable as the heavy chain constant region of the anti-human MUC1 antibody Fab fragment contained in the conjugate of the present invention. In one embodiment, the heavy chain constant region of the anti-human MUC1 antibody Fab fragment contained in the conjugate of the present invention is a human Igγ1 constant region.

Any constant region of Igλ or Igκ is selectable as the light chain constant region of the anti-human MUC1 antibody Fab fragment contained in the conjugate of the present invention. In one embodiment, the light chain constant region of the anti-human MUC1 antibody Fab fragment contained in the conjugate of the present invention is a human Igκ constant region.

In one embodiment, the anti-human MUC1 antibody Fab fragment contained in the conjugate of the present invention is the following Fab fragment:

an anti-human MUC1 antibody Fab fragment comprising a heavy chain fragment consisting of the amino acid sequence represented by SEQ ID NO: 2 or SEQ ID NO: 4 and a light chain consisting of the amino acid sequence represented by SEQ ID NO: 6.

In one embodiment, the anti-human MUC1 antibody Fab fragment contained in the conjugate of the present invention is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6.

In the case of expressing an antibody including a Fab fragment in cells, the antibody is known to undergo a posttranslational modification. Examples of the posttranslational modification include the cleavage of heavy chain C-terminal lysine by carboxypeptidase, the modification of heavy chain and light chain N-terminal glutamine or glutamic acid into pyroglutamic acid by pyroglutamylation, glycosylation, oxidation, deamidation, and glycation. Such a posttranslational modification is known to occur in various antibodies (Journal of Pharmaceutical Sciences, 2008 July; 97(7): 2426-2447).

The anti-human MUC1 antibody Fab fragment contained in the conjugate of the present invention can also include a Fab fragment resulting from the posttranslational modification. Examples of the anti-human MUC1 antibody Fab fragment of the present invention resulting from the posttranslational modification include an anti-human MUC1 antibody Fab fragment having an N-terminally pyroglutamylated heavy chain. It is known in the art that such a posttranslational modification by N-terminal pyroglutamylation has no influence on the activity of the antibody (Anal. Biochem., 2006 Jan. 1; 348(1): 24-39).

In one embodiment, the anti-human MUC1 antibody Fab fragment contained in the conjugate of the present invention is an anti-human MUC1 antibody Fab fragment having the following feature:
  an anti-human MUC1 antibody Fab fragment comprising a heavy chain fragment comprising a heavy chain variable region derived from a heavy chain variable region consisting of the amino acid sequence represented by SEQ ID NO: 8 or SEQ ID NO: 10 by the modification of glutamine at amino acid position 1 of SEQ ID NO: 8 or SEQ ID NO: 10 into pyroglutamic acid, and a light chain comprising a light chain variable region consisting of the amino acid sequence represented by SEQ ID NO: 12.

In a certain embodiment, the anti-human MUC1 antibody Fab fragment contained in the conjugate of the present invention is an anti-human MUC1 antibody Fab fragment having the following feature:
  an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12.

In an alternative embodiment, the anti-MUC1 antibody Fab fragment contained in the conjugate of the present invention is an anti-human MUC1 antibody Fab fragment having the following feature:
  an anti-human MUC1 antibody Fab fragment comprising a heavy chain fragment derived from a heavy chain fragment consisting of the amino acid sequence represented by SEQ ID NO: 2 or SEQ ID NO: 4 by the modification of glutamine at amino acid position 1 of SEQ ID NO: 2 or SEQ ID NO: 4 into pyroglutamic acid, and a light chain consisting of the amino acid sequence represented by SEQ ID NO: 6.

In a certain embodiment, the anti-MUC1 antibody Fab fragment contained in the conjugate of the present invention is an anti-human MUC1 antibody Fab fragment having the following feature:
  an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

The anti-human MUC1 antibody Fab fragment contained in the conjugate of the present invention binds to human cancer-specific MUC1. The cancer-specific MUC1 is expressed in cancers such as breast cancer, lung cancer, colorectal cancer, bladder cancer, skin cancer, thyroid gland cancer, stomach cancer, pancreatic cancer, kidney cancer, ovary cancer or uterine cervical cancer. A method for measuring the binding activity of the obtained anti-human MUC1 antibody Fab fragment against human cancer-specific MUC1 includes methods such as ELISA and FACS. In the case of using, for example, ELISA, human cancer-specific MUC1-positive cells (e.g., T-47D cells) are immobilized onto an ELISA plate, to which the Fab fragment is then added and reacted, and then, an anti-Igκ antibody or the like labeled with horseradish peroxidase or the like is reacted. Then, the binding of the secondary antibody is identified by activity measurement using a reagent for detecting the activity thereof (e.g., a chemiluminescent horseradish peroxidase substrate for the horseradish peroxidase label) or the like.

The anti-human MUC1 antibody Fab fragment contained in the conjugate of the present invention can be readily prepared by those skilled in the art using a method known in the art on the basis of sequence information on the heavy chain fragment and the light chain of the anti-human MUC1 antibody Fab fragment disclosed herein. The anti-human MUC1 antibody Fab fragment contained in the conjugate of the present invention can be produced according to, but not particularly limited to, a method described in, for example, <Method for producing anti-human MUC1 antibody Fab fragment contained in the conjugate of the present invention> mentioned later.

1-2. Ligand (Y)

The ligand represented by "Y" in formula (I) will be described.

The "ligand" is a moiety capable of forming a chelate complex with a metal in the conjugate of the present invention and means a group constituted by a chelating agent. The constituted group is a group having a bond by the removal of a proton from the chelating agent. The group constituted by a chelating agent is bound to the anti-human MUC1 antibody Fab fragment directly or via a spacer and/or a peptide linker.

The "chelating agent" refers to a compound that can form a coordinate bond with a metal. In the present specification, examples of the "chelating agent" include siderophore and non-siderophore. Examples of the siderophore include hydroxamic acid type, catechol type, and mixed ligand type. Examples of the hydroxamic acid-type siderophore include ferrichrome, deferoxamine (DFO) represented by the following formula:

[Chemical Formula 5]

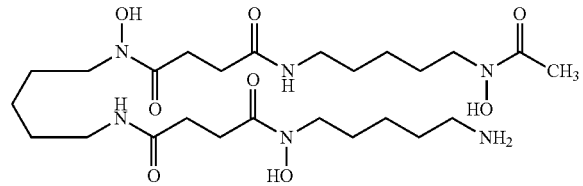

fusarinine C, ornibactin, and rhodotorulic acid. Examples of the catechol-type siderophore include enterobactin, bacillibactin, and vibriobactin. Examples of the mixed ligand-type siderophore include azotobactin, pyoverdine, and yersiniabactin. In the case of the siderophore, DFO can be reacted via its reactive functional group —$NH_2$ with the spacer or the peptide linker, and the siderophore other than DFO can also be reacted via its reactive functional group such as a carboxyl group, a hydroxy group, or an amino group with the spacer or the peptide linker by a method usually used by those skilled in the art.

Examples of the non-siderophore include DOTA (1,4,7,10-tetraazacyclododecane-1,4,7,10-tetraacetic acid, CAS No: 60239-18-1) represented by the following formula:

[Chemical Formula 6]

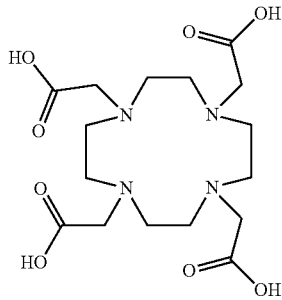

DTPA (diethylenetriaminepentaacetic acid, CAS No: 67-43-6), DTPA-BMA (1,7-bis(methylcarbamoylmethyl)-1,4,7-triazaheptane-1,4,7-triacetic acid, CAS No: 119895-95-3), EOB-DTPA (N-[(2S)-2-[bis(carboxymethyl)amino]-3-(4-ethoxyphenyl)propyl]-N-[2-[bis(carboxymethyl)amino]ethyl]glycine, CAS No: 158599-72-5), TTHA (triethylenetetraminehexaacetic acid, CAS No: 869-52-3), DO3A (1,4,7,10-tetraazacyclododecane-1,4,7-triacetic acid, CAS No: 217973-03-0), HP-DO3A (10-(2-hydroxypropyl)-1,4,7,10-tetraazacyclododecane-1,4,7-triacetic acid, CAS No: 120041-08-9), and known reactive derivatives thereof.

Examples of a certain embodiment of the "chelating agent" constituting the ligand contained in the conjugate of the present invention include DFO, DOTA, DTPA, DTPA-BMA, EOB-DTPA, DO3A, and HP-DO3A. A certain embodiment is DFO or DOTA.

Compounds and conjugates described herein also encompass free forms and salts thereof unless otherwise specified. In this context, the "salt thereof" is a salt that can be formed by the compound or the conjugate that may form an acid-addition salt or a salt with a base depending on the type of a substituent in the compound or the conjugate. Specific examples thereof include: acid-addition salts with inorganic acids such as hydrochloric acid, hydrobromic acid, hydroiodic acid, sulfuric acid, nitric acid, and phosphoric acid, or organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with inorganic bases such as sodium, potassium, magnesium, calcium, and aluminum, or organic bases such as methylamine, ethylamine, ethanolamine, lysine, and ornithine; salts with various amino acids and amino acid derivatives, such as acetylleucine; and ammonium salts. For example, DFO exists as deferoxamine methanesulfonate or exists as other salts. DTPA exits both as a free form and as sodium salt.

The conjugate of the present invention comprising a metal can be used in various contrast medium and/or cancer therapeutic agents and is used in, for example, a drug for use in an MRI contrast medium and a PET tracer.

A certain embodiment of the "chelating agent" for use in an MRI contrast medium is the siderophore or non-siderophore chelating agent described above.

A certain embodiment of the "chelating agent" for use in a PET tracer is the siderophore or non-siderophore chelating agent described above. A certain embodiment is DFO or DOTA.

In the conjugate of the present invention, the chelating agent may comprise a metal. In the present specification, the "metal" means a paramagnetic metal ion or a metal radioisotope. The metal is not particularly limited as long as the metal forms a coordinate bond to each chelating agent. A suitable combination of the chelating agent and the metal is selected according to the use purpose of the conjugate.

The paramagnetic metal ion is suitably used in an MRI contrast medium. Examples of the embodiment of the paramagnetic metal ion include, but are not limited to, $Fe^{2|}$, $Fe^{3|}$, $Cu^{2|}$, $Ni^{2|}$, $Rh^{2|}$, $Co^{2|}$, $Gd^{3|}$, $Eu^{3|}$, $Dy^{3|}$, $Tb^{3|}$, $Pm^{3|}$, $Nd^{3|}$, $Tm^{3|}$, $Ce^{3|}$, $Y^{3|}$, $Ho^{3|}$, $Er^{3+}$, $La^{3+}$, $Yb^{3+}$, $Mn^{3+}$, and $Mn^{2+}$. A certain embodiment is $Gd^{3+}$, $Mn^{3+}$, $Mn^{2+}$, $Fe^{2+}$, or $Fe^{3+}$. A certain embodiment is $Mn^{3+}$ or $Mn^{2+}$. In this case, halogen or the like can be used as a counter anion in the conjugate. Alternatively, the counter anion may be $C(=O)O^-$ of the ligand. The conjugate may further have a counter cation such as $Na^+$.

The metal radioisotope is used in, for example, a PET tracer. Examples of a certain embodiment of the metal radioisotope include, but are not limited to, $^{89}Zr$, $^{51}Mn$, $^{52}Fe$, $^{60}Cu$, $^{67}Ga$, $^{68}Ga$, $^{72}As$, $^{90}Y$, $^{99m}Tc$, $^{111}In$, and $^{177}Lu$. A certain embodiment of the metal radioisotope for use in a PET tracer is $^{89}Zr$, $^{60}Cu$, $^{67}Ga$, $^{68}Ga$, $^{99m}Tc$, or $^{111}In$. A certain embodiment is a radioisotope of zirconium. A certain embodiment is $^{89}Zr$. A certain embodiment of the metal radioisotope for use in the treatment of a cancer is $^{90}Y$ or $^{177}Lu$.

A certain embodiment of the conjugate of the present invention is a conjugate in which Y is DFO having a coordinate bond with $^{89}Zr$. An alternative embodiment is a conjugate in which Y is DOTA having a coordinate bond with a metal radioisotope consisting of $^{89}Zr$, $^{90}Y$, $^{67}Ga$, $^{68}Ga$ and $^{177}Lu$. An alternative embodiment is a conjugate in which Y is DOTA having a coordinate bond with a paramagnetic metal ion consisting of $^{89}Zr$, $Gd^{3+}$ and $Y^{3+}$. An alternative embodiment is a conjugate in which Y is DOTA having a coordinate bond with a paramagnetic metal ion consisting of $Gd^{3+}$ and $Y^{3+}$.

1-3. Peptide Linker or Bond (X)

In the conjugate of the present invention, the ligand (Y) or the spacer ($S_1$) and Fab may be bound directly or may be bound via the peptide linker (X). The peptide linker represented by "X" in formula (I) will be described.

In the present specification, the "peptide linker" is a linker comprising a 2- to 4-amino acid peptide and, if desired, may have spacer $Z_1$ or $Z_2$ suitable for binding to the anti-human MUC1 antibody Fab fragment. In this context, the peptide contained in the peptide linker is not particularly limited and is preferably a peptide consisting of 2 to 4 amino acids each selected from the group consisting of glycine (Gly), lysine (Lys), methionine (Met), isoleucine (Ile), phenylalanine (Phe), valine (Val), tyrosine (Tyr), arginine (Arg), alanine (Ala), glutamine (Gln), glutamic acid (Glu), asparagine (Asn), aspartic acid (Asp), histidine (His) and leucine (Leu), more preferably a peptide consisting of 2 to 4 amino acids each selected from the group consisting of glycine, lysine, methionine, isoleucine, phenylalanine, valine, tyrosine and arginine. The conformation of each amino acid residue other than glycine is an L-form unless otherwise specified.

A certain embodiment of the peptide linker is a peptide linker comprising a 2- to 4-amino acid peptide and having an amino acid sequence cleavable with a renal brush boarder membrane enzyme or a lysosomal enzyme, and optionally further having a spacer. Since the peptide linker having an amino acid sequence cleavable with a renal brush boarder membrane enzyme or a lysosomal enzyme is specifically cleaved by these enzymes present in the kidney, it has been reported that the accumulation of a labeling moiety to the kidney is reduced. For example, Adv Drug Deliv Rev. 2008 September; 60 (12): 1319-28, Bioconjug Chem. 2005 November-December; 16 (6): 1610-6, and Cancer Res. 1999 Jan. 1; 59 (1): 128-34 state that a glycine-lysine linker is specifically cleaved by a renal brush boarder membrane enzyme present in the kidney. Japanese Patent No. 6164556 states that a glycine-phenylalanine-lysine linker is specifically cleaved by a renal brush boarder membrane enzyme present in the kidney. Furthermore, Bioconjug Chem. 2002 September-October; 13 (5): 985-95 states that a linker comprising a glycine-leucine-glycine-lysine sequence is specifically cleaved by a renal brush boarder membrane enzyme, and Bioconjug Chem. 2013 Feb. 20; 24 (2): 291-9 states that a glycine-tyrosine linker is specifically cleaved by this enzyme. Also, Bioconjug Chem. 2014 Nov. 19; 25 (11): 2038-45 states that a linker comprising a methionine-isoleucine sequence is specifically cleaved by a lysosomal enzyme present in the kidney. A certain embodiment of the peptide linker is a peptide linker comprising an amino acid sequence selected from the group consisting of Met-Ile, Gly-Lys, Gly-Phe-Lys, Met-Val-Lys, Gly-Tyr, Gly-Lys-Lys, and Gly-Arg-Lys. A certain embodiment is a peptide linker comprising an amino acid sequence selected from the group consisting of Gly-Lys and Met-Ile.

The "peptide linker" may arbitrarily have a spacer suitable for binding to the anti-human MUC1 antibody Fab fragment. In this context, the spacer suitable for binding to the anti-human MUC1 antibody Fab fragment is a group that forms an organochemical bond between the peptide linker moiety and the nitrogen atom of an amino group or a disulfide bond-derived thiol group of the anti-human MUC1 antibody Fab fragment. A certain embodiment is a group terminally comprising a maleimide-derived group (e.g., a group represented by formula (II) given below) or an isothiocyanate-derived group (—NH—C(═S)—). A certain embodiment is —NH—(CH$_2$)$_2$—Z$_1$—, —CH$_2$—C(═O)—NH—(CH$_2$)$_2$—Z$_1$—, —C(═S)—NH-(1,4-phenylene)-NH—C(═S)—, or —NH—(CH$_2$)$_2$—NH—C(═S)—NH-(1,4-phenylene)-NH—C(═S)—. In this context, Z$_1$ is represented by formula (II) given below.

The spacer is bonded to the amino group or the carboxyl group of the terminal amino acid of the peptide, or an amino group (e.g., in lysine) or a hydroxy group (e.g., in tyrosine) in the side chain of the amino acid to form the peptide linker. Examples of the peptide linker formed through the bonding of the spacer to a functional group in the side chain of the terminal amino acid of the peptide include a group represented by the following formula (II) as a spacer integrated with Lys, which is referred to as -Lys-Z$_2$— in the present specification.

[Chemical Formula 7]

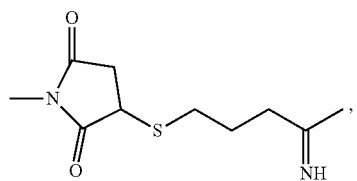

(II)

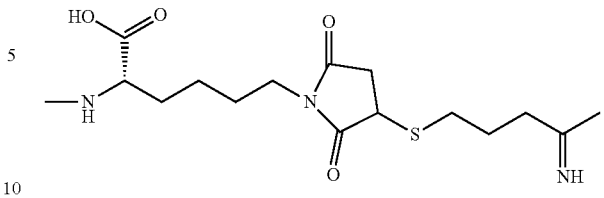

(III)

In the present specification, similar groups represented by the following formula (IV) and formula (V) having a structure where the spacer is bonded to a functional group in the side chain of the terminal amino acid are referred to as -Tyr-CH$_2$— and -Lys-C(═S)—, respectively.

[Chemical Formula 8]

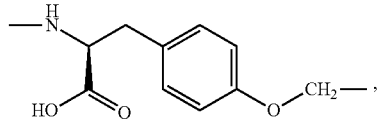

(IV)

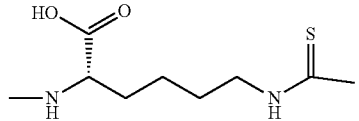

(V)

A certain embodiment of the peptide linker comprising the spacer is (1) -Met-Ile-NH—(CH$_2$)$_2$—Z$_1$—, (2) -Gly-Lys-Z$_2$—, (3) -Gly-Phe-Lys-Z$_2$—, (4) -Met-Val-Lys-Z$_2$—, (5) -Gly-Tyr-CH$_2$—C(═O)—NH—(CH$_2$)$_2$—Z$_1$—, (6) -Gly-Lys-Lys-Z$_2$—, (7) -Gly-Arg-Lys-Z$_2$—, (8) -Gly-Lys-C(═S)—NH-(1,4-phenylene)-NH—C(═S)— or (9) -Met-Ile-NH—(CH$_2$)$_2$—NH—C(═S)—NH-(1,4-phenylene)-NH—C(═S)—. A certain embodiment is (1) -Met-Ile-NH—(CH$_2$)$_2$—Z$_1$ or (2) -Gly-Lys-Z$_2$—. A certain embodiment is (8) -Gly-Lys-C(═S)—NH-(1,4-phenylene)-NH—C(═S)— or (9) -Met-Ile-NH—(CH$_2$)$_2$—NH—C(═S)—NH-(1,4-phenylene)-NH—C(═S)—.

1-4. Spacer or Bond (S$_1$)

In the conjugate of the present invention, the ligand (Y) and the peptide linker (X) or Fab may be bound directly or may be bound via a spacer.

In the present specification, the "spacer" represented by S$_1$ is a group that is introduced to create a distance between the ligand and the peptide linker or Fab or to bind the ligand to the peptide linker or Fab. Examples of a certain embodiment include —C(═O)—CH$_2$—O-(1,3-phenylene)-C(═O)—, —C(═S)—NH-(1,4-phenylene-NH—C(═S)—, —NH—CH$_2$-(1,3-phenylene)-C(═O)—, —C(═O)—(CH$_2$CH$_2$O)$_4$-(1,3-phenylene)-C(═O)—, —CH$_2$-(1,4-phenylene)-NH—C(═S)—, —NH—(CH$_2$)$_2$—C(═O)—, —C(═O)-(1,4-phenylene)-C(═O)—, —C(═O)-(1,3-phenylene)-C(═O)— and —C(═O)—(CH$_2$)$_2$—C(═O)—. A certain embodiment of S$_1$ is —C(═O)—CH$_2$O-(1,3-phenylene)-C(═O)—, —C(═S)—NH-(1,4-phenylene)-NH—C(═S)—, —C(═O)—(CH$_2$CH$_2$O)$_4$—C(═O)—, —CH$_2$—(1,4-phenylene)-NH—C(═S)—, —C(═O)-(1,4-phenylene)-C(═O)—, —C(═O)-(1,3-phenylene)-C(═O)—, —C(═O)—(CH$_2$)$_2$—C(═O)—, or a bond. A certain embodiment of S$_1$ is —C(═O)—CH$_2$O-(1,3-phenylene)-C(═O)—, —NH—CH$_2$-(1,3-phenylene)-C (=O)— or a bond. A certain embodiment of $S_1$ is a bond. In the conjugate of the present invention in which Y is DOTA, DOTA and the anti-human MUC1 antibody Fab fragment (Fab) may be bound directly or via a spacer (—CH$_2$-(1,4-phenylene)-NH—C(=S)—). However, when DOTA and the anti-human MUC1 antibody Fab fragment (Fab) are bound via a spacer —CH$_2$-(1,4-phenylene)-NH—C(=S)—, the conjugate is represented by the following formula (VI):

[Chemical Formula 9]

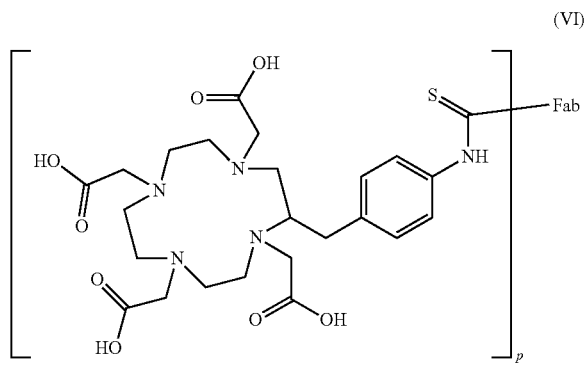

(VI)

In the production of the conjugate of the present invention, the binding between the anti-human MUC1 antibody Fab fragment and the ligand, the spacer, and/or the peptide linker, and the binding between the ligand and the spacer and/or the peptide linker can be appropriately performed by a known approach by those skilled in the art.

In the present specification, the "labeling moiety" is (i) a ligand and a peptide linker (Y—S$_1$—X wherein S$_1$ is a bond, and X is a peptide linker), (ii) a ligand (Y—S$_1$—X wherein each of S$_1$ and X is a bond), or (iii) a ligand, a spacer and a peptide linker (Y—S$_1$—X wherein S$_1$ is a spacer, and X is a peptide linker). A certain embodiment is (i) a ligand and a peptide linker, or (ii) a ligand. The ligand of the "labeling moiety" may further comprise a metal. A certain embodiment is (i) a ligand and a peptide linker or (ii) a ligand comprising a metal, and in other words, is (i) a ligand that has formed a chelate complex with a metal, and a peptide linker, or (ii) a ligand that has formed a chelate complex with a metal.

1-5. The Number (p) of Bound Labeling Moiety (Y—S$_1$—X) to Anti-Human MUC1 Antibody Fab Fragment (Fab)

The conjugate of the present invention is a conjugate in which one or more labeling moiety (Y—S$_1$—X) is bound via the nitrogen atom of one or more amino group or one or more disulfide bond-derived thiol group in the anti-human MUC1 antibody Fab fragment (Fab). The conjugate of the present invention may be a mixture of conjugates differing from each other in the number of the bound labeling moiety. In formula (I), Fab represents any Fab bound to 1 to 25 labeling moieties (Y—S$_1$—X), or a mixture thereof. A certain embodiment of the conjugate of the present invention comprises 1 to 25 labeling moieties (Y—S$_1$—X) per Fab. A certain embodiment comprises 1 to 23 labeling moieties (Y—S$_1$—X) per Fab. A certain embodiment comprises 1 to 15 labeling moieties (Y—S$_1$—X) per Fab. A certain embodiment comprises 1 to 11 labeling moieties (Y—S$_1$—X) per Fab. A certain embodiment comprises 1 to 9 labeling moieties (Y—S$_1$—X) per Fab. A certain embodiment comprises 1 to 7 labeling moieties (Y—S$_1$—X) per Fab. A certain embodiment comprises 1 to 5 labeling moieties (Y—S$_1$—X) per Fab. A certain embodiment comprises 1 to 4 labeling moieties (Y—S$_1$—X) per Fab. Specifically, a certain embodiment of "p" which represents the number of the bound labeling moiety (Y—S$_1$—X) per Fab is a natural number of 1 to 25. A certain embodiment is a natural number of 1 to 23. A certain embodiment is a natural number of 1 to 15. A certain embodiment is a natural number of 1 to 11. A certain embodiment is a natural number of 1 to 9. A certain embodiment is a natural number of 1 to 7. A certain embodiment is a natural number of 1 to 5. A certain embodiment is a natural number of 1 to 4.

2. Polynucleotide Encoding Anti-Human MUC1 Antibody Fab Fragment Contained in Conjugate of Present Invention In a certain embodiment, the anti-human MUC1 antibody Fab fragment contained in the conjugate of the present invention is encoded by a polynucleotide comprising a nucleotide sequence encoding the heavy chain fragment of the anti-human MUC1 antibody Fab fragment, and a polynucleotide comprising a nucleotide sequence encoding the light chain of the anti-human MUC1 antibody Fab fragment.

In a certain embodiment, the polynucleotide encoding the anti-human MUC1 antibody Fab fragment contained in the conjugate of the present invention is a polynucleotide comprising a nucleotide sequence encoding a heavy chain fragment comprising a heavy chain variable region consisting of the amino acid sequence represented by SEQ ID NO: 8, or a polynucleotide comprising a nucleotide sequence encoding a heavy chain fragment comprising a heavy chain variable region consisting of the amino acid sequence represented by SEQ ID NO: 10.

Examples of the polynucleotide comprising a nucleotide sequence encoding a heavy chain fragment comprising a heavy chain variable region consisting of the amino acid sequence represented by SEQ ID NO: 8 include a polynucleotide comprising the nucleotide sequence represented by SEQ ID NO: 7. Examples of the polynucleotide comprising a nucleotide sequence encoding a heavy chain fragment comprising a heavy chain variable region consisting of the amino acid sequence represented by SEQ ID NO: 10 include a polynucleotide comprising the nucleotide sequence represented by SEQ ID NO: 9.

In one embodiment, the polynucleotide encoding the anti-human MUC1 antibody Fab fragment contained in the conjugate of the present invention is a polynucleotide comprising a nucleotide sequence encoding a heavy chain fragment consisting of the amino acid sequence represented by SEQ ID NO: 2 or a polynucleotide comprising a nucleotide sequence encoding a heavy chain fragment consisting of the amino acid sequence represented by SEQ ID NO: 4.

Examples of the polynucleotide comprising a nucleotide sequence encoding a heavy chain fragment consisting of the amino acid sequence represented by SEQ ID NO: 2 include a polynucleotide comprising the nucleotide sequence represented by SEQ ID NO: 1. Examples of the polynucleotide comprising a nucleotide sequence encoding a heavy chain fragment consisting of the amino acid sequence represented by SEQ ID NO: 4 include a polynucleotide comprising the nucleotide sequence represented by SEQ ID NO: 3.

In one embodiment, the polynucleotide encoding the anti-human MUC1 antibody Fab fragment contained in the conjugate of the present invention is a polynucleotide comprising a nucleotide sequence encoding a light chain comprising a light chain variable region consisting of the amino acid sequence represented by SEQ ID NO: 12.

Examples of the polynucleotide comprising a nucleotide sequence encoding a light chain comprising a light chain variable region consisting of the amino acid sequence represented by SEQ ID NO: 12 include a polynucleotide comprising the nucleotide sequence represented by SEQ ID NO: 11.

In one embodiment, the polynucleotide encoding the anti-human MUC1 antibody Fab fragment contained in the conjugate of the present invention is a polynucleotide comprising a nucleotide sequence encoding a light chain consisting of the amino acid sequence represented by SEQ ID NO: 6.

Examples of the polynucleotide comprising a nucleotide sequence encoding a light chain consisting of the amino acid sequence represented by SEQ ID NO: 6 include a polynucleotide comprising the nucleotide sequence represented by SEQ ID NO: 5.

The polynucleotide encoding the anti-human MUC1 antibody Fab fragment contained in the conjugate of the present invention is synthesizable through the use of a gene synthesis method known in the art on the basis of nucleotide sequences designed from the amino acid sequences of the heavy chain fragment and the light chain of the anti-human MUC1 antibody Fab fragment. Various methods known to those skilled in the art, such as methods for synthesizing an antibody gene described in International Publication No. WO 90/07861 can be used as such gene synthesis methods.

3. Expression Vector for Polynucleotide Encoding Anti-Human MUC1 Antibody Fab Fragment Contained in Conjugate of Present Invention The expression vector of the polynucleotide encoding the anti-human MUC1 antibody Fab fragment contained in the conjugate of the present invention includes an expression vector comprising a polynucleotide comprising a nucleotide sequence encoding the heavy chain fragment of the anti-human MUC1 antibody Fab fragment, an expression vector comprising a polynucleotide comprising a nucleotide sequence encoding the light chain of the anti-human MUC1 antibody Fab fragment, and an expression vector comprising a polynucleotide comprising a nucleotide sequence encoding the heavy chain fragment of the anti-human MUC1 antibody Fab fragment and a polynucleotide comprising a nucleotide sequence encoding the light chain of the anti-human MUC1 antibody Fab fragment.

Preferred examples of the expression vector include an expression vector comprising a polynucleotide comprising a nucleotide sequence encoding a heavy chain fragment consisting of the amino acid sequence represented by SEQ ID NO: 4, an expression vector comprising a polynucleotide comprising a nucleotide sequence encoding a light chain consisting of the amino acid sequence represented by SEQ ID NO: 6, and an expression vector comprising a polynucleotide comprising a nucleotide sequence encoding a heavy chain fragment consisting of the amino acid sequence represented by SEQ ID NO: 4 and a polynucleotide comprising a nucleotide sequence encoding a light chain consisting of the amino acid sequence represented by SEQ ID NO: 6.

Such an expression vector is not particularly limited as long as a polypeptide encoded by the polynucleotide of the present invention can be produced in various host cells of prokaryotic cells and/or eukaryotic cells. Examples of such an expression vector include plasmid vectors and virus vectors (e.g., adenovirus and retrovirus). Preferably, pEE6.4 or pEE12.4 (Lonza Ltd.) can be used.

Such an expression vector can comprise a promoter operably linked to a gene encoding the heavy chain fragment and/or the light chain in the polynucleotide encoding the anti-human MUC1 antibody Fab fragment contained in the conjugate of the present invention. Examples of the promoter for expressing the Fab fragment in a host cell include Trp promoter, lac promoter, recA promoter, λPL promoter, lpp promoter, and tac promoter when the host cell is a bacterium of the genus *Escherichia*. Examples of the promoter for expression in yeasts include PH05 promoter, PGK promoter, GAP promoter, and ADH promoter. Examples of the promoter for expression in bacteria of the genus *Bacillus* include SL01 promoter, SP02 promoter, and penP promoter. Examples thereof include promoters derived from viruses such as CMV, RSV, and SV40, retrovirus promoter, actin promoter, EF (elongation factor) 1α promoter, and heat shock promoter when the host is a eukaryotic cell such as a mammalian cell.

In the case of using a bacterium, particularly, *E. coli*, as a host cell, these expression vector can further comprise a start codon, a stop codon, a terminator region and a replicable unit. On the other hand, in the case of using a yeast, an animal cell or an insect cell as a host, the expression vector can comprise a start codon and a stop codon. In this case, an enhancer sequence, 5' and 3' untranslated regions of a gene encoding the heavy chain fragment and/or the light chain of the present invention, a secretion signal sequence, a splicing junction, a polyadenylation site, or a replicable unit, etc. may be contained therein. Also, a selective marker usually used (e.g., tetracycline resistance gene, ampicillin resistance gene, kanamycin resistance gene, neomycin resistance gene, dihydrofolate reductase gene) may be contained therein according to a purpose.

4. Host Cell to be Transformed with Expression Vector

The host cell transformed with the expression vector includes a host cell, selected from the group consisting of the following (a) to (d):
  (a) a host cell transformed with an expression vector comprising a polynucleotide comprising a nucleotide sequence encoding the heavy chain fragment of the anti-human MUC1 antibody Fab fragment;
  (b) a host cell transformed with an expression vector comprising a polynucleotide comprising a nucleotide sequence encoding the light chain of the anti-human MUC1 antibody Fab fragment;
  (c) a host cell transformed with an expression vector comprising a polynucleotide comprising a nucleotide sequence encoding the heavy chain fragment of the anti-human MUC1 antibody Fab fragment and a polynucleotide comprising a nucleotide sequence encoding the light chain of the anti-human MUC1 antibody Fab fragment; and
  (d) a host cell transformed with an expression vector comprising a polynucleotide comprising a nucleotide sequence encoding the heavy chain fragment of the anti-human MUC1 antibody Fab fragment and an expression vector comprising a polynucleotide comprising a nucleotide sequence encoding the light chain of the anti-human MUC1 antibody Fab fragment.

In one embodiment, the host cell transformed with the expression vector is a host cell transformed with the expression vector, selected from the group consisting of the following (a) to (d):

(a) a host cell transformed with an expression vector comprising a polynucleotide comprising a nucleotide sequence encoding a heavy chain fragment consisting of the amino acid sequence represented by SEQ ID NO: 4;

(b) a host cell transformed with an expression vector comprising a polynucleotide comprising a nucleotide sequence encoding a light chain consisting of the amino acid sequence represented by SEQ ID NO: 6;

(c) a host cell transformed with an expression vector comprising a polynucleotide comprising a nucleotide sequence encoding a heavy chain fragment consisting of the amino acid sequence represented by SEQ ID NO: 4 and a polynucleotide comprising a nucleotide sequence encoding a light chain consisting of the amino acid sequence represented by SEQ ID NO: 6; and (d) a host cell transformed with an expression vector comprising a polynucleotide comprising a nucleotide sequence encoding a heavy chain fragment consisting of the amino acid sequence represented by SEQ ID NO: 4 and an expression vector comprising a polynucleotide comprising a nucleotide sequence encoding a light chain consisting of the amino acid sequence represented by SEQ ID NO: 6.

The host cell transformed with the expression vector is not particularly limited as long as it is compatible with the expression vector used and can be transformed with the expression vector to express the Fab fragment. Examples thereof include various cells such as natural cells and artificially established cells usually used in the technical field of the present invention (e.g., bacteria (bacteria of the genus *Escherichia* and bacteria of the genus *Bacillus*), yeasts (the genus *Saccharomyces*, the genus *Pichia*, etc.), animal cells and insect cells (e.g., Sf9)), and mammalian cell lines (e.g., cultured cells such as CHO-K1SV cells, CHO-DG44 cells, and 293 cells). The transformation itself can be performed by a known method, for example, a calcium phosphate method or an electroporation method.

5. Method for Producing Anti-Human MUC1 Antibody Fab Fragment Contained in Conjugate of Present Invention The production of an anti-human MUC1 antibody Fab fragment contained in the conjugate of the present invention comprises the step of culturing the transformed host cell described above to express the anti-human MUC1 antibody Fab fragment.

In one embodiment, the transformed host cell to be cultured in the production of an anti-human MUC1 antibody Fab fragment contained in the conjugate of the present invention is selected from the group consisting of the following (a) to (c):

(a) a host cell transformed with an expression vector comprising a polynucleotide comprising a nucleotide sequence encoding the heavy chain fragment of the anti-human MUC1 antibody Fab fragment contained in the conjugate of the present invention and a polynucleotide comprising a nucleotide sequence encoding the light chain of the anti-human MUC1 antibody Fab fragment contained in the conjugate of the present invention;

(b) a host cell transformed with an expression vector comprising a polynucleotide comprising a nucleotide sequence encoding the heavy chain fragment of the anti-human MUC1 antibody Fab fragment contained in the conjugate of the present invention and an expression vector comprising a polynucleotide comprising a nucleotide sequence encoding the light chain of the anti-human MUC1 antibody Fab fragment contained in the conjugate of the present invention; and (c) a host cell transformed with an expression vector comprising a polynucleotide comprising a nucleotide sequence encoding the heavy chain fragment of the anti-human MUC1 antibody Fab fragment contained in the conjugate of the present invention, and a host cell transformed with an expression vector comprising a polynucleotide comprising a nucleotide sequence encoding the light chain of the anti-human MUC1 antibody Fab fragment contained in the conjugate of the present invention.

A certain form of the transformed host cell to be cultured in the production of an anti-human MUC1 antibody Fab fragment contained in the conjugate of the present invention is selected from the group consisting of the following (a) to (c):

(a) a host cell transformed with an expression vector comprising a polynucleotide comprising a nucleotide sequence encoding a heavy chain fragment consisting of the amino acid sequence represented by SEQ ID NO: 4 and a polynucleotide comprising a nucleotide sequence encoding a light chain consisting of the amino acid sequence represented by SEQ ID NO: 6;

(b) a host cell transformed with an expression vector comprising a polynucleotide comprising a nucleotide sequence encoding a heavy chain fragment consisting of the amino acid sequence represented by SEQ ID NO: 4 and an expression vector comprising a polynucleotide comprising a nucleotide sequence encoding a light chain consisting of the amino acid sequence represented by SEQ ID NO: 6; and (c) a host cell transformed with an expression vector comprising a polynucleotide comprising a nucleotide sequence encoding a heavy chain fragment consisting of the amino acid sequence represented by SEQ ID NO: 4, and a host cell transformed with an expression vector comprising a polynucleotide comprising a nucleotide sequence encoding a light chain consisting of the amino acid sequence represented by SEQ ID NO: 6.

Preferably, the transformed host cell used is a host cell transformed with an expression vector comprising a polynucleotide comprising a nucleotide sequence encoding the heavy chain fragment of the anti-human MUC1 antibody Fab fragment contained in the conjugate of the present invention and a polynucleotide comprising a nucleotide sequence encoding the light chain of the anti-human MUC1 antibody Fab fragment contained in the conjugate of the present invention, or a host cell transformed with an expression vector comprising a polynucleotide comprising a nucleotide sequence encoding the heavy chain fragment of the anti-human MUC1 antibody Fab fragment contained in the conjugate of the present invention and an expression vector comprising a polynucleotide comprising a nucleotide sequence encoding the light chain of the anti-human MUC1 antibody Fab fragment contained in the conjugate of the present invention.

In the production of an anti-human MUC1 antibody Fab fragment contained in the conjugate of the present invention, the transformed host cell can be cultured in a nutrient medium. The nutrient medium preferably contains a carbon source, an inorganic nitrogen source or an organic nitrogen source necessary for the growth of the transformed host cell. Examples of the carbon source include glucose, dextran, soluble starch, and sucrose. Examples of the inorganic nitrogen source or the organic nitrogen source include ammonium salts, nitrates, amino acids, corn steep liquor, peptone, casein, meat extracts, soymeal, and potato extracts. Also, other nutrients (e.g., inorganic salts (e.g., calcium chloride, sodium dihydrogen phosphate, and magnesium chloride), vitamins, and antibiotics (e.g., tetracycline, neomycin, ampicillin, and kanamycin)) may be contained therein, if desired.

The culture itself of the transformed host cell is performed by a known method. Culture conditions, for example, temperature, medium pH and culture time, are appropriately selected. When the host is, for example, an animal cell, MEM medium (Science; 1952; 122: 501), DMEM medium (Virology; 1959; 8: 396-97), RPMI1640 medium (J. Am. Med. Assoc.; 1967; 199: 519-24), 199 medium (Proc. Soc. Exp. Biol. Med.; 1950; 73:1-8), or the like containing approximately 5 to 20% of fetal bovine serum can be used as a medium. The medium pH is preferably approximately 6 to 8. The culture is usually performed at approximately 30 to 40° C. for approximately 15 to 336 hours, and aeration or stirring can also be performed, if necessary. When the host is an insect cell, examples thereof include Grace's medium (PNAS; 1985; 82: 8404-8) containing fetal bovine serum. Its pH is preferably approximately 5 to 8. The culture is usually performed at approximately 20 to 40° C. for 15 to 100 hours, and aeration or stirring can also be performed, if necessary. When the host is a bacterium, an actinomycete, a yeast, or a filamentous fungus, for example, a liquid medium containing the nutrient source described above is appropriate. A medium of pH 5 to 8 is preferred. When the host is *E. coli*, preferred examples of the medium include LB medium and M9 medium (Miller et al., Exp. Mol. Genet, Cold Spring Harbor Laboratory; 1972: 431). In such a case, the culture can usually be performed at 14 to 43° C. for approximately 3 to 24 hours with aeration or stirring, if necessary. When the host is a bacterium of the genus *Bacillus*, it can usually be performed at 30 to 40° C. for approximately 16 to 96 hours with aeration or stirring, if necessary. When the host is a yeast, examples of the medium include Burkholder minimum medium (PNAS; 1980; 77: 4505-8). Its pH is desirably 5 to 8. The culture is usually performed at approximately 20 to 35° C. for approximately 14 to 144 hours, and aeration or stirring can also be performed, if necessary.

The production of an anti-human MUC1 antibody Fab fragment contained in the conjugate of the present invention may comprise the step of recovering, preferably isolating or purifying, the expressed anti-human MUC1 antibody Fab fragment, in addition to the step of culturing the transformed host cell described above to express the anti-human MUC1 antibody Fab fragment. Examples of the isolation or purification method include: methods exploiting solubility, such as salting out and a solvent precipitation method; methods exploiting difference in molecular weight, such as dialysis, ultrafiltration, gel filtration, and sodium dodecyl sulfate-polyacrylamide gel electrophoresis; methods exploiting charge, such as ion-exchange chromatography and hydroxylapatite chromatography; methods exploiting specific affinity, such as affinity chromatography; methods exploiting difference in hydrophobicity, such as reverse-phase high-performance liquid chromatography; and methods exploiting difference in isoelectric point, such as isoelectric focusing.

6. Method for Producing Conjugate According to Present Invention

The method for producing a conjugate according to the present invention can comprise the step of covalently binding an anti-human MUC1 antibody Fab fragment to a labeling moiety (Y—$S_1$—X). The binding between components in the labeling moiety (Y—$S_1$—X) can be appropriately performed by a known approach by those skilled in the art. As a reaction example, the ligand (Y) is bound to the peptide linker (X) directly or via the spacer ($S_1$), and then, the peptide linker can be bound to the anti-human MUC1 antibody Fab fragment. Alternatively, the anti-human MUC1 antibody Fab fragment may be bound to the peptide linker (X), and then, the peptide linker and the ligand (Y) can be bound directly or via the spacer ($S_1$). Furthermore, the ligand, for example, DOTA, and the anti-human MUC1 antibody Fab fragment may be bound directly by a known approach. A compound of the ligand bound to the spacer ($S_1$) in advance may be used as a starting material.

The method for producing a conjugate according to the present invention may also comprise the steps of: culturing the transformed host cell described above to express the anti-human MUC1 antibody Fab fragment; and covalently binding the Fab fragment to a labeling moiety (Y—$S_1$—X). The method for producing a conjugate according to the present invention may also comprise the steps of: culturing the transformed host cell described above to express the anti-human MUC1 antibody Fab fragment; recovering the expressed Fab fragment; and covalently binding the Fab fragment to a labeling moiety (Y—$S_1$—X). The method for producing a conjugate according to the present invention may further comprise the step of adding a metal. The chelating agent, peptide linker, spacer, the number of the labeling moiety, metal, etc. used can employ those described in the present specification.

The method for producing a conjugate according to the present invention may be carried out as a method comprising two or more of the steps defined above as a series of steps or may be carried out as a method comprising at least one of the steps defined above. For example, a method comprising the step of binding an anti-human MUC1 antibody Fab fragment to a labeling moiety (Y—$S_1$—X), and a method comprising the step of coordinating the anti-human MUC1 antibody Fab fragment bound to the labeling moiety (Y—$S_1$—X) with a metal are also included in the method for producing a conjugate according to the present invention. Also, the method for producing a conjugate according to the present invention includes a method having a different order of steps. For example, a method comprising coordinating a ligand with a metal, and then covalently binding the resulting labeling moiety (Y—$S_1$—X) to an anti-human MUC1 antibody Fab fragment is also included in the method for producing a conjugate according to the present invention.

7. Composition for Diagnosis and Diagnosis Method

The present invention relates to a composition for diagnosis comprising the conjugate of the present invention comprising a metal (hereinafter, referred to as the detectable conjugate of the present invention). The composition for diagnosis of the present invention may comprise one or more conjugate of the present invention. Specifically, the composition for diagnosis of the present invention may comprise one conjugate of the present invention, or may comprise two or more conjugates of the present invention in combination. The detectable conjugate of the present invention can be formulated according to a routine method and utilized as an early diagnostic drug or a staging drug (particularly, a cancer diagnostic drug).

The early diagnostic drug means a diagnostic drug aimed at performing diagnosis when no condition is observed or at an early stage. For example, for cancers, it means a diagnostic drug that is used when no condition is observed or at stage 0 or stage 1.

The staging drug means a diagnostic drug capable of examining the degree of progression of a condition. For example, for cancers, it means a diagnostic drug capable of examining the stage thereof.

The cancer expected to be able to be diagnosed by the composition for diagnosis of the present invention is a cancer expressing human MUC1. Examples of a certain embodiment include breast cancer, lung cancer, colorectal cancer, bladder cancer, skin cancer, thyroid gland cancer, stomach cancer, pancreatic cancer, kidney cancer, ovary cancer and uterine cervical cancer. Preferably, the cancer is breast cancer or bladder cancer.

The amount of the conjugate of the present invention added for the formulation of the composition for diagnosis of the present invention differs depending on the degree of symptoms or age of a patient, the dosage form of a preparation used, or the binding titer of the Fab fragment, etc. For example, approximately 0.001 mg/kg to 100 mg/kg based on the mass of the Fab fragment can be used per unit body weight of a patient.

Examples of the dosage form of the composition for diagnosis of the present invention can include parenteral agents such as injections and agents for drip infusion. Administration can be performed by intravenous injection, local intramuscular injection to a target tissue, subcutaneous injection, intravesical administration, or the like. For the formulation, a carrier or an additive suitable for these dosage forms can be used in a pharmaceutically acceptable range. The type of the pharmaceutically acceptable carrier or additive is not particularly limited, and a carrier or an additive well known to those skilled in the art can be used.

The present invention also relates to use of the detectable conjugate of the present invention for the production of a composition for the early diagnosis or a composition for the staging of a cancer. The present invention also relates to the detectable conjugate of the present invention for use in the early diagnosis or staging of a cancer.

Further, the present invention also relates to a method for diagnosing a cancer, comprising administering the detectable conjugate of the present invention to a subject. In this context, the "subject" is a human or any of other mammals in need of receiving the diagnosis. A certain embodiment is a human in need of receiving the diagnosis. The effective amount of the detectable conjugate of the present invention in the diagnosis method of the present invention may be the same amount as the effective amount of the conjugate of the present invention for the formulation described above. In the diagnosis method of the present invention, the detectable conjugate of the present invention is preferably administered by local intramuscular injection to a target tissue, subcutaneous injection, or the like.

In an alternative embodiment, the present invention also relates to use of the anti-human MUC1 antibody Fab fragment of the present invention for the production of the conjugate of the present invention. In a certain embodiment, the present invention also relates to use of the anti-human MUC1 antibody Fab fragment of the present invention for the production of a composition for diagnosis comprising the conjugate of the present invention.

As an embodiment in which the composition for diagnosis of the present invention comprising a metal radioisotope is provided, it may be labeled with the metal radioisotope immediately before use or may be provided as a composition for diagnosis comprising the metal radioisotope.

8. Pharmaceutical Composition and Treatment Method

The present invention includes a pharmaceutical composition comprising one or more type of conjugate of the present invention comprising a metal radioisotope such as $^{90}$Y or $^{177}$Lu, and a pharmaceutically acceptable carrier. The pharmaceutical composition of the present invention may comprise one type of conjugate of the present invention or may comprise a combination of two or more types of conjugates of the present invention. The conjugate of the present invention can be used in the preparation of the pharmaceutical composition by a method usually used using a carrier usually used in the art, i.e., a pharmaceutical excipient, a pharmaceutical carrier, or the like. Examples of the dosage forms of these pharmaceutical compositions include parenteral agents such as injections and agents for drip infusion. Administration can be performed by intravenous injection, subcutaneous injection, intravesical administration, or the like. For the formulation, an excipient, a carrier, an additive, or the like suitable for these dosage forms can be used in a pharmaceutically acceptable range.

The amount of the conjugate of the present invention added for the formulation described above differs depending on the degree of symptoms or age of a patient, the dosage form of a preparation used, or the binding titer of the Fab fragment, etc. For example, approximately 0.001 mg/kg to 100 mg/kg based on the mass of the Fab fragment can be used per unit body weight of a patient.

The pharmaceutical composition comprising the conjugate of the present invention can be used for the treatment of a cancer. The cancer expected to be able to be treated by the pharmaceutical composition comprising the conjugate of the present invention is a cancer expressing human MUC1. Examples thereof include breast cancer, lung cancer, colorectal cancer, bladder cancer, skin cancer, thyroid gland cancer, stomach cancer, pancreatic cancer, kidney cancer, ovary cancer and uterine cervical cancer.

The present invention includes a pharmaceutical composition for treating breast cancer or bladder cancer, comprising the conjugate of the present invention. The present invention also includes a method for treating breast cancer or bladder cancer, comprising the step of administering a therapeutically effective amount of the conjugate of the present invention. The present invention also includes a method for inducing the cell death of cancer cells of breast cancer or bladder cancer, comprising the step of administering a therapeutically effective amount of the conjugate of the present invention.

The pharmaceutical composition for treating a cancer can also be used in the diagnosis of a cancer. For example, the pharmaceutical composition for treating breast cancer or bladder cancer can also be used in the diagnosis of the cancer.

The present invention also includes the conjugate of the present invention for use in the treatment of breast cancer or bladder cancer. The present invention further includes use of the conjugate of the present invention for the production of a pharmaceutical composition for treating breast cancer or bladder cancer.

In an alternative embodiment, the present invention also relates to use of the anti-human MUC1 antibody Fab fragment of the present invention for the production of a pharmaceutical composition comprising the conjugate of the present invention.

The present invention is generally described above. Particular Examples will be provided here for reference in order to obtain further understanding. However, these are given for illustrative purposes and do not limit the present invention.

EXAMPLES

Example 1: Preparation of Anti-Human MUC1 Antibody Fab Fragment

Two anti-human MUC1 antibody Fab fragments designated as P10-1 Fab and P10-2 Fab were prepared.

The amino acid sequences of the heavy chain variable regions and the light chain variable regions of P10-1 Fab and P10-2 Fab were specifically designed as sequences expected to improve affinity and not to attenuate affinity even by the binding of a labeling moiety, by using a molecular model of a humanized antibody constructed in accordance with the literature (Proteins, 2014 August; 82 (8): 1624-35) after humanization of a 1B2 antibody, which is a mouse-derived anti-human cancer-specific MUC1 antibody, with reference to the method described in the literature (Front Biosci., 2008 Jan. 1; 13: 1619-33).

GS vector pEE6.4 (Lonza Ltd.) having an insert of a heavy chain fragment gene formed by connecting a gene encoding a signal sequence (MEWSWVFLFFLSVTTGVHS (SEQ ID NO: 13)) to the 5' side of each heavy chain variable region gene of P10-1 Fab or P10-2 Fab and connecting a human Igγ1 constant region gene (consisting of a nucleotide sequence from nucleotide positions 355 to 669 of SEQ ID NO: 1 or 3) to the 3' side thereof was prepared. Here, in order to express each Fab fragment, a stop codon was inserted to downstream of a codon of Asp at position 221 based on the EU index provided by Kabat et al. (corresponding to Asp at position 222 in the amino acid sequences of SEQ ID NOs: 2 and 4 mentioned later) in the heavy chain constant region gene. Also, GS vector pEE12.4 (Lonza Ltd.) having an insert of a light chain gene formed by connecting a gene encoding a signal sequence (MSVPTQVLGLLLLWLTDARC (SEQ ID NO: 14)) to the 5' side of the common light chain variable region gene of P10-1 Fab and P10-2 Fab and connecting a human κ chain constant region gene (consisting of a nucleotide sequence from nucleotide positions 340 to 660 of SEQ ID NO: 5) to the 3' side thereof was prepared.

The expression of each Fab fragment was performed by the method of transient expression. Expi293F cells (Thermo Fisher Scientific Inc.) cultured into approximately 2500000 cells/mL in Expi293 Expression Medium (Thermo Fisher Scientific Inc.) were transfected with the GS vectors of the heavy chain fragment and the light chain mentioned above using ExpiFectamine 293 Transfection Kit (Thermo Fisher Scientific Inc.), and cultured for 8 days. After expression, the culture supernatant was purified using KappaSelect (GE Healthcare Japan Corp.) to obtain each Fab fragment.

The nucleotide sequence of the heavy chain fragment of P10-1 Fab is shown in SEQ ID NO: 1, and the amino acid sequence encoded thereby is shown in SEQ ID NO: 2. The nucleotide sequence of the heavy chain variable region of P10-1 Fab is shown in SEQ ID NO: 7. The amino acid sequence encoded thereby is shown in SEQ ID NO: 8.

The nucleotide sequence of the heavy chain fragment of P10-2 Fab is shown in SEQ ID NO: 3. The amino acid sequence encoded thereby is shown in SEQ ID NO: 4. The nucleotide sequence of the heavy chain variable region of P10-2 Fab is shown in SEQ ID NO: 9. The amino acid sequence encoded thereby is shown in SEQ ID NO: 10.

The light chain is common in P10-1 Fab and P10-2 Fab. The nucleotide sequence thereof is shown in SEQ ID NO: 5. The amino acid sequence encoded thereby is shown in SEQ ID NO: 6. The nucleotide sequence of the light chain variable region of P10-1 Fab and P10-2 Fab is shown in SEQ ID NO: 11. The amino acid sequence encoded thereby is shown in SEQ ID NO: 12.

Example 2: Amino Acid Modification Analysis of Fab Fragment

As a result of analyzing the amino acid modification of purified P10-2 Fab, it was suggested that heavy chain N-terminal glutamine was modified into pyroglutamic acid in a great majority of purified antibodies.

Example 3: Preparation of Anti-Human MUC1 Antibody Fab Fragment Conjugate

In this Example, P10-2 Fab was used as the anti-human MUC1 antibody Fab fragment (Fab).

In Examples below, the number of (Y—S$_1$—X) bound to Fab of each conjugate that could be confirmed by MS analysis is shown. However, the results do not mean that conjugates having the number of the bound moiety other than the number presented are excluded. It should be understood that the possibility remains that conjugates having the number of the bound moiety whose presence cannot be confirmed in relation to the precision of MS analysis instruments are present.

Example 3-1: Synthesis of Sample No. 1 ([DFO—C(=O)-(1,3-phenylene)-C(=O)-Gly-Lys-Z$_2$]$_p$-Fab))

[Chemical Formula 10]

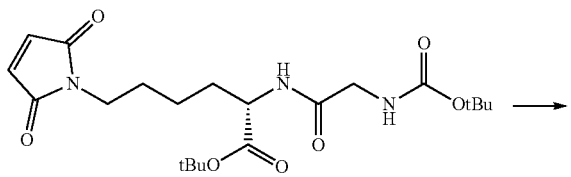

-continued

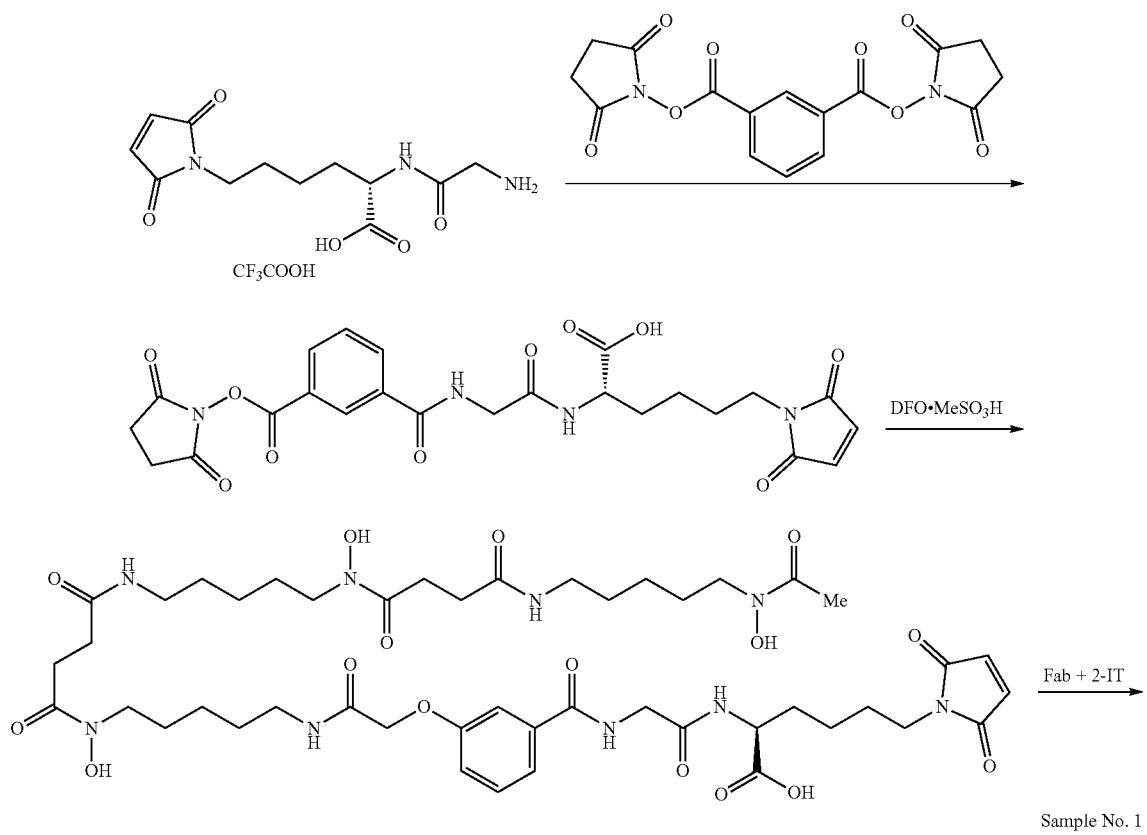

Sample No. 1

(i) Synthesis of N-(3-{[(2,5-dioxopyrrolidin-1-yl) oxy]carbonyl}benzoyl)glycyl-6-(2,5-dioxo-2,5-dihydro-1H-pyrrol-1-yl)-L-norleucine tert-Butyl N-(tert-butoxycarbonyl)glycyl-6-(2,5-dioxo-2,5-dihydro-1H-pyrrol-1-yl)-L-norleucinate (11.5 g) was dissolved in anisole (2.8 mL). To the solution, trifluoroacetic acid (hereinafter, abbreviated to TFA) (58 mL) was added dropwise at room temperature, and the resultant was stirred for 2 hours. After confirmation of the consumption of the starting material and the production of the desired compound of by HPLC, the solvent in the reaction solution was concentrated under reduced pressure. A solid precipitated by the addition of diethyl ether (200 mL) to the residue was filtered and washed with diethyl ether to obtain glycyl-6-(2,5-dioxo-2,5-dihydro-1H-pyrrol-1-yl)-L-norleucine mono(trifluoroacetate) (8.70 g). MS(ESI+); 284

Glycyl-6-(2,5-dioxo-2,5-dihydro-1H-pyrrol-1-yl)-L-norleucine mono(trifluoroacetate) (105 mg) and 1,1'-[1,3-phenylenebis(carbonyloxy)]di(pyrrolidine-2,5-dione) (272 mg) were dissolved in dimethylformamide (hereinafter, abbreviated to DMF) (3 mL). To the solution, triethylamine (hereinafter, abbreviated to TEA) (0.07 mL) was gradually added at room temperature, and the resultant was stirred for 20 minutes. After confirmation of the production of the desired compound and the consumption of the starting material by LCMS, the reaction was quenched by the addition of an aqueous TFA solution, and the pH was adjusted to around 4. The resultant was purified by reverse-phase column chromatography (YMC Triart C18, acetonitrile/0.1% aqueous TFA solution). Fractions containing the desired compound were collected, concentrated, and freeze-dried to obtain the title compound (155 mg). MS(ESI+); 529

(ii) Synthesis of N-{3-[(3,14,25-trihydroxy-2,10,13,21,24-pentaoxo-3,9,14,20,25-pentaazatriacontan-30-yl)carbamoyl]benzoyl}glycyl-6-(2,5-dioxo-2,5-dihydro-1H-pyrrol-1-yl)-L-norleucine N-(3-{[(2,5-Dioxopyrrolidin-1-yl)oxy]carbonyl}benzoyl)glycyl-6-(2,5-dioxo-2,5-dihydro-1H-pyrrol-1-yl)-L-norleucine (141 mg) was dissolved in DMF (5 mL). To the solution, $N^4$-{5-[acetyl(hydroxy)amino]pentyl}-$N^1$-(5-{4-[(5-aminopentyl)(hydroxy)amino]-4-oxobutanamido}pentyl)-$N^1$-hydroxybutanediamide monomethanesulfonate (177 mg) and TEA (0.075 mL) were added at room temperature. The starting material was poorly soluble and caused white turbidity, and was therefore dissolved by the addition of dimethyl sulfoxide (hereinafter, abbreviated to DMSO) (5 mL), and the resultant was stirred at room temperature for 1 hour. After confirmation of the production of the desired compound and the consumption of the starting material by LCMS, the reaction was quenched by the addition of an aqueous TFA solution, and the pH was adjusted to around 5. The resultant was purified by reverse-phase column chromatography (YMC Triart C18, acetonitrile/0.1% aqueous TFA solution). Fractions containing the desired compound were collected, concentrated, and dried under reduced pressure for 2 hours to obtain the title compound (150 mg). MS(ESI+); 975

(iii) Purification of N-{3-[(3,14,25-trihydroxy-2,10,13,21,24-pentaoxo-3,9,14,20,25-pentaazatriacontan-30-yl)carbamoyl]benzoyl}glycyl-6-(2,5-dioxo-2,5-dihydro-1H-pyrrol-1-yl)-L-norleucine N-{3-[(3,14,25-Trihydroxy-2,10,13,21,24-pentaoxo-3,9,14,20,25-pentaazatriacontan-30-yl)carbamoyl]benzoyl}glycyl-6-(2,5-dioxo-2,5-dihydro-1H-pyrrol-1-yl)-L-norleucine (122 mg) was dissolved in DMSO (8 mL) and DMF (4 mL). The solution was purified by reverse-phase column chromatography (YMC Triart C18, acetonitrile/0.1% aqueous TFA solution). Fractions containing the compound of interest were collected, concentrated, and dried under reduced pressure for 2 hours to obtain the title compound (19 mg). MS(ESI−); 973

(iv) Synthesis of Sample No. 1

To a Fab solution prepared at 4 mg/mL with a 0.1 M borate buffer solution, a 2-iminothiolane (2-IT) solution prepared with a 0.1 M borate buffer solution was added, and the resultant was incubated at 37° C. for 30 minutes. An excess of 2-IT was washed three repetitive times with EDTA-containing phosphate-buffered saline (pH 6.0) using Amicon Ultra-0.5 mL centrifugal filter (Merck Millipore), and finally concentrated and filtered.

To the obtained filtrate, N-{3-[(3,14,25-trihydroxy-2,10,13,21,24-pentaoxo-3,9,14,20,25-pentaazatriacontan-30-yl)carbamoyl]benzoyl}glycyl-6-(2,5-dioxo-2,5-dihydro-1H-pyrrol-1-yl)-L-norleucine diluted with a 0.1 M borate buffer solution (pH 8.5) and then dissolved in DMF was added, and the resultant was incubated at 37° C. for 2 hours. An excess of the reagent was washed (which was repeated three times) with EDTA-containing phosphate-buffered saline (pH 6.0) using Amicon Ultra-0.5 mL centrifugal filter, and finally concentrated and filtered.

Subsequently, to the obtained supernatant, a 2-iodoacetamide solution prepared at 10 mg/mL with phosphate-buffered saline (pH 6.0) was added, and then, the resultant was incubated at 37° C. for 30 minutes. An excess of iodoacetamide was washed three repetitive times with phosphate-buffered saline (pH 7.0) using Amicon Ultra-0.5 mL centrifugal filter, and finally concentrated and filtered to obtain a conjugate containing bound Fab. The conjugate was confirmed by MS analysis to be a mixture of a conjugate containing one molecule of [DFO—C(=O)-(1,3-phenylene)-C(=O)-Gly-Lys-$Z_2$] (molecular weight: 1076) bound to one Fab (molecular weight: 47.5 kDa), and a conjugate containing two molecules thereof bound.

Example 3-2: Synthesis of Sample No. 2 ([DFO—C(=O)—CH$_2$O-(1,3-phenylene)-C(=O)-Gly-Lys-$Z_2$]$_p$-Fab)

[Chemical Formula 11]

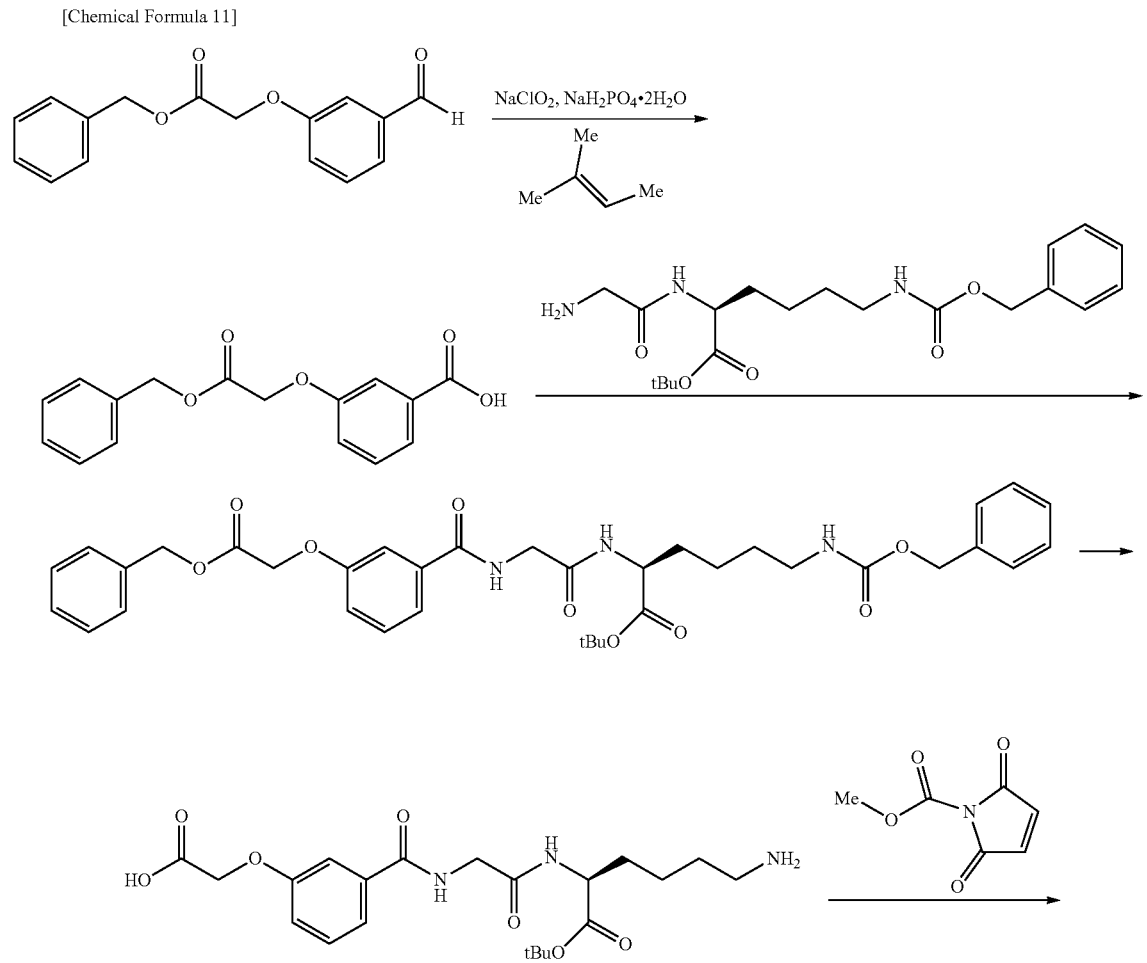

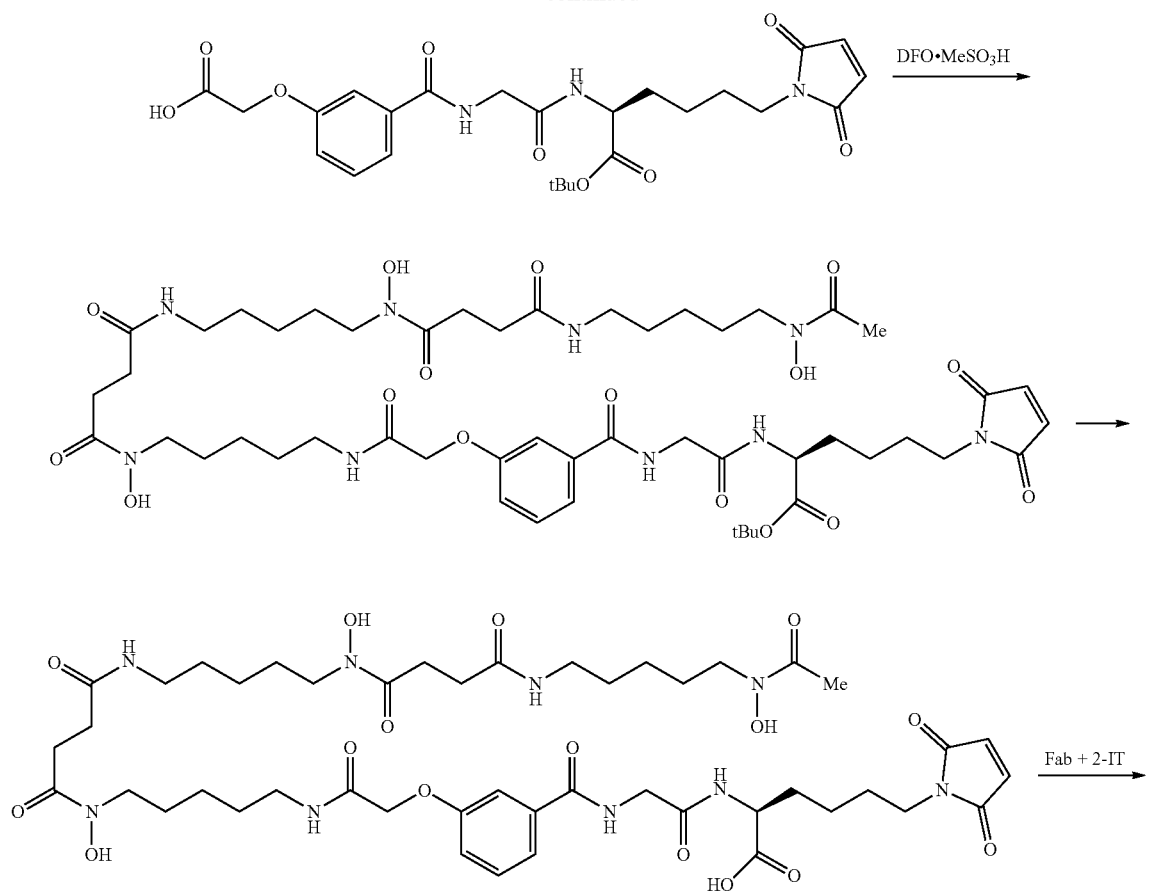

Sample No. 2

(i) Synthesis of 3-[(2-(benzyloxy)-2-oxoethoxy] benzoic acid

To a mixture of benzyl (3-formylphenoxy)acetate (2.90 g) (Chemistry, 2015 Aug. 24; 21 (35): 12421-30), 2-methylpropan-2-ol (60 mL) and water (30 mL), 2-methylbut-2-ene (6 mL), sodium dihydrogen phosphate hydrate (1:1:2) (3.35 g) and sodium chlorite (3.64 g) were added at room temperature, and the resultant was stirred for 2 hours. To the reaction solution, ethyl acetate and 1 M hydrochloric acid (60 mL) were added, followed by extraction with ethyl acetate. The organic layer was washed with water and a saturated aqueous solution of sodium chloride, dried over anhydrous magnesium sulfate, and filtered. The filtrate was concentrated to obtain the title compound (2.93 g). MS(ESI−); 285

(ii) Synthesis of tert-Butyl N-{3-[2-(benzyloxy)-2-oxoethoxy]benzoyl}glycyl-N⁶-[(benzyloxy)carbonyl]-L-Lysinate To a mixture of tert-Butyl glycyl-N⁶-[(benzyloxy)carbonyl]-L-lysinate (760 mg), 3-[2-(benzyloxy)-2-oxoethoxy]benzoic acid (600 mg) and DMF (10 mL), 1-(Dimethylamino)-N,N-dimethyl-1-[(3H-[1,2,3]triazolo[4,5-b]pyridin-3-yl)oxy]methaniminium hexafluoridophosphate(1-) (800 mg) and diisopropylethylamine (hereinafter, abbreviated to DIPEA) (1 mL) were added under ice cooling. After stirring at room temperature for 1 hour, water and ethyl acetate were added to the mixture to separate an organic layer. Then, an aqueous layer was extracted with ethyl acetate. Combined organic layers were washed with water and a saturated aqueous solution of sodium chloride, then dried over anhydrous sodium sulfate, and filtered. The filtrate was concentrated, and then, the residue was purified by silica gel chromatography (hexane/ethyl acetate=90/10-0/100) to obtain the title compound (1.19 g). MS(ESI+); 662

(iii) Synthesis of tert-Butyl N-[3-(carboxymethoxy) benzoyl]glycyl-L-Lysinate

To a mixture of tert-Butyl N-{3-[2-(benzyloxy)-2-oxoethoxy]benzoyl}glycyl-N⁶-[(benzyloxy)carbonyl]-L-lysinate (1.18 g) and ethyl alcohol (20 mL), 10% palladium-supported carbon (containing 50% water, 200 mg) was added at room temperature. The mixture was stirred overnight at room temperature under hydrogen atmosphere (1 atm). The mixture was filtered through celite and then concentrated to obtain the title compound (804 mg). MS(ESI+); 438

(iv) Synthesis of tert-Butyl N-[3-(carboxymethoxy) benzoyl]glycyl-6-(2,5-dioxo-2,5-dihydro-1H-pyrrol-1-yl)-L-norleucinate To a mixture of tert-Butyl N-[3-(carboxymethoxy)benzoyl]glycyl-L-lysinate (600 mg), DMF (2 mL) and tetrahydrofuran (4 mL), Methyl 2,5-dioxo-2,5-dihydro-1H-pyrrole-1-carboxylate (350 mg) and DIPEA (700 μL) were added at room temperature, and the resultant was heated and stirred at 60° C. After 9 hours, DIPEA (500 μL) was further added thereto, and the resultant was further stirred overnight at 60° C. The resultant was allowed to cool to room temperature, neutralized with TFA (600 μL), concentrated under reduced pressure, and directly purified by reverse-phase column chromatography (YMC Triart C18, acetonitrile/0.1% aqueous TFA solution). A fraction of the desired compound was concentrated under reduced pressure, and water and ethyl acetate were added to the residue for layer separation and extraction. The organic layer was dried over anhydrous magnesium sulfate and filtered, and then, the filtrate was concentrated under reduced pressure and dried to obtain the title compound (378 mg). MS(ESI+); 518

(v) Synthesis of tert-Butyl N-{3-[(9,20,31-trihydroxy-2,10,13,21,24,32-hexaoxo-3,9,14,20,25,31-hexaazatritriacontan-1-yl)oxy]benzoyl}glycyl-6-(2,5-dioxo-2,5-dihydro-1H-pyrrol-1-yl)-L-norleucinate To a mixture of $N^4$-{5-[acetyl(hydroxy)amino]pentyl}-$N^1$-(5-{4-[(5-aminopentyl)(hydroxy)amino]-4-oxobutanamido}pentyl)-$N^1$-hydroxybutanediamide monomethanesulfonate (400 mg), tert-Butyl N-[3-(carboxymethoxy)benzoyl]glycyl-6-(2,5-dioxo-2,5-dihydro-1H-pyrrol-1-yl)-L-norleucinate (365 mg) and DMF (4 mL), 3-{[(ethylimino)methylidene]amino}-N,N-dimethylpropan-1-amine monohydrochloride (hereinafter, abbreviated to EDC HCl) (240 mg), 1H-benzotriazol-1-ol (hereinafter, abbreviated to HOBτ) (165 mg) and DIPEA (500 μL) were added under ice cooling, and the resultant was stirred overnight at room temperature. The reaction mixture was diluted with a mixed solution of TFA (200 μL) and water (500 μL) and directly purified by reverse-phase column chromatography (YMC Triart C18, acetonitrile/0.1% aqueous TFA solution). Fractions of the desired compound were collected, concentrated under reduced pressure, and freeze-dried to obtain the title compound (285 mg). MS(ESI−); 1059

(vi) Synthesis of N-{3-[(9,20,31-trihydroxy-2,10,13,21,24,32-hexaoxo-3,9,14,20,25,31-hexaazatritriacontan-1-yl)oxy]benzoyl}glycyl-6-(2,5-dioxo-2,5-dihydro-1H-pyrrol-1-yl)-L-norleucine To tert-Butyl N-{3-[(9,20,31-trihydroxy-2,10,13,21,24,32-hexaoxo-3,9,14,20,25,31-hexaazatritriacontan-1-yl)oxy]benzoyl}glycyl-6-(2,5-dioxo-2,5-dihydro-1H-pyrrol-1-yl)-L-norleucinate (370 mg), TFA (1.5 mL) was added under ice cooling, and the resultant was stirred overnight at room temperature. After concentration under reduced pressure, the residue was diluted with DMF (4 mL) and water (500 μL) and directly purified by reverse-phase column chromatography (YMC Triart C18, acetonitrile/0.1% aqueous TFA solution). Fractions of the desired compound were collected, concentrated under reduced pressure, and freeze-dried to obtain the title compound (194 mg). MS(ESI−); 1003

(vii) Synthesis of Sample No. 2

A conjugate was obtained in the same manner as in (iv) of Example 3-1 using the compound of (vi). The conjugate was confirmed by MS analysis to be a mixture of a conjugate containing one molecule of [DFO—C(=O)—CH$_2$O-(1,3-phenylene)-C(=O)-Gly-Lys-$Z_2$] (molecular weight: 1106) bound to one Fab (molecular weight: 47.5 kDa), and a conjugate containing two molecules thereof bound.

Example 3-3: Synthesis of Sample No. 3 ([DOTA-CH$_2$-(1,4-phenylene)-NH—C(=S)]p-Fab)

[Chemical Formula 12]

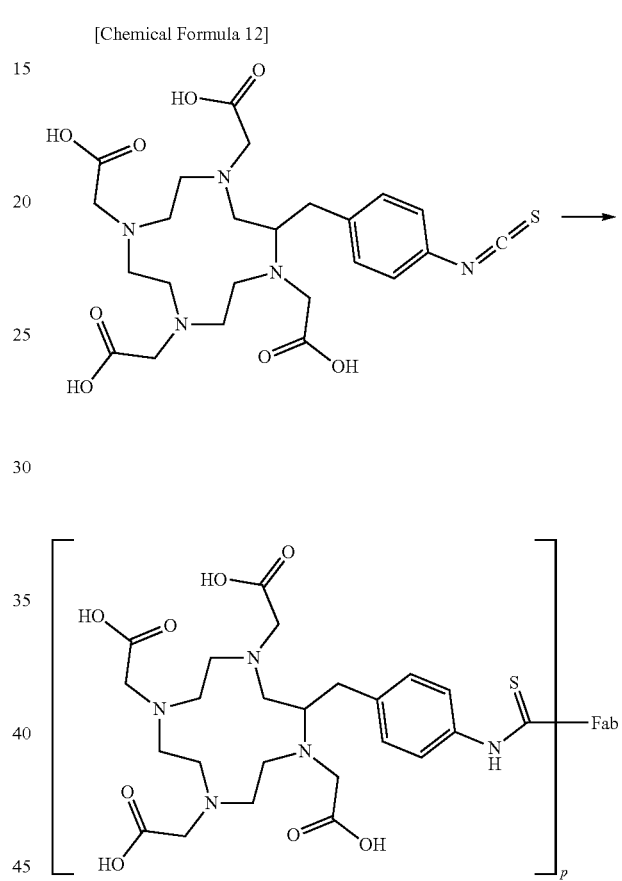

p-SCN-Bn-DOTA (Macrocyclics, Inc.) was used to bind the chelating agent DOTA to Fab. To a Fab solution, phosphate-buffered saline (pH 7.4) and glycerin were added, and finally a 0.1 M sodium carbonate solution (pH 9.0) was added to prepare a 6 mg/mL solution in sodium carbonate having pH of 8.8 to 9.0. p-SCN-Bn-DOTA was added thereto, and the resultant was incubated at 37° C. for 2 hours. After reaction, the conjugate was recovered and purified through Amicon Ultra-0.5 mL centrifugal filter. The conjugate was confirmed by MS analysis to be a mixture of a conjugate containing one molecule of [DOTA-CH$_2$-(1,4-phenylene)-NH—C(=S)] (molecular weight: 553) bound to one Fab (molecular weight: 47.5 kDa), a conjugate containing two molecules thereof bound, a conjugate containing three molecules thereof bound, and a conjugate containing four molecules thereof bound.

Example 3-4: Synthesis of Sample No. 4 ([DOTA]p-Fab))

[Chemical Formula 13]

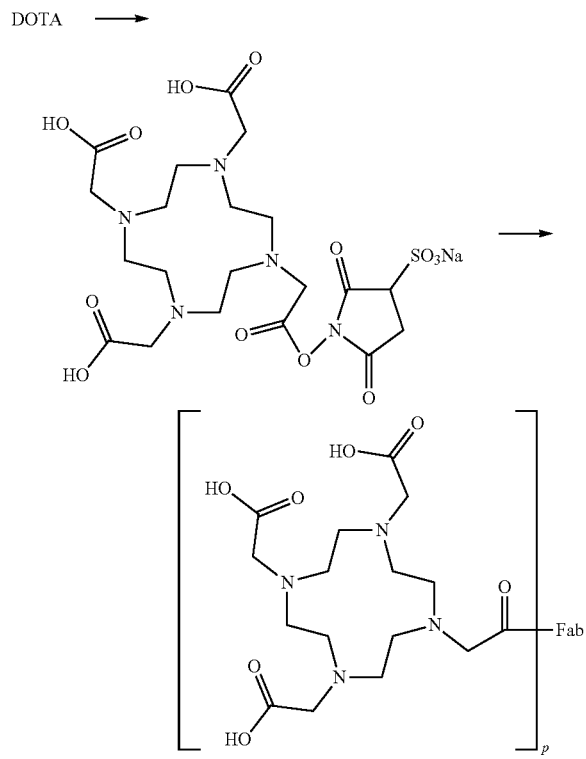

A mixed solution of 2,2',2'',2'''-(1,4,7,10-tetraazacyclodo-decane-1,4,7,10-tetrayl)tetraacetic acid (DOTA) (16 mg) and water (810 μL) was pH-adjusted to 6 by the addition of a 1 M aqueous sodium hydroxide solution (80 μL) under ice cooling. To the prepared solution (239 μL), sodium 1-hydroxy-2,5-dioxopyrrolidine-3-sulfonate (2.3 mg) dissolved in water (117 μL) was added under ice cooling. Then, an aqueous EDC HCl solution (8.3 μL, 25 mg/mL) was added thereto, and the resultant was stirred for 30 minutes under ice cooling to prepare a N-hydroxysulfosuccinimidyl DOTA solution. Before addition to Fab, the pH of the solution was adjusted to 7 by the addition of a 0.2 M disodium hydrogen phosphate solution (pH 9) (40 μL).

To a 0.1 M disodium hydrogen phosphate solution (198 μL) of 20.8 mg/mL Fab (27 μL), the prepared N-hydroxysulfosuccinimidyl DOTA solution (100 μL) was added, and the resultant was incubated at 37° C. for 20 hours. The resultant was washed two repetitive times with a 10 mM phosphate buffer solution (pH 7.0) using Amicon Ultra, washed with a 0.3 M ammonium acetate buffer solution, and finally concentrated and filtered to obtain a conjugate. The conjugate was confirmed by MS analysis to be a mixture of a conjugate containing one molecule of DOTA (molecular weight: 387) bound to one Fab (molecular weight: 47.5 kDa), and a conjugate containing two molecules thereof bound.

Example 3-5. Synthesis of Sample No. 5 ([DOTA-Gly-Lys-$Z_2$]p-Fab)

[Chemical Formula 14]

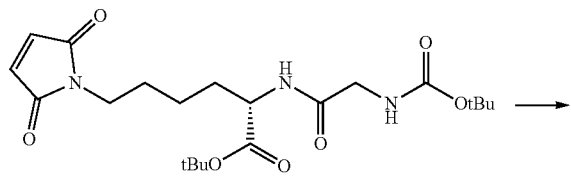

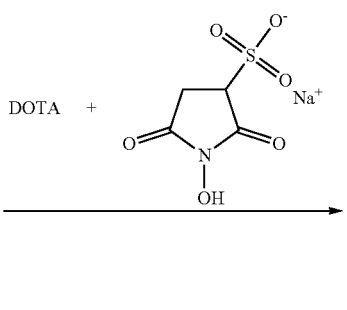

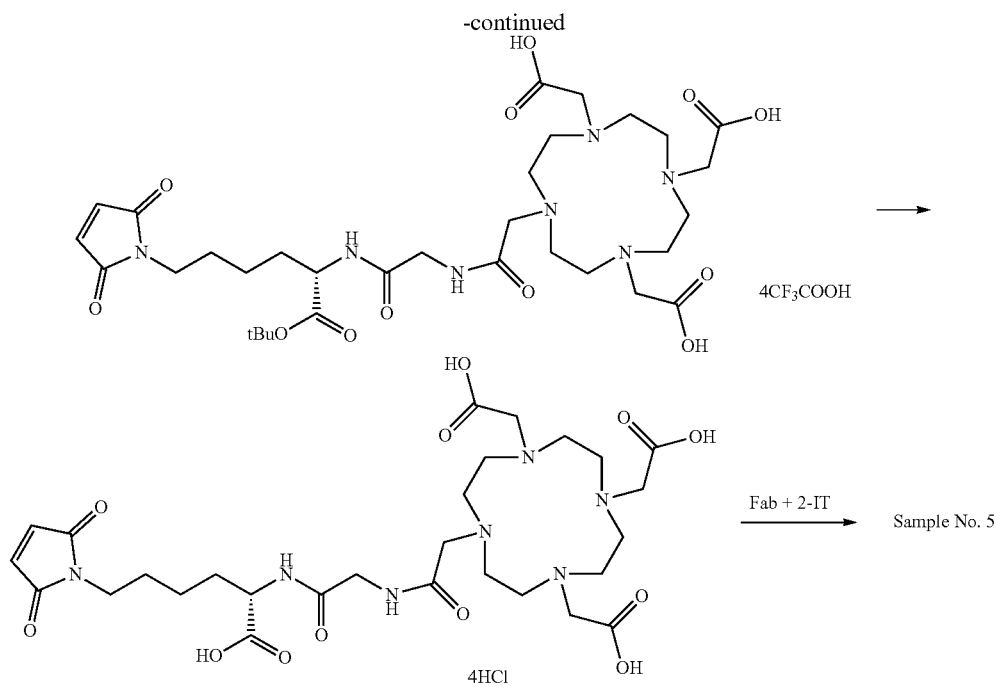

(i) Synthesis of tert-Butyl N-{[4,7,10-tris(carboxymethyl)-1,4,7,10-tetraazacyclododecan-1-yl]acetyl}glycyl-6-(2,5-dioxo-2,5-dihydro-1H-pyrrol-1-yl)-L-norleucinate tetrakis(trifluoroacetate)

To a solution of tert-Butyl N-(tert-butoxycarbonyl)glycyl-6-(2,5-dioxo-2,5-dihydro-1H-pyrrol-1-yl)-L-norleucinate (1 g) in dichloromethane (12 mL), TFA (6 mL) was added under ice cooling, and the resultant was stirred for 2 hours under ice cooling. The reaction solution was concentrated under reduced pressure to obtain tert-Butyl glycyl-6-(2,5-dioxo-2,5-dihydro-1H-pyrrol-1-yl)-L-norleucinate mono(trifluoroacetate) (1.1 g). MS(ESI+); 340.3

A mixture of 2,2',2'',2'''-(1,4,7,10-tetraazacyclododecane-1,4,7,10-tetrayl)tetraacetic acid (320 mg) and water (12 mL) was pH-adjusted to 6 by the addition of a 1 M aqueous sodium hydroxide solution (1.58 mL) under ice cooling. Then, sodium 1-hydroxy-2,5-dioxopyrrolidine-3-sulfonate (170 mg) and EDC HCl (150 mg) were added under ice cooling, and the resultant was stirred for 30 minutes. The pH was adjusted to 7 by the addition of a 0.2 M disodium hydrogen phosphate solution (pH 9) (3 mL), and then adjusted to 8 by the addition of tert-Butyl glycyl-6-(2,5-dioxo-2,5-dihydro-1H-pyrrol-1-yl)-L-norleucinate mono(trifluoroacetate) (750 mg), a 1 M aqueous sodium hydroxide solution (672 µL) and a 0.2 M disodium hydrogen phosphate solution (pH 9) (800 µL), and the resultant was stirred for 2 hours under ice cooling. The resultant was purified by reverse-phase silica gel column chromatography (solvent gradient; 0→100% acetonitrile/water (0.05% aqueous TFA solution)) to obtain the title compound (347 mg). MS(ESI−): 726.3

(ii) Synthesis of N-{[4,7,10-tris(carboxymethyl)-1,4,7,10-tetraazacyclododecan-1-yl]acetyl}glycyl-6-(2,5-dioxo-2,5-dihydro-1H-pyrrol-1-yl)-L-norleucine tetrahydrochloride A mixed solution of tert-Butyl N-{[4,7,10-tris(carboxymethyl)-1,4,7,10-tetraazacyclododecan-1-yl]acetyl}glycyl-6-(2,5-dioxo-2,5-dihydro-1H-pyrrol-1-yl)-L-norleucinate tetrakis(trifluoroacetate) (347 mg) in 4 M hydrogen chloride/dioxane (3 mL) and dichloromethane (3 mL) was stirred at room temperature for 3 hours, and then, the reaction solution was concentrated under reduced pressure. The residue was purified by reverse-phase silica gel column chromatography (solvent gradient; 0→100% acetonitrile/water (0.05% aqueous TFA solution)) to obtain the title compound (168 mg). MS(ESI+): 670

(iii) Synthesis of Sample No. 5

To 5.2 mg/mL Fab in a borate buffer solution (100 µL), 2 mg/mL 2-IT in a 0.1 M borate buffer solution (3.33 µL) was added, and the resultant was incubated at 37° C. for 30 minutes. An excess of 2-IT was washed three repetitive times with EDTA-containing 0.1 M phosphate-buffered saline (pH 6.0) using Amicon Ultra-0.5 mL centrifugal filter, and finally concentrated and filtered.

To the obtained filtrate, 25 mg/mL novel linker (DMF solution, 20 µL) was added, and the resultant was diluted into 70 µL with a 0.1 M borate buffer solution (pH 8.5) and incubated at 37° C. or 2 hours. The resultant was washed two repetitive times with EDTA-containing 0.1 M phosphate-buffered saline (pH 6.0) using Amicon Ultra-0.5 mL centrifugal filter, washed with phosphate-buffered saline (pH 7.0), and finally concentrated and filtered to obtain a conjugate.

The conjugate was confirmed by MS analysis to be a mixture of a conjugate containing one molecule of [DOTA-Gly-Lys-$Z_2$] (molecular weight: 772) bound to one Fab (molecular weight: 47.5 kDa), and a conjugate containing two molecules thereof bound.

Example 3-6. Synthesis of Sample No. 6 ([DOTA-NH—CH$_2$-(1,3-phenylene)-C(=O)-Gly-Lys-Z$_2$]p-Fab)
[Chemical Formula 15]
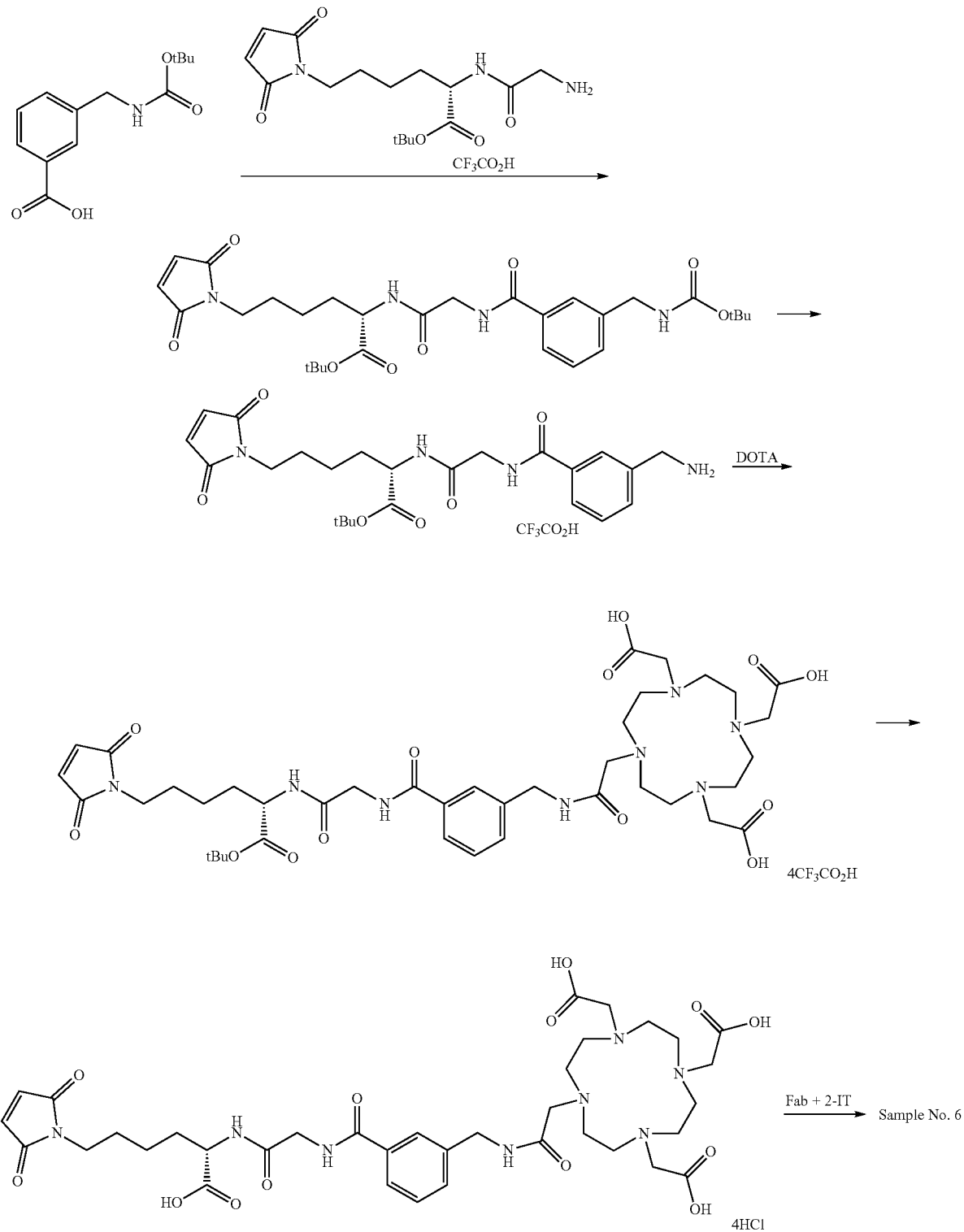

(i) Synthesis of tert-Butyl N-(3-{[(tert-butoxycarbonyl)amino]methyl}benzoyl)glycyl-6-(2,5-dioxo-2,5-dihydro-1H-pyrrol-1-yl)-L-norleucinate To a mixture of 3-{[(tert-butoxycarbonyl)amino]methyl}benzoic acid (460 mg), tert-Butyl glycyl-6-(2,5-dioxo-2,5-dihydro-1H-pyrrol-1-yl)-L-norleucinate mono(trifluoroacetate) (750 mg) and dichloromethane (15 mL), EDC HCl (380 mg), HOBt (110 mg) and TEA (700 µL) were added, and the resultant was stirred at room temperature for 15 hours. The reaction solution was concentrated, and then, the residue was purified by silica gel column chromatography (developing solvent; ethyl acetate) to obtain the title compound (478 mg). MS(ESI+): 595

(ii) Synthesis of tert-Butyl N-[3-(aminomethyl)benzoyl]glycyl-6-(2,5-dioxo-2,5-dihydro-1H-pyrrol-1-yl)-L-norleucinate mono(trifluoroacetate)

A mixture of tert-Butyl N-(3-{[(tert-butoxycarbonyl)amino]methyl}benzoyl)glycyl-6-(2,5-dioxo-2,5-dihydro-1H-pyrrol-1-yl)-L-norleucinate (478 mg) in TFA (1.5 mL) and dichloromethane (3 mL) was stirred at room temperature for 30 minutes. The reaction solution was concentrated under reduced pressure to obtain the title compound (500 mg). MS(ESI+): 473

(iii) Synthesis of tert-Butyl N-[3-({2-[4,7,10-tris(carboxymethyl)-1,4,7,10-tetraazacyclododecan-1-yl]acetamido}methyl)benzoyl]glycyl-6-(2,5-dioxo-2,5-dihydro-1H-pyrrol-1-yl)-L-norleucinate tetrakis(trifluoroacetate)

The title compound (160 mg) was obtained in the same manner as in step (i) of Example 3-5 using tert-Butyl N-[3-(aminomethyl)benzoyl]glycyl-6-(2,5-dioxo-2,5-dihydro-1H-pyrrol-1-yl)-L-norleucinate mono(trifluoroacetate) (489 mg). MS(ESI−): 857

(iv) Synthesis of N-[3-({2-[4,7,10-tris(carboxymethyl)-1,4,7,10-tetraazacyclododecan-1-yl]acetamido}methyl)benzoyl]glycyl-6-(2,5-dioxo-2,5-dihydro-1-H-pyrrol-1-yl)-L-norleucine tetrahydrochloride The title compound (80 mg) was obtained in the same manner as in step (ii) of Example 3-5 using tert-Butyl N-[3-({2-[4,7,10-tris(carboxymethyl)-1,4,7,10-tetraazacyclododecan-1-yl]acetamido}methyl)benzoyl]glycyl-6-(2,5-dioxo-2,5-dihydro-1H-pyrrol-1-yl)-L-norleucinate tetrakis(trifluoroacetate (160 mg). MS(ESI+): 803

(v) Synthesis of Sample No. 6

A conjugate was obtained in the same manner as in step (iii) of Example 3-5 using the compound of (iv) The conjugate was confirmed by MS analysis to be a mixture of a conjugate containing one molecule of [DOTA-NH—CH$_2$-(1,3-phenylene)-C(=O)-Gly-Lys-Z$_2$] (molecular weight: 905) bound to one Fab (molecular weight, 47.5 kDa), a conjugate containing two molecules thereof bound, and a conjugate containing three molecules thereof bound.

Example 3-7. Synthesis of Sample No. 7 ([DOTA-Met-Ile-NH—(CH$_2$)$_2$—Z$_1$]p-Fab)

[Chemical Formula 16]

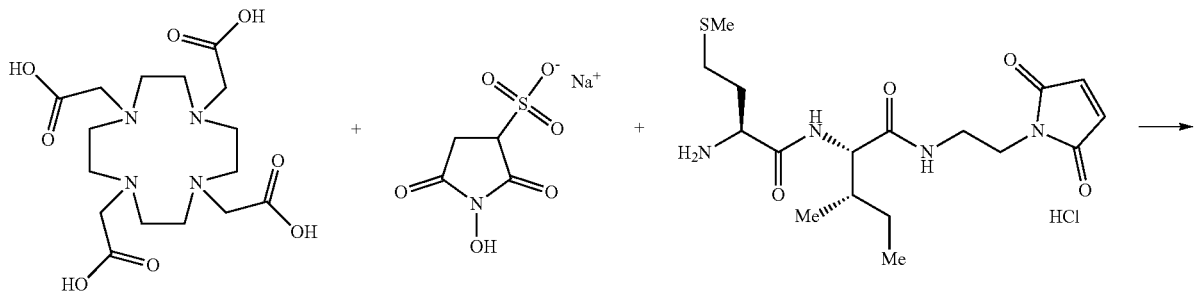

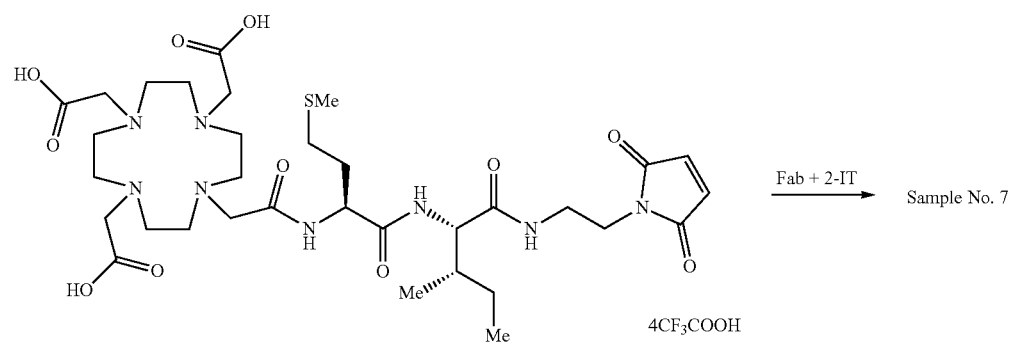

(i) Synthesis of N-{[4,7,10-Tris(carboxymethyl)-1,4,7,10-tetraazacyclododecan-1-yl]acetyl}-L-methionyl-$N^1$—[2-(2,5-dioxo-2,5-dihydro-1H-pyrrol-1-yl)ethyl]-L-isoleucinamide tetrakis(trifluoroacetate)

A mixture of 2,2',2'',2'''-(1,4,7,10-tetraazacyclododecane-1,4,7,10-tetrayl)tetraacetic acid (330 mg) and water (16 mL) was pH-adjusted to 6 by the addition of a 1 M aqueous sodium hydroxide solution (1.6 mL) under ice cooling. Then, sodium 1-hydroxy-2,5-dioxopyrrolidine-3-sulfonate (90 mg) and EDC HCl (80 mg) were added thereto under ice cooling, and the resultant was stirred for 30 minutes. The pH was adjusted to 7 by the addition of a 0.2 M disodium hydrogen phosphate solution (pH 9) (3 mL), and then adjusted to approximately 8 by the addition of L-methionyl-$N^1$-[2-(2,5-dioxo-2,5-dihydro-1H-pyrrol-1-yl)ethyl]-L-isoleucinamide monohydrochloride (100 mg) (Bioconjug Chem. 2014 Nov. 19; 25 (11): 2038-45) and a 1 M aqueous sodium hydroxide solution (570 µL), and the resultant was stirred for 2 hours under ice cooling. The resultant was purified by reverse-phase silica gel column chromatography (acetonitrile/0.05% aqueous TFA solution) to obtain the title compound (98 mg). MS(ESI−): 769

(ii) Synthesis of Sample No. 7

A conjugate was obtained in the same manner as in step (iii) of Example 3-5 using the compound of (i). The conjugate was confirmed by MS analysis to be a mixture of a conjugate containing one molecule of [DOTA-Met-Ile-NH—$(CH_2)_2$—$Z_1$] (molecular weight: 873) bound to one Fab (molecular weight: 47.5 kDa), a conjugate containing two molecules thereof bound, and a conjugate containing three molecules thereof bound.

Compounds of Production Example Nos. A1 to A19 shown in Tables 1-1 to 1-4 were synthesized according to the synthesis schemes described later by use of methods similar to those of Examples described above or methods known to those skilled in the art.

TABLE 1-1

| No. | Structure | MS |
|---|---|---|
| A1 | 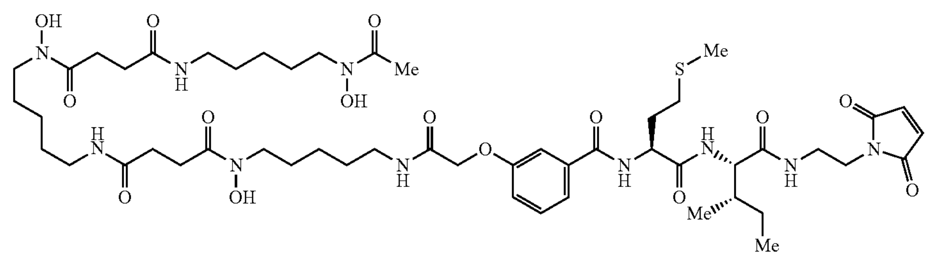 [SMILES: CC[C@H](C)[C@H](NC(=O)[C@H](CCSC)NC(=O)c1cccc(OCC(=O)NCCCCCN(O)C(=O)CCC(=O)NCCCCCN(O)C(=O)CCC(=O)NCCCCCN(O)C(C)=O)c1)C(=O)NCCN1C(=O)C=CC1=O] | ESI−; 1104 |
| A2 | 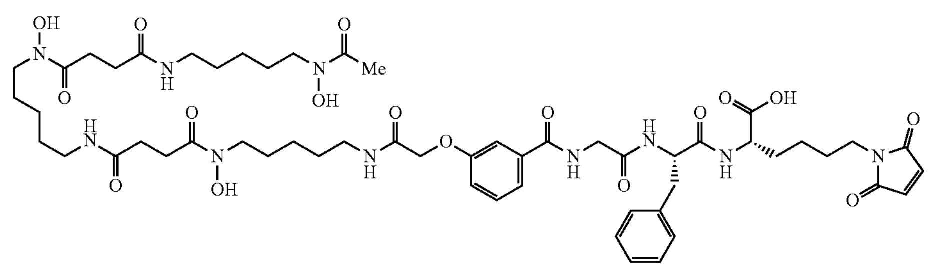 [SMILES: CC(=O)N(O)CCCCCNC(=O)CCC(=O)N(O)CCCCCNC(=O)CCC(=O)N(O)CCCCCNC(=O)COc1cccc(C(=O)NCC(=O)N[C@@H](Cc2ccccc2)C(=O)N[C@@H](CCCCN2C(=O)C=CC2=O)C(=O)O)c1] | ESI−; 1150 |
| A3 | 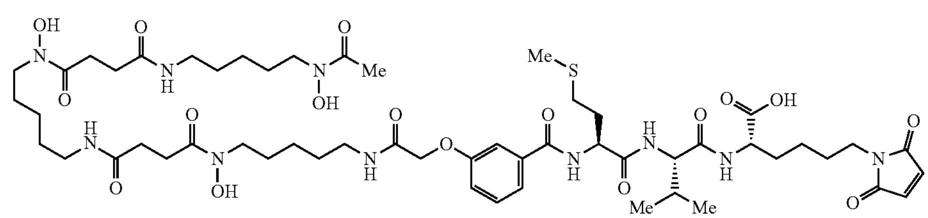 [SMILES: CSCC[C@H](NC(=O)c1cccc(OCC(=O)NCCCCCN(O)C(=O)CCC(=O)NCCCCCN(O)C(=O)CCC(=O)NCCCCCN(O)C(C)=O)c1)C(=O)N[C@H](C(=O)N[C@@H](CCCCN1C(=O)C=CC1=O)C(=O)O)C(C)C] | ESI+; 1178 |
| A4 | 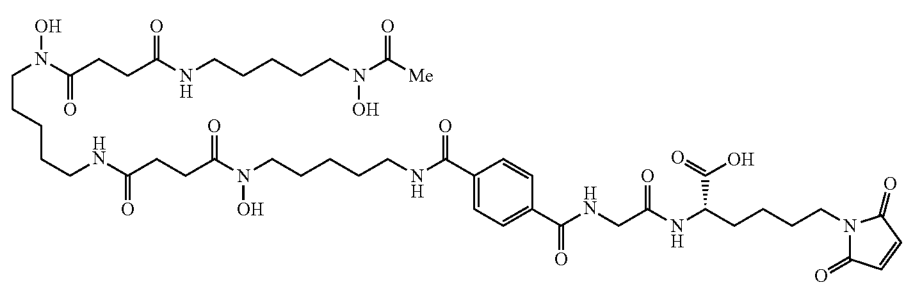 [SMILES: CC(=O)N(O)CCCCCNC(=O)CCC(=O)N(O)CCCCCNC(=O)CCC(=O)N(O)CCCCCNC(=O)c1ccc(C(=O)NCC(=O)N[C@@H](CCCCN2C(=O)C=CC2=O)C(=O)O)cc1] | ESI−; 973 |

TABLE 1-1-continued

| No. | Structure | MS |
|---|---|---|
| A5 | (structure) | ESI−; 1115 |
| A6 | (structure) | ESI+; 1218 |

TABLE 1-2

| | | |
|---|---|---|
| A7 | (structure) | ESI+; 1037 |
| A8 | (structure) | ESI−; 1074 |
| A9 | (structure) | ESI−; 1074 |
| A10 | (structure) | ESI−; 1138 |

TABLE 1-2-continued

| | | |
|---|---|---|
| A11 | (structure) | ESI−; 1136 |
| A12 | (structure) | ESI−; 1250 |

TABLE 1-3

| | | |
|---|---|---|
| A13 | (structure) | ESI+; 927 |
| A14 | (structure) | ESI−; 1131 |
| A15 | (structure) | ESI−; 1159 |

TABLE 1-3-continued

| A16 | (structure) | ESI−; 1026 |
| A17 | (structure) | ESI−; 1149 |
| A18 | (structure) | ESI−; 973 |

TABLE 1-4

| A19 | (structure, 4CF₃CO₂H) | ESI−; 739 |

(Synthesis scheme)
[Chemical Formula 17]
Production Example No. A1
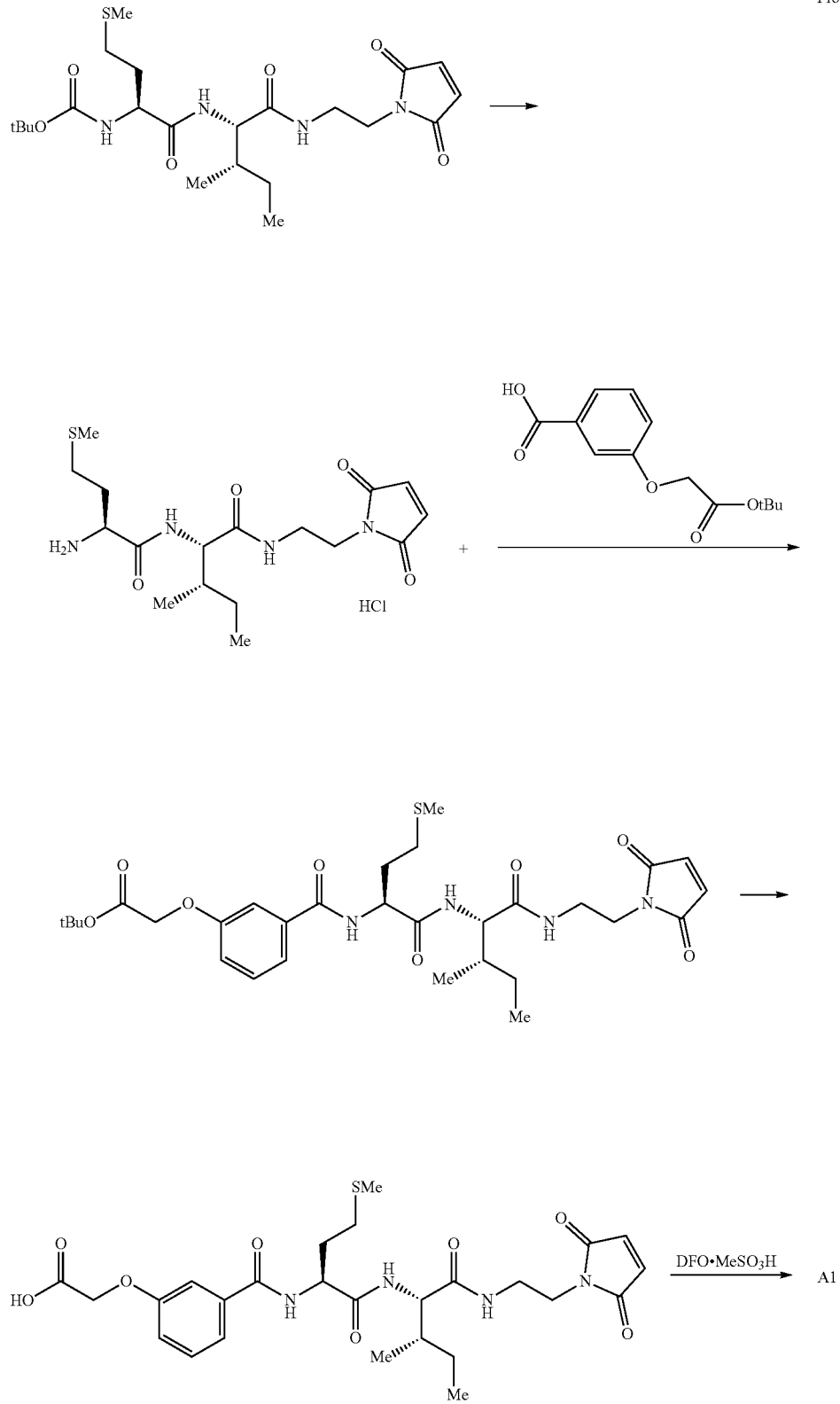

[Chemical Formula 18]
Production Example No. A2
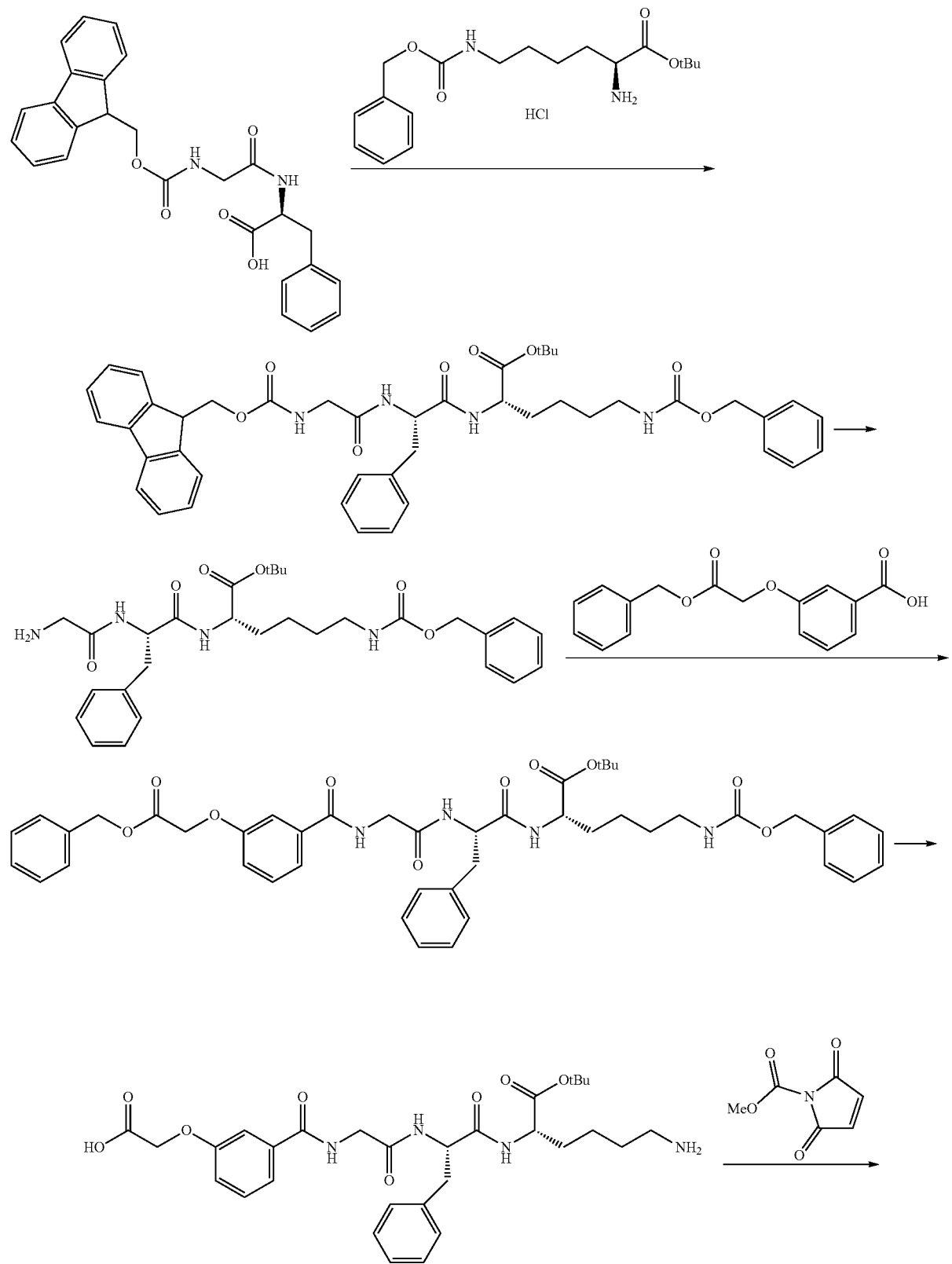

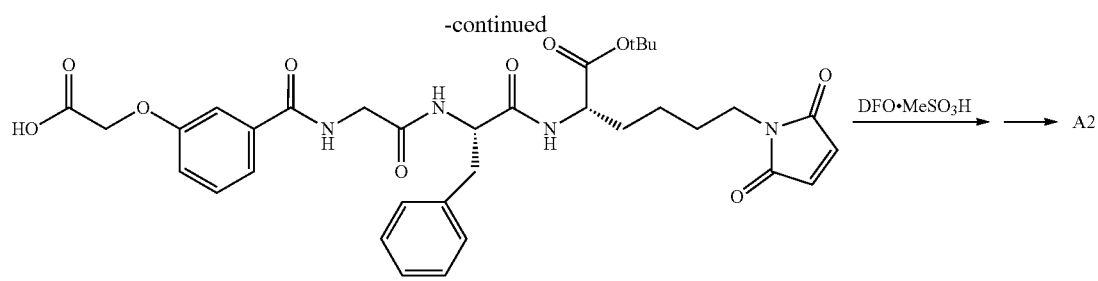
[Chemical Formula 19]
Production Example No. A3
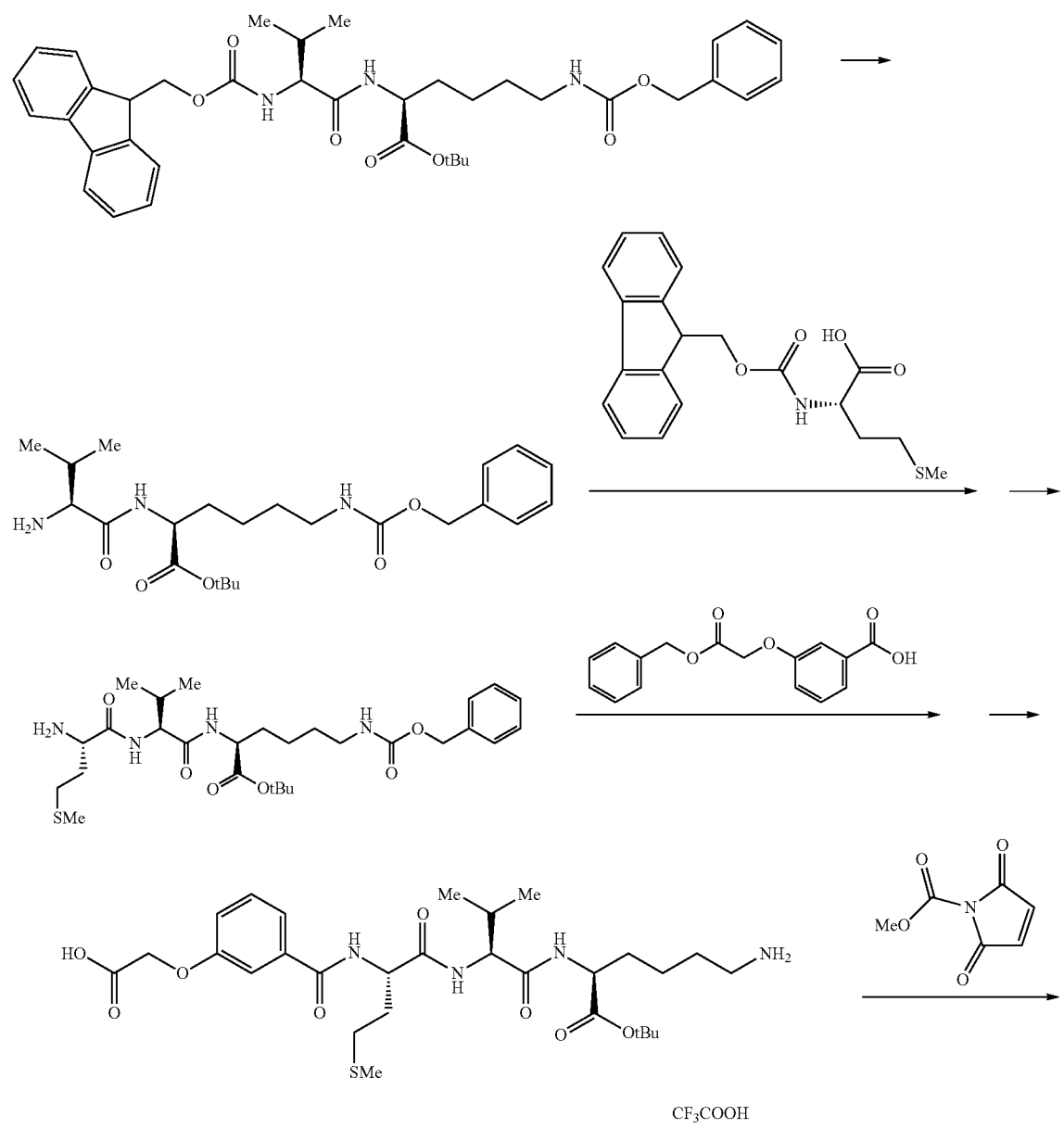

-continued
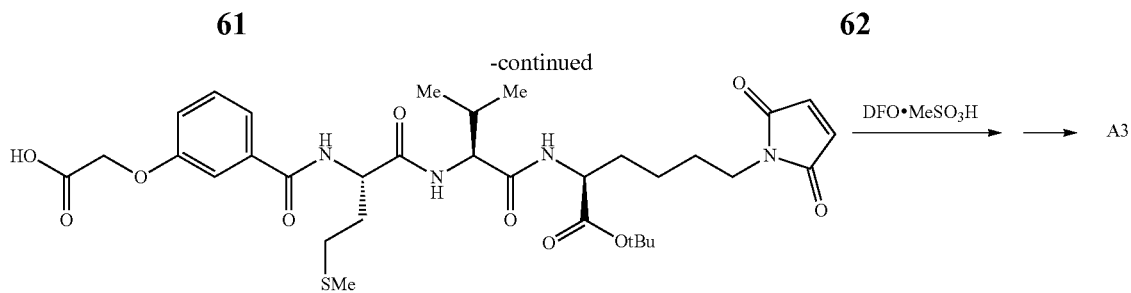
[Chemical Formula 20]
Production Example No. A4
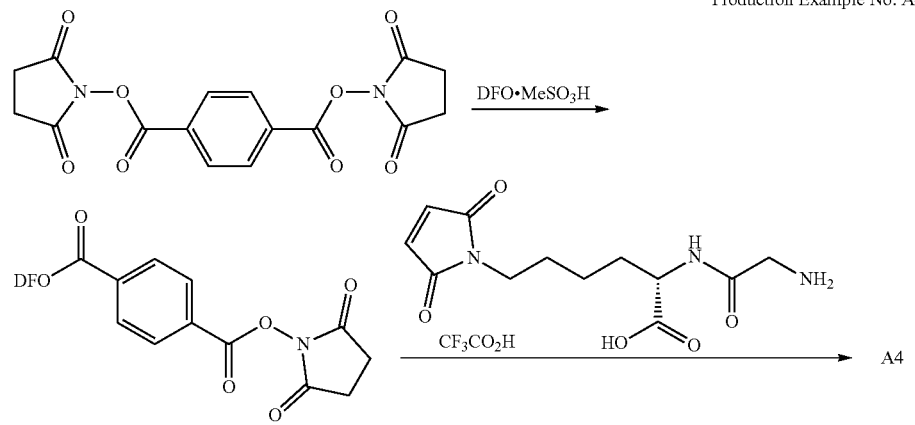
[Chemical Formula 21]
Production Example No. A5
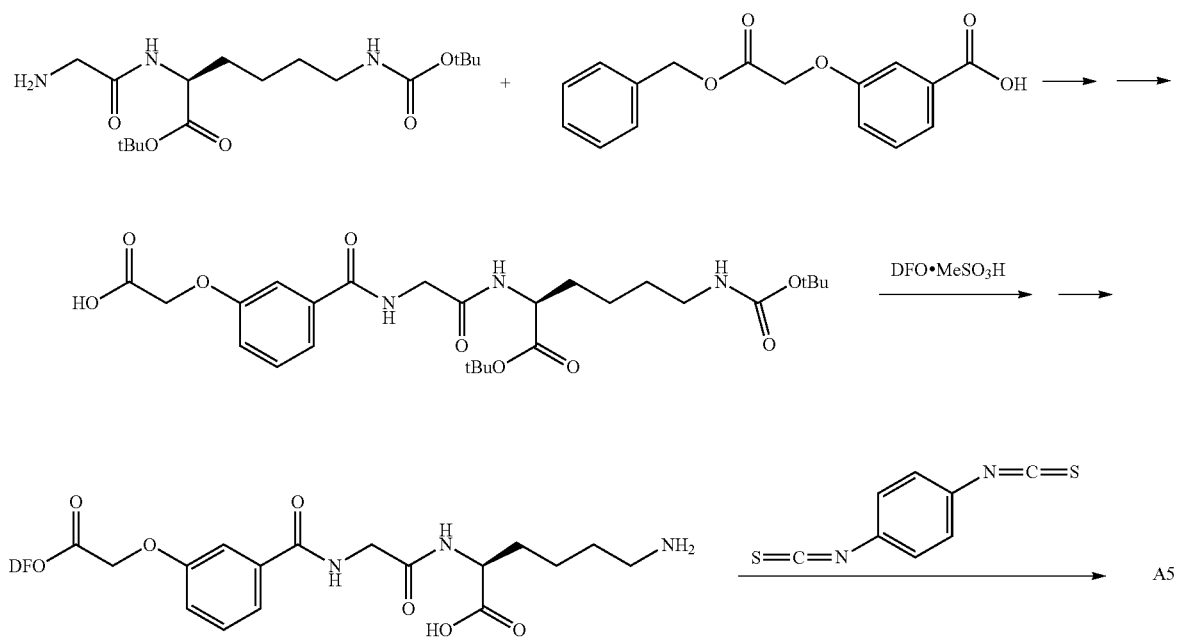

[Chemical Formula 22]
Production Example No. A6
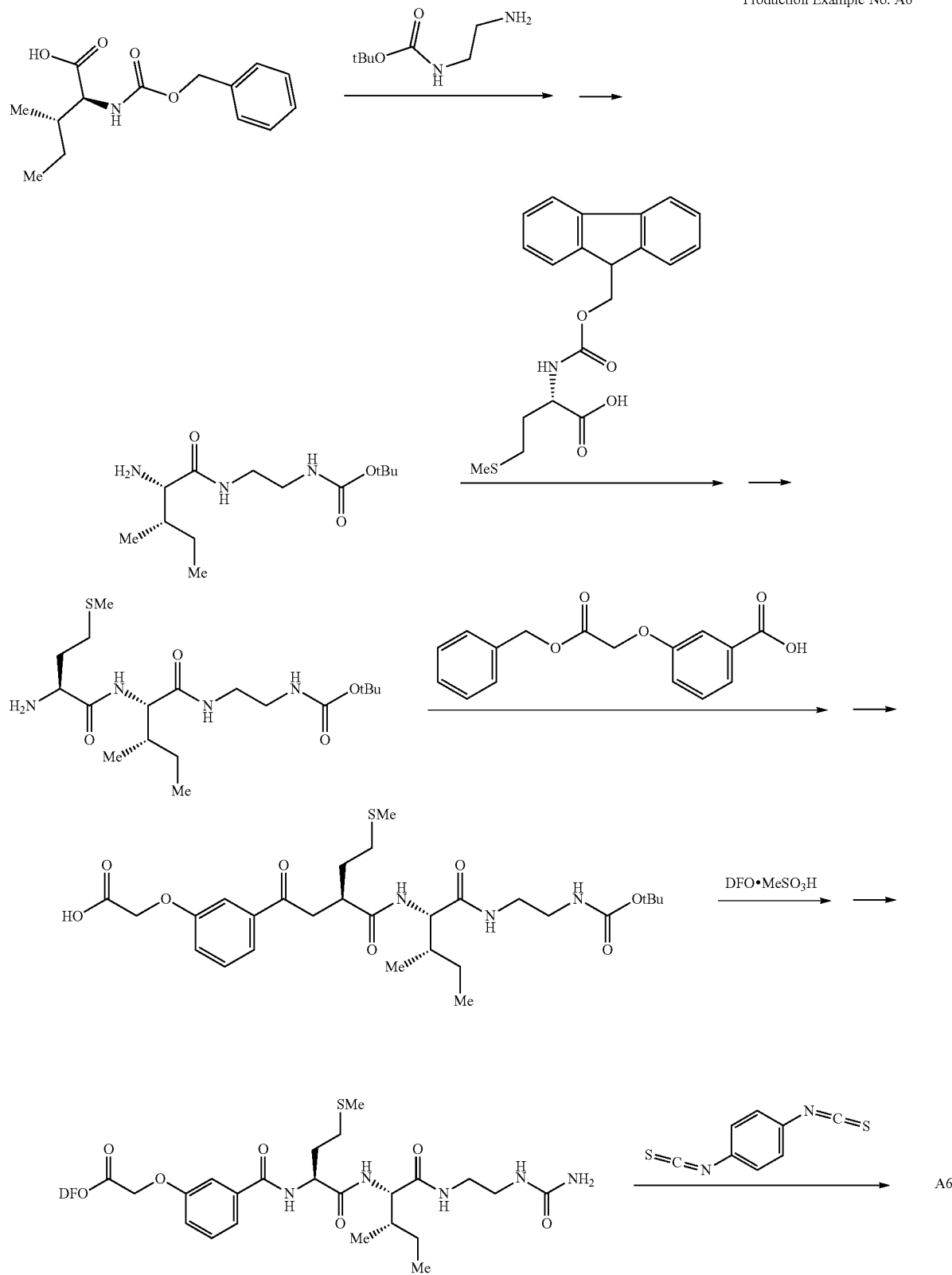

[Chemical Formula 23]
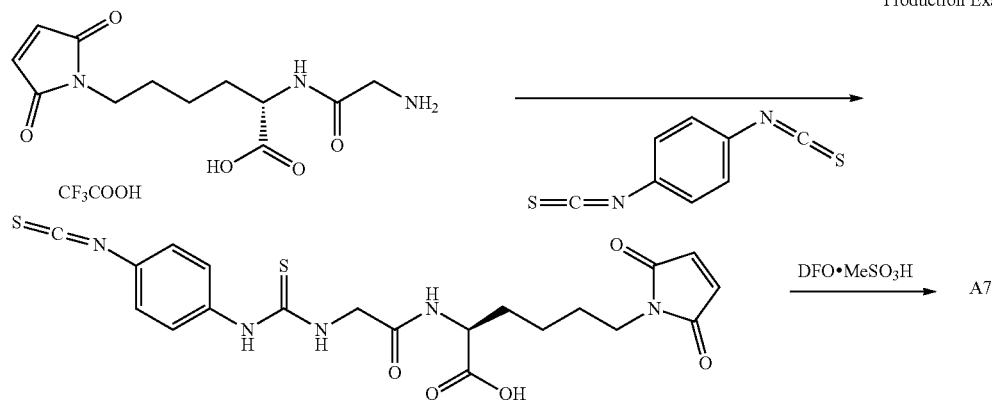
Production Example No. A7
[Chemical Formula 24]
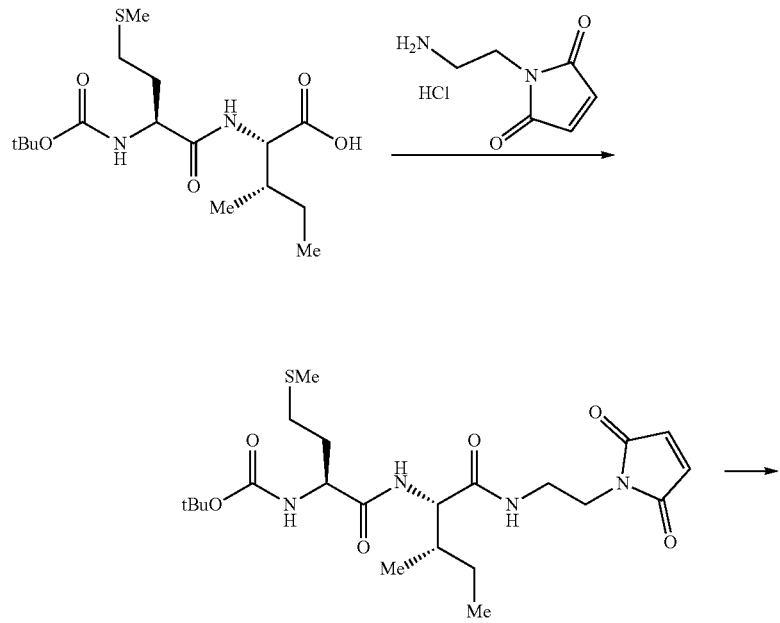
Production Example No. A8
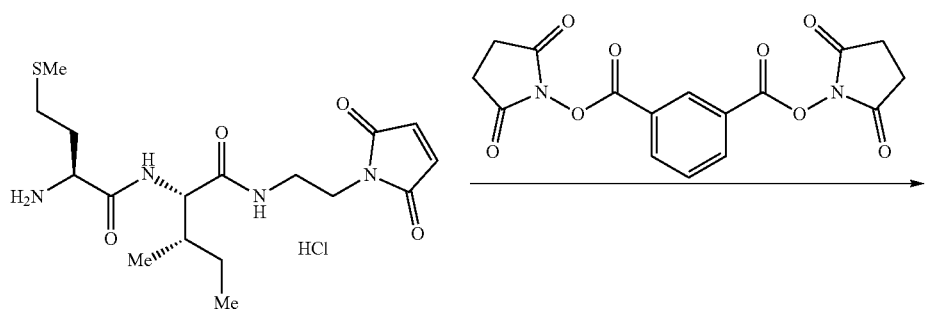

-continued
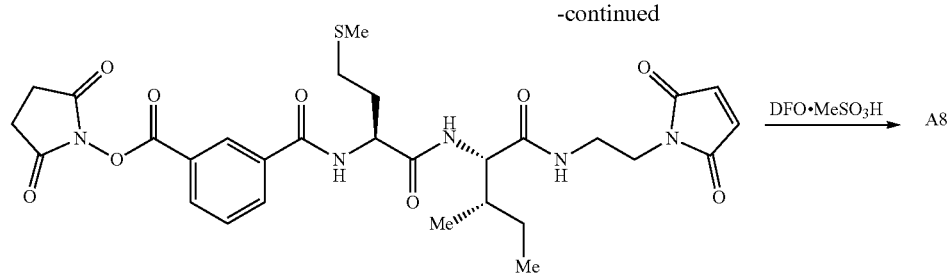
[Chemical Formula 25]
Production Example No. A9
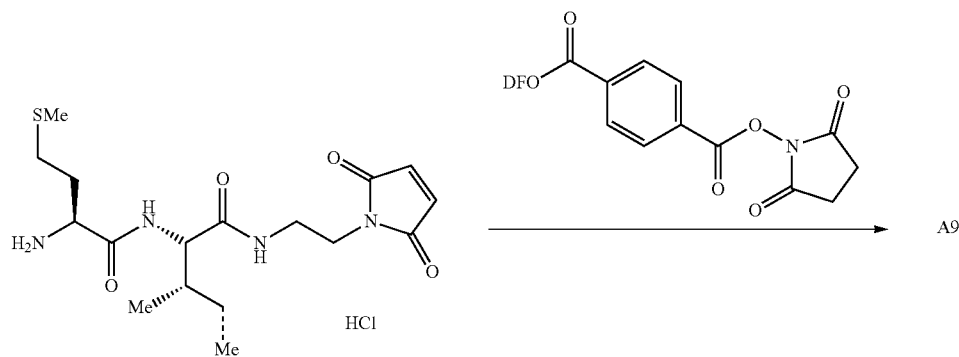
[Chemical Formula 26]
Production Example No. A10
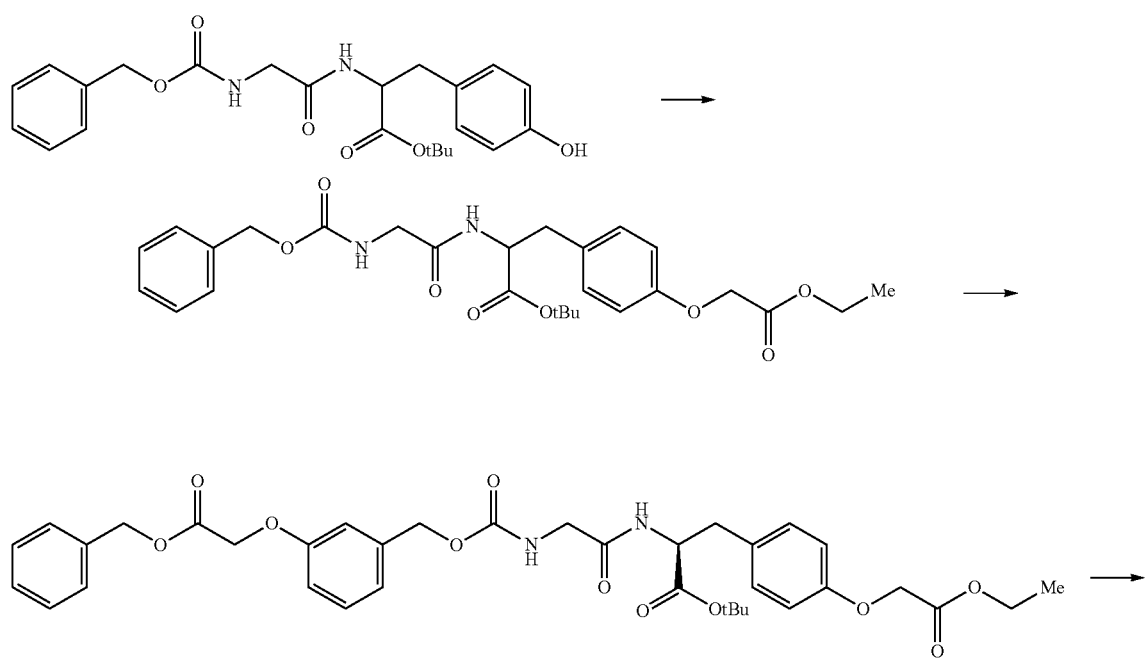

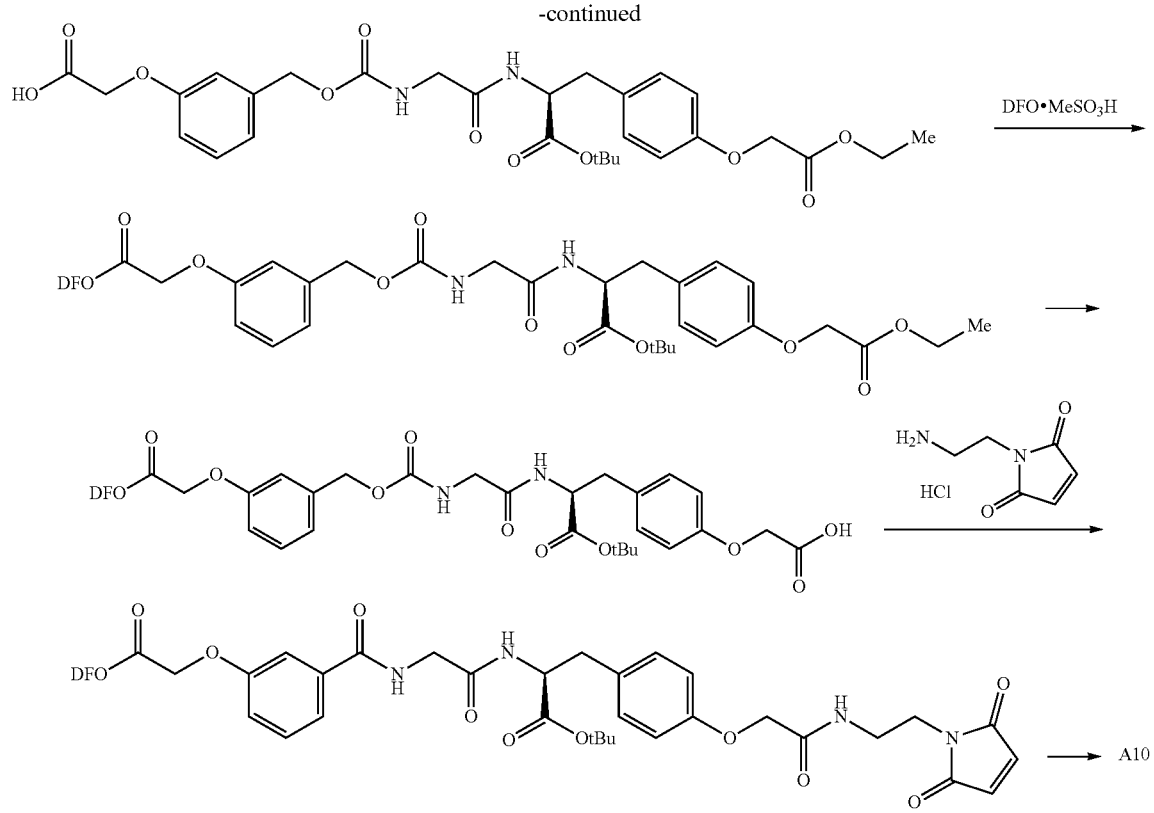
[Chemical Formula 27]
Production Example No. A11
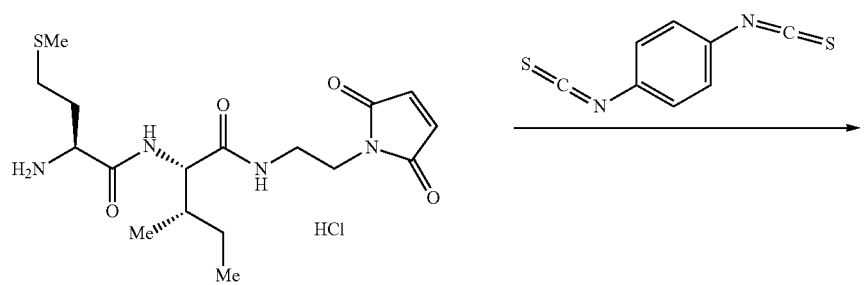
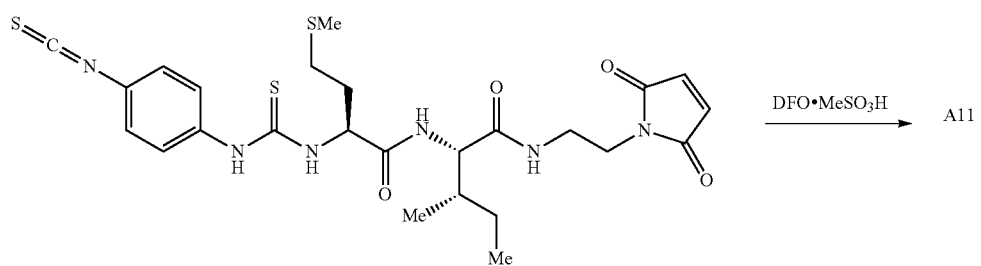

[Chemical Formula 28]
Production Example No. A12
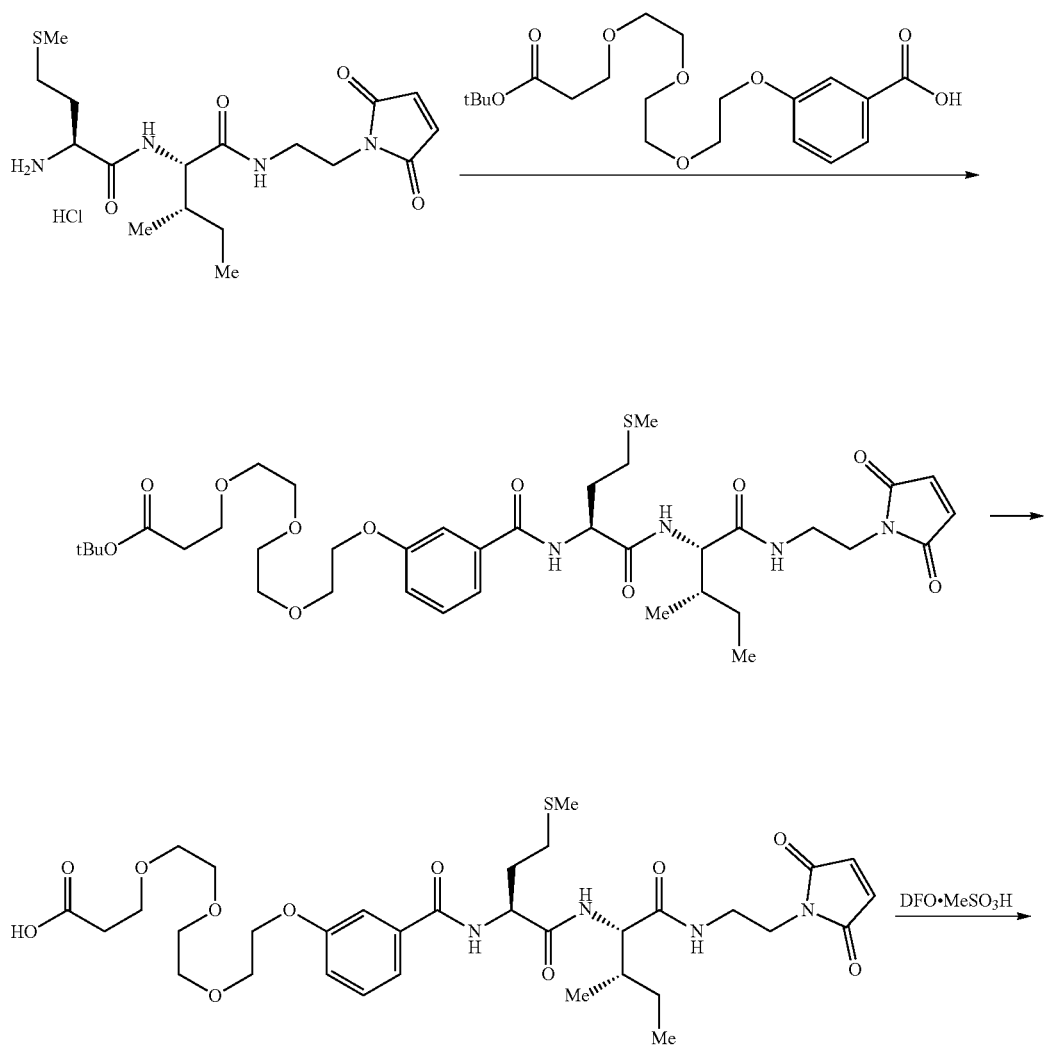
[Chemical Formula 29]
Production Example No. A13
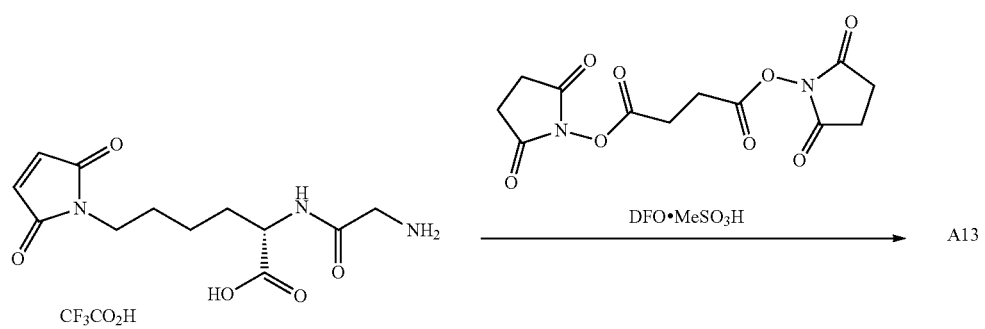

[Chemical Formula 30]
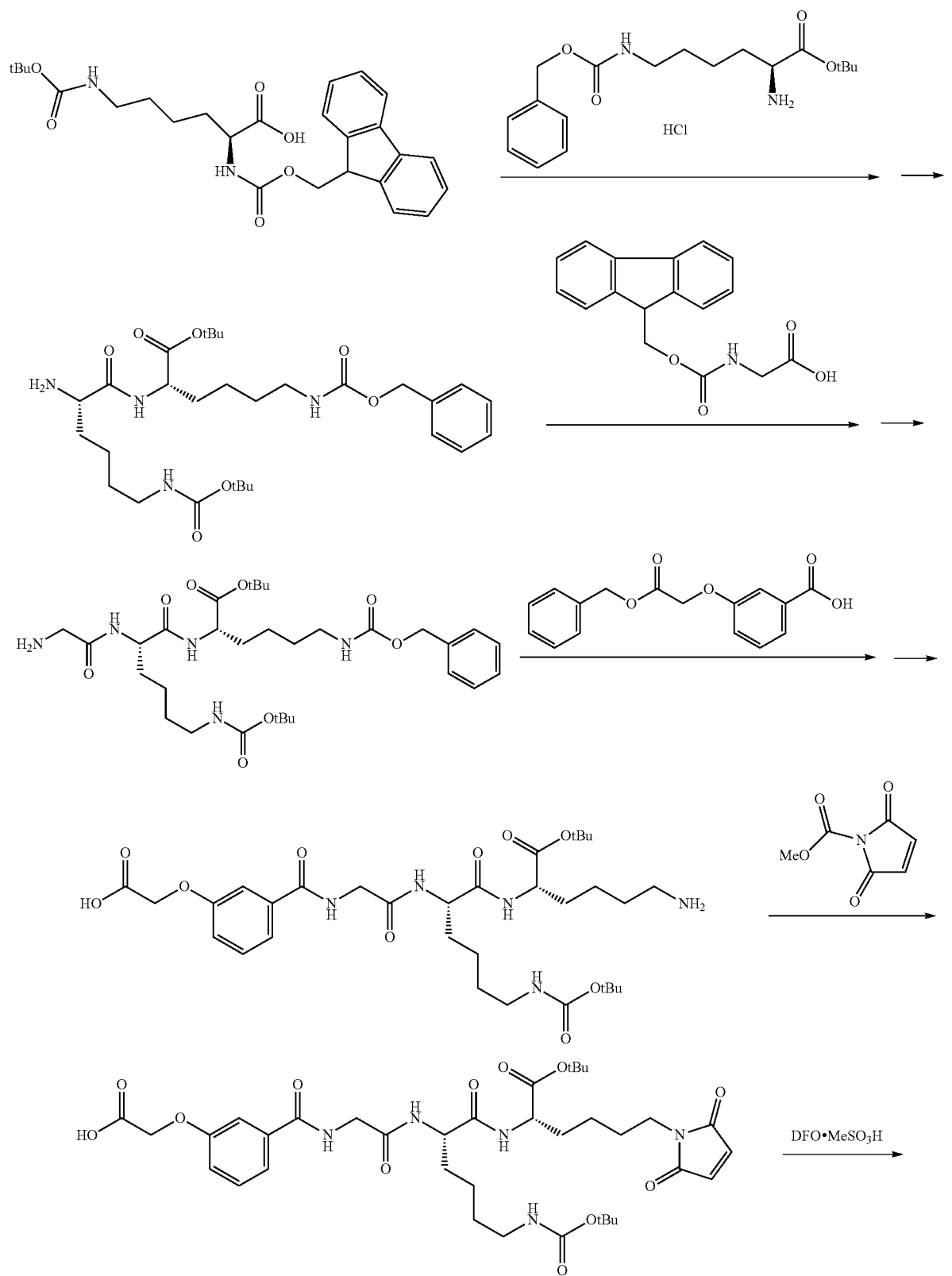
Production Example No. A14

-continued
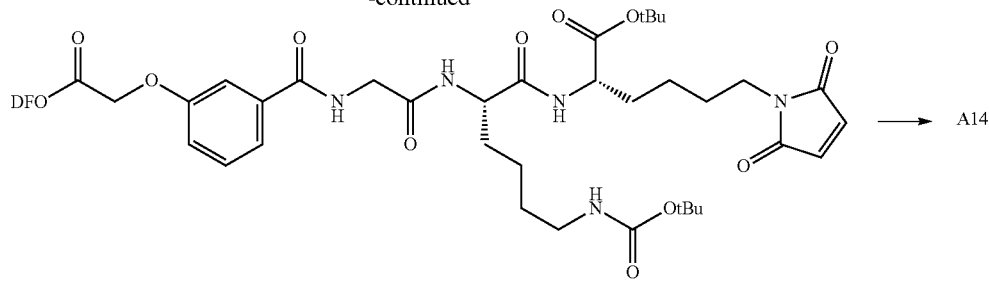
→ A14
[Chemical Formula 31]
Production Example No. A15
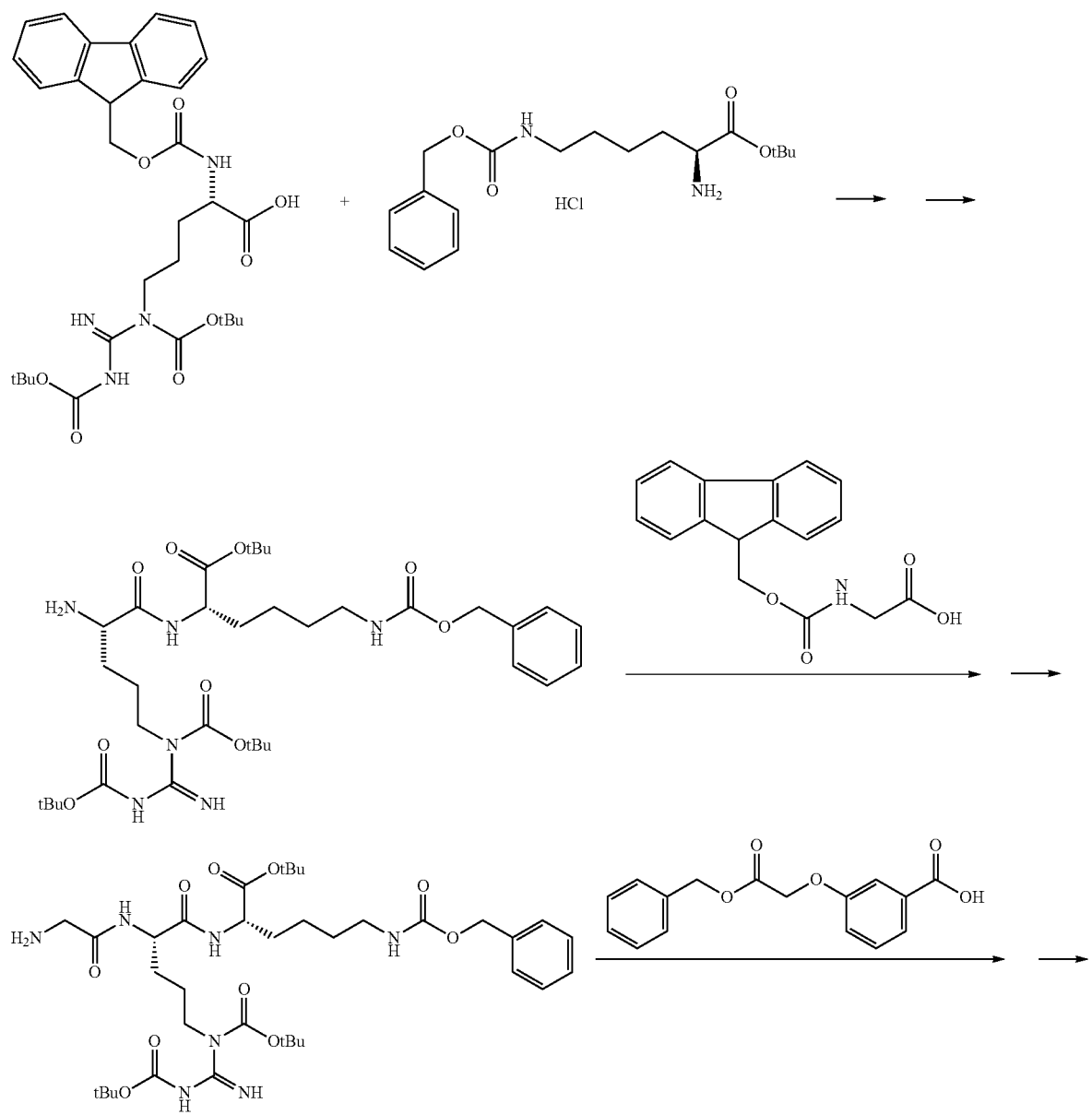

77 78
-continued
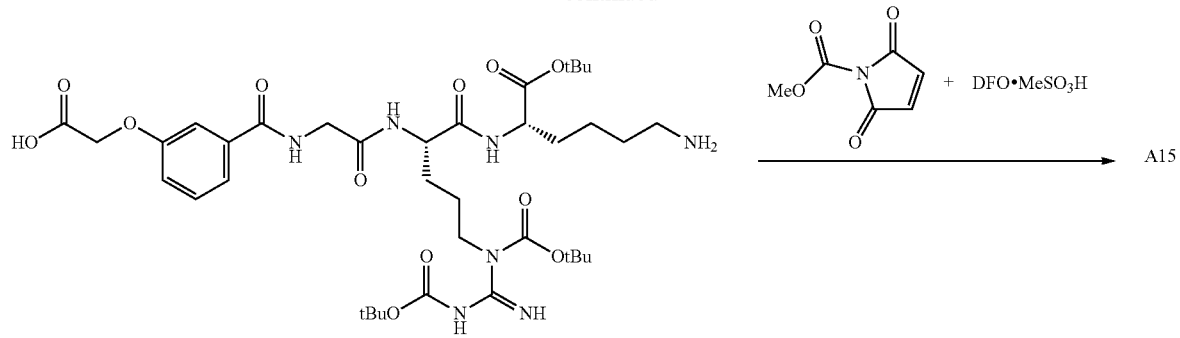
[Chemical Formula 32]
Production Example No. A16
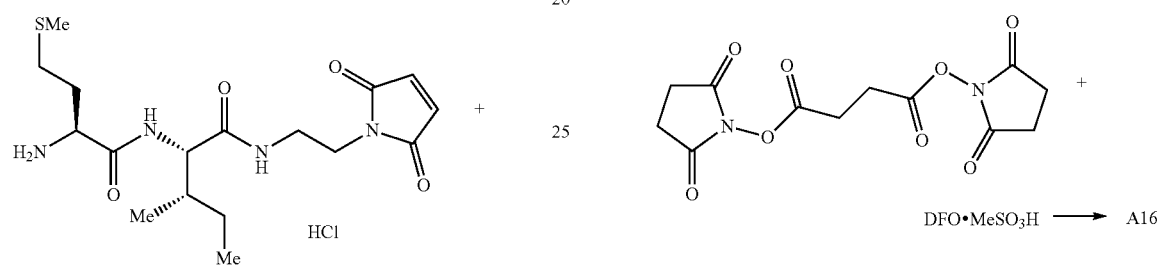
[Chemical Formula 33]
Production Example No. A17
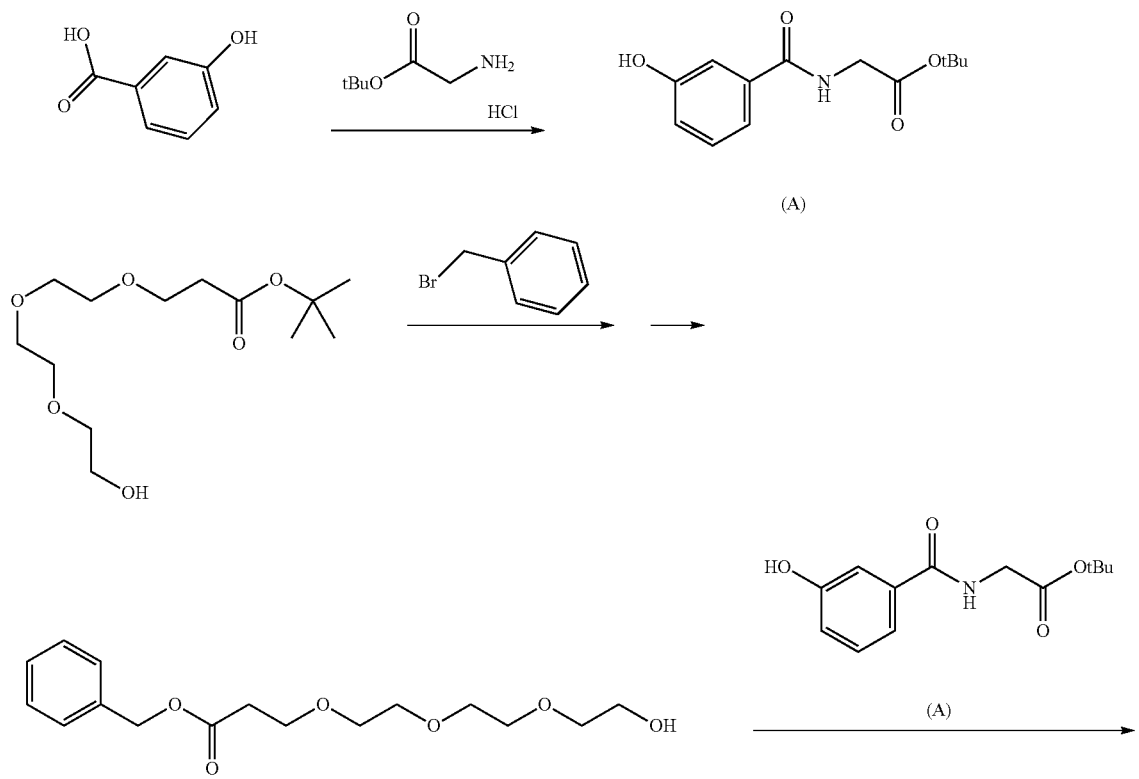

-continued
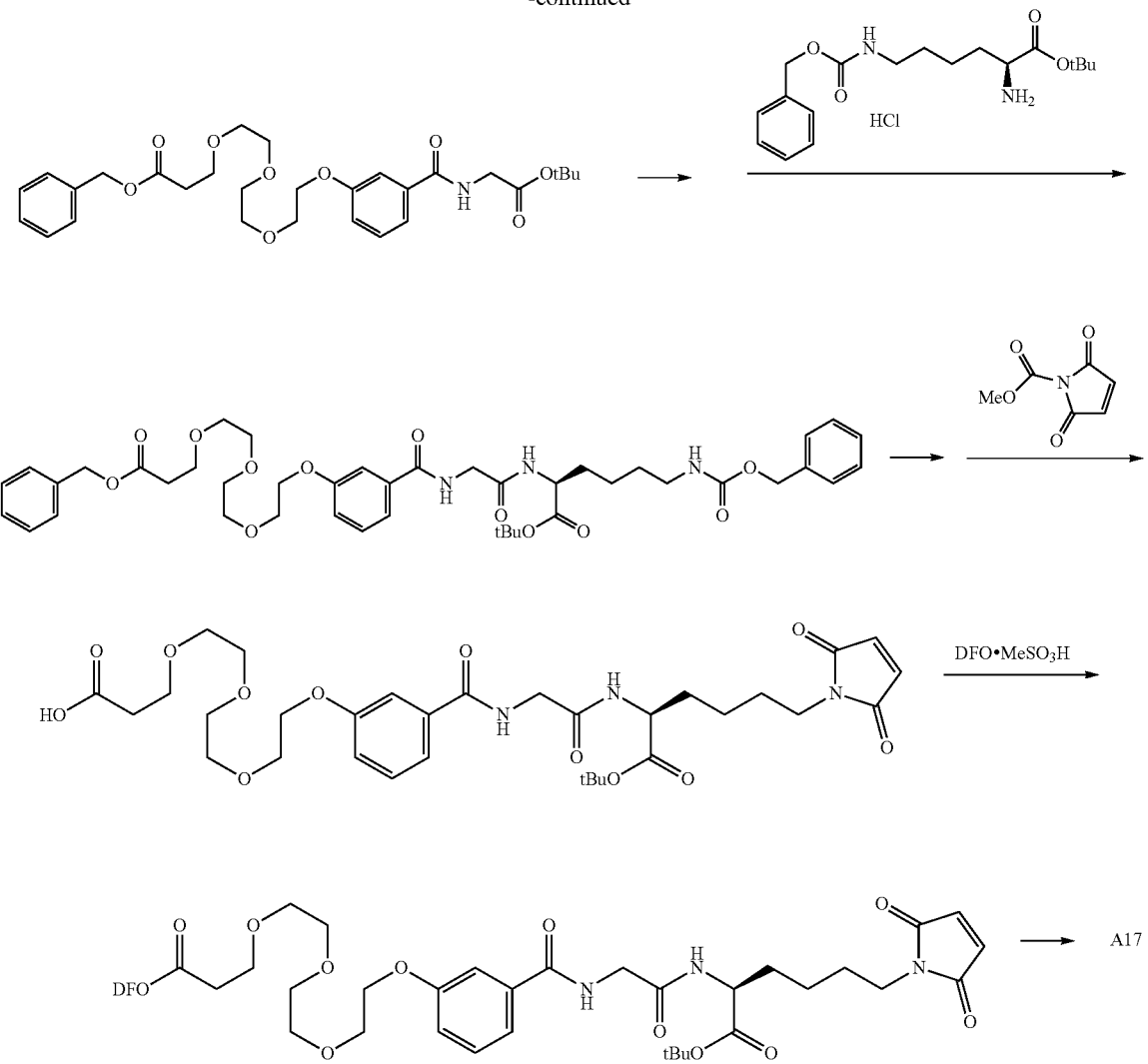
[Chemical Formula 34]
Production Example No. A18
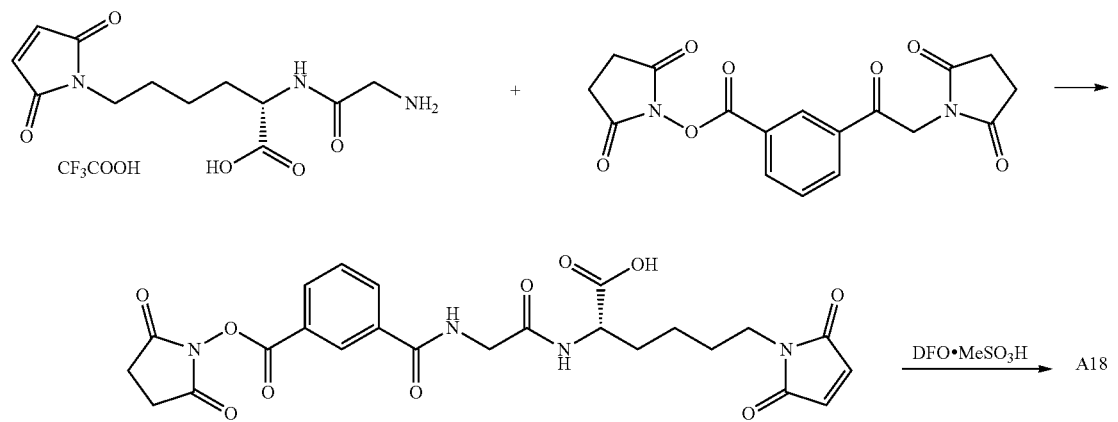

[Chemical Formula 35]

Production Example No. A19

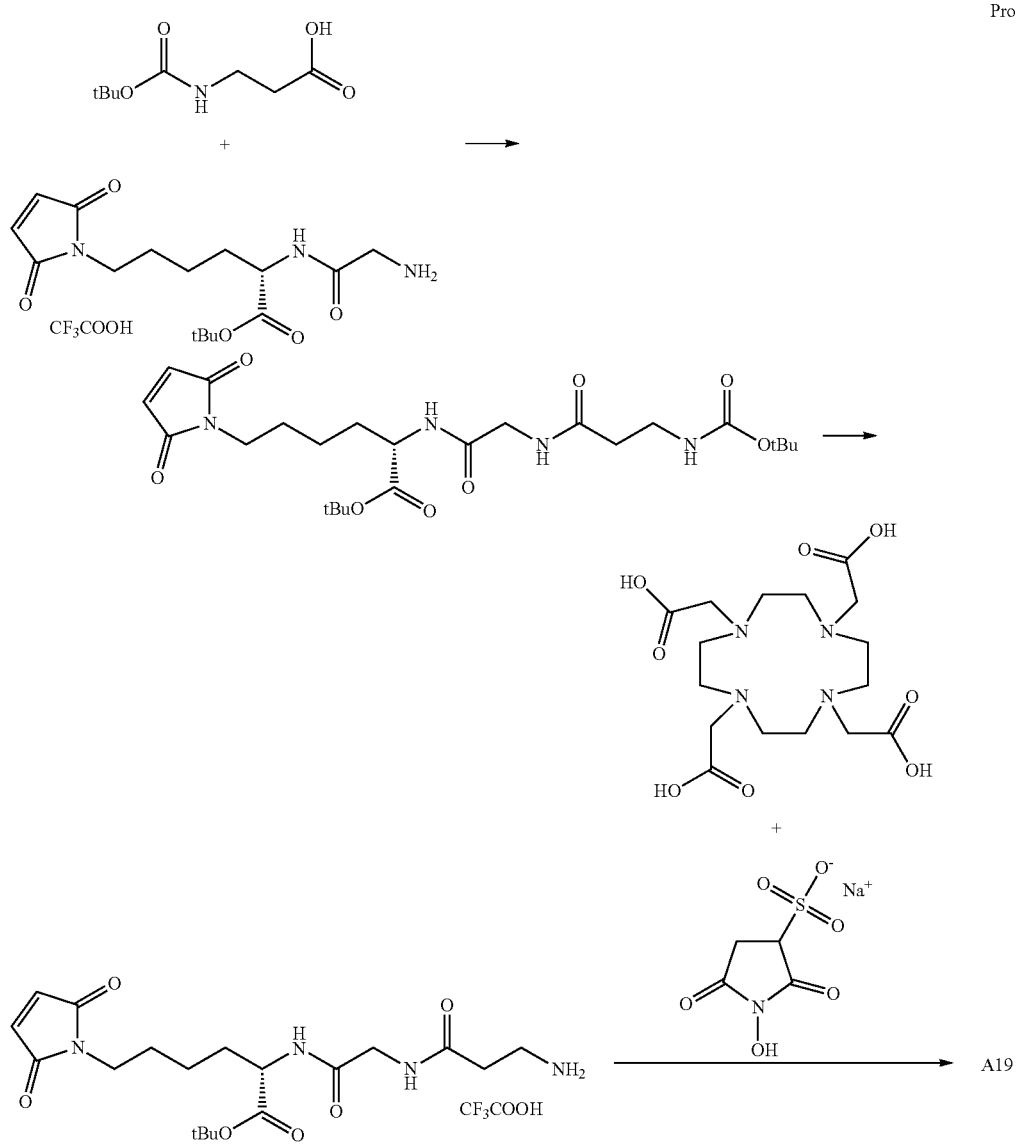

Conjugate Nos. B1 to B19 of Table 2 can be synthesized by the same approach as in the step (iv) of Example 3-1 or the step (iii) of Example 3-3 or Example 3-5 described above using the corresponding compounds of Production Example Nos. A1 to A19. In the table, p represents a natural number of 1 to 25 (a certain embodiment is a natural number of 1 to 4), 1,3-Ph represents 1,3-phenylene, and 1,4-Ph represents 1,4-phenylene.

TABLE 2

| No. | Conjugate |
|---|---|
| B1 | [DFO-C(=O)—CH$_2$O-(1,3-Ph)—C(=O)-Met-Ile-NH—(CH$_2$)$_2$-Z$_1$]$_p$-Fab |
| B2 | [DFO-C(=O)—CH$_2$O-(1,3-Ph)—C(=O)-Gly-Phe-Lys-Z$_2$]$_p$-Fab |
| B3 | [DFO-C(=O)—CH$_2$O-(1,3-Ph)—C(=O)-Met-Val-Lys-Z$_2$]$_p$-Fab |
| B4 | [DFO-C(=O)-(1,4-Ph)—C(=O)-Gly-Lys-Z$_2$]$_p$-Fab |
| B5 | [DFO-C(=O)—CH$_2$O-(1,3-Ph)—C(=O)-Gly-Lys—C(=S)—NH-(1,4-Ph)—NH—C(=S)]$_p$-Fab |

TABLE 2-continued

| No. | Conjugate |
|---|---|
| B6 | [DFO-C(=O)—CH$_2$O-(1,3-Ph)—C(=O)-Met-Ile-NH—(CH$_2$)$_2$—NH—C(=S)—NH-(1,4-Ph)—NH—C(=S)]$_p$-Fab |
| B7 | [DFO-C(=S)—NH-(1,4-Ph)—NH—C(=S)-Gly-Lys-Z$_2$]$_p$-Fab |
| B8 | [DFO-C(=O)-(1,3-Ph)—C(=O)-Met-Ile-NH—(CH$_2$)$_2$-Z$_1$]$_p$-Fab |
| B9 | [DFO-C(=O)-(1,4-Ph)—C(=O)-Met-Ile-NH—(CH$_2$)$_2$-Z$_1$]$_p$-Fab |
| B10 | [DFO-C(=O)—CH$_2$O-(1,3-Ph)—C(=O)-Gly-Tyr-CH$_2$—C(=O)—NH—(CH$_2$)$_2$-Z$_1$]$_p$-Fab |
| B11 | [DFO-C(=S)—NH-(1,4-Ph)—NH—C(=S)-Met-Ile-NH—(CH$_2$)$_2$-Z$_1$]$_p$-Fab |
| B12 | [DFO-C(=O)—(CH$_2$CH$_2$O)$_4$-(1,3-Ph)—C(=O)-Met-Ile-NH—(CH$_2$)$_2$-Z$_1$]$_p$-Fab |
| B13 | [DFO-C(=O)—(CH$_2$)$_2$—C(=O)-Gly-Lys-Z$_2$]$_p$-Fab |
| B14 | [DFO-C(=O)—CH$_2$O-(1,3-Ph)—C(=O)-Gly-Lys-Lys-Z$_2$]$_p$-Fab |
| B15 | [DFO-C(=O)—CH$_2$O-(1,3-Ph)—C(=O)-Gly-Arg-Lys-Z$_2$]$_p$-Fab |
| B16 | [DFO-C(=O)—(CH$_2$)$_2$—C(=O)-Met-Ile-NH—(CH$_2$)$_2$-Z$_1$]$_p$-Fab |
| B17 | [DFO-C(=O)—(CH$_2$CH$_2$O)$_4$-(1,3-Ph)—C(=O)-Gly-Lys-Z$_2$]$_p$-Fab |

TABLE 2-continued

| No. | Conjugate |
|---|---|
| B18 | [DFO-C(=O)-(1,3-Ph)—C(=O)-Gly-Lys-$Z_2$]$_p$-Fab |
| B19 | [DOTA-NH—(CH$_2$)$_2$—C(=O)-Gly-Lys-$Z_2$]$_p$-Fab |

Example 4: Binding Activity Evaluation of Fab Fragment

Binding activity against human cancer-specific MUC1 was compared as to P10-1 Fab and P10-2 Fab expressed by the method of Example 1 with a chimeric 1B2 antibody Fab fragment (hereinafter, referred to as 1B2 Fab; prepared by linking a human IgG1 $C_H1$ domain and a κ chain $C_L$ domain to the $V_H$ domain and the $V_L$ domain (their sequence information was quoted from PTL 1), respectively, of the 1B2 antibody (PTL 1); for the convenience of linking of the $C_H1$ domain and the $C_L$ domain, an alanine residue at position 113 based on the EU index (Kabat et al.) in the $V_H$ domain was substituted by a serine residue, and an alanine residue at position 109 based on the EU index (Kabat et al.) in the $V_L$ domain was substituted by a threonine residue) by Cell ELISA. Specifically, breast cancer cell line T-47D cells (purchasable from ATCC; HTB-133) expressing human cancer-specific MUC1 were inoculated at $0.75 \times 10^4$ cells per well to a 96-well ELISA plate coated with collagen I, and cultured overnight. Then, the cells were fixed in formalin, and P10-1 Fab, P10-2 Fab or 1B2 Fab described above was reacted therewith. Then, a horseradish peroxidase (HRP)-labeled goat anti-human Igκ antibody (Southern Biotechnology Associates, Inc.) was reacted as a secondary antibody. ECL Prime Western Blotting Detection Reagent (GE Healthcare Japan Corp.) was added thereto for luminescence, and the degree of the luminescence was examined. As a result, as shown in FIG. 1, P10-1 Fab and P10-2 Fab were confirmed to have approximately 10 or more times the binding activity against human cancer-specific MUC1 compared to 1B2 Fab.

Example 5: Binding Activity Evaluation of Anti-Human MUC1 Antibody Fab Fragment Conjugate ELISA was conducted in order to evaluate the binding activity of each anti-human MUC1 antibody Fab fragment conjugate prepared by the method of Example 3 against human cancer-specific MUC1.

Sample No. 5: [DOTA-Gly-Lys-$Z_2$]$_p$-Fab
Sample No. 6: [DOTA-NH—CH$_2$-(1,3-phenylene)-C(=O)-Gly-Lys-$Z_2$]$_p$-Fab
Sample No. 7: [DOTA-Met-Ile-NH—(CH$_2$)$_2$—$Z_1$]p-Fab
Sample No. 3: [DOTA-CH$_2$-(1,4-phenylene)-NH—C(=S)]$_p$-Fab Human cancer-specific MUC1 peptide (PTL 1) was immobilized at 0.5 μmol/L per well onto a 384-well ELISA plate. The resultant was reacted with each anti-human MUC1 antibody Fab fragment conjugate described above (sample No. 5, 6, 7, or 3) and then reacted with a horseradish peroxidase-labeled goat anti-human Igκ antibody (Southern Biotechnology Associates, Inc.) as a secondary antibody. ECL Prime Western Blotting Detection Reagent (GE Healthcare Japan Corp.) was added thereto for luminescence, and the degree of the luminescence was examined. The results are shown in Table 3. The conjugates of sample Nos. 5, 6, 7 and 3 were confirmed to have binding activity against human cancer-specific MUC1 peptide equivalent to that of P10-2 Fab.

TABLE 3

| Sample | 5 | 6 | 7 | 3 | P10-2 Fab |
|---|---|---|---|---|---|
| EC50 (nmol/L) | 0.31 | 0.30 | 0.31 | 0.49 | 0.23 |

Likewise, binding activity evaluation was also conducted as to the anti-human MUC1 antibody Fab fragment conjugates given below. The results are shown in Tables 4 and 5.

Sample No. 4: [DOTA]$_p$-Fab
Sample No. 1: [DFO—C(=O)-(1,3-phenylene)-C(=O)-Gly-Lys-$Z_2$]$_p$-Fab
Sample No. 2: [DFO—C(=O)—CH$_2$O-(1,3-phenylene)-C(=O)-Gly-Lys-$Z_2$]$_p$-Fab

TABLE 4

| Sample | 4 | P10-2 Fab |
|---|---|---|
| EC50 (nmol/L) | 0.35 | 0.17 |

TABLE 5

| Sample | 1 | 2 | P10-2 Fab |
|---|---|---|---|
| EC50 (nmol/L) | 0.29 | 0.30 | 0.16 |

As a result, the conjugates of sample Nos. 4, 1, and 2 were also confirmed to have binding activity against human cancer-specific MUC1 peptide equivalent to that of P10-2 Fab.

INDUSTRIAL APPLICABILITY

The conjugate of the present invention has excellent binding activity against human cancer-specific MUC1 and is therefore expected to be useful in the diagnosis and/or treatment of cancers.

SEQUENCE LISTING FREE TEXT

SEQ ID NO: 1: Nucleotide sequence of DNA encoding a P10-1 Fab heavy chain fragment
SEQ ID NO: 2: Amino acid sequence of the P10-1 Fab heavy chain fragment
SEQ ID NO: 3: Nucleotide sequence of DNA encoding a P10-2 Fab heavy chain fragment
SEQ ID NO: 4: Amino acid sequence of the P10-2 Fab heavy chain fragment
SEQ ID NO: 5: Nucleotide sequence of DNA encoding an antibody light chain
SEQ ID NO: 6: Amino acid sequence of the antibody light chain
SEQ ID NO: 7: Nucleotide sequence of DNA encoding a P10-1 Fab heavy chain variable region
SEQ ID NO: 8: Amino acid sequence of the P10-1 Fab heavy chain variable region
SEQ ID NO: 9: Nucleotide sequence of DNA encoding a P10-2 Fab heavy chain variable region
SEQ ID NO: 10: Amino acid sequence of the P10-2 Fab heavy chain variable region
SEQ ID NO: 11: Nucleotide sequence of DNA encoding an antibody light chain variable region SEQ ID NO: 12: Amino acid sequence of the antibody light chain variable region
SEQ ID NO: 13: Heavy chain signal sequence
SEQ ID NO: 14: Light chain signal sequence
SEQ ID NO: 15: Tandem repeat sequence of the extracellular domain of MUC1

The invention claimed is:

1. A conjugate represented by the following formula (I):

(Y—S$_1$—X)$_p$-Fab     (I), wherein

Fab is an anti-human MUC1 antibody Fab fragment selected from the group consisting of the following (a) and (b):
(a) an anti-human MUC1 antibody Fab fragment comprising a heavy chain fragment comprising a heavy chain variable region consisting of the amino acid sequence represented by SEQ ID NO: 8 or SEQ ID NO: 10 and a light chain comprising a light chain variable region consisting of the amino acid sequence represented by SEQ ID NO: 12, and
(b) an anti-human MUC1 antibody Fab fragment comprising a heavy chain fragment comprising a heavy chain variable region derived from a heavy chain variable region consisting of the amino acid sequence represented by SEQ ID NO: 8 or SEQ ID NO: 10 by the modification of glutamine at amino acid position 1 of SEQ ID NO: 8 or SEQ ID NO: 10 into pyroglutamic acid, and a light chain comprising a light chain variable region consisting of the amino acid sequence represented by SEQ ID NO: 12;

X is a peptide linker comprising the amino acid sequence selected from the group consisting of Gly-Lys and Met-Ile, wherein the peptide linker optionally comprises a spacer suitable for binding to the anti-human MUC1 antibody Fab fragment, wherein the spacer is a group that forms an organochemical bond between the peptide linker and the nitrogen atom of an amino group or a disulfide bond-derived thiol group of the anti-human MUC1 antibody Fab fragment;

S$_1$ is a spacer or a bond;

Y is deferoxamine (DFO) or 1,4,7,10-tetraazacyclodo-decane-1,4,7,10-tetraacetic acid (DOTA); and p is a natural number of 1 to 25.

2. The conjugate according to claim 1, wherein Fab is selected from the group consisting of the following (a) and (b):
(a) an anti-human MUC1 antibody Fab fragment comprising a heavy chain fragment consisting of the amino acid sequence represented by SEQ ID NO: 2 or SEQ ID NO: 4 and a light chain consisting of the amino acid sequence represented by SEQ ID NO: 6; and
(b) an anti-human MUC1 antibody Fab fragment comprising a heavy chain fragment derived from a heavy chain fragment consisting of the amino acid sequence represented by SEQ ID NO: 2 or SEQ ID NO: 4 by the modification of glutamine at amino acid position 1 of SEQ ID NO: 2 or SEQ ID NO: 4 into pyroglutamic acid, and a light chain consisting of the amino acid sequence represented by SEQ ID NO: 6.

3. The conjugate according to claim 1, wherein Fab is selected from the group consisting of the following (a) and (b):

(a) an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12; and
(b) an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12.

4. The conjugate according to claim 2, wherein Fab is selected from the group consisting of the following (a) and (b):
(a) an anti-human MUC1 antibody Fab fragment comprising a heavy chain fragment consisting of the amino acid sequence represented by SEQ ID NO: 4 and a light chain consisting of the amino acid sequence represented by SEQ ID NO: 6; and
(b) an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

5. The conjugate according to claim 4, wherein Fab is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6.

6. The conjugate according to claim 4, wherein Fab is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

7. The conjugate according to claim 1, wherein S$_1$ is —C(=O)—CH$_2$O-(1,3-phenylene)-C(=O)—, —C(=S)—NH—(1,4-phenylene)-NH—C(=S)—, —NH—CH$_2$-(1,3-phenylene)-C(=O)—, —C(=O)—(CH$_2$CH$_2$O) 4-(1,3-phenylene)-C(=O)—, —CH$_2$-(1,4-phenylene)-NH—C(=S)—, —NH—(CH$_2$) 2-C(=O)—, —C(=O)-(1,4-phenylene)-C(=O)—, —C(=O)-(1,3-phenylene)-C(=O)—, —C(=O)—(CH$_2$) 2-C(=O)—, or a bond, and X is a peptide linker selected from the group consisting of the following (1), (2), (8) and (9):
(1)-Met-Ile-NH—(CH$_2$)$_2$—Z$_1$—,
(2)-Gly-Lys-Z$_2$—, (8) -Gly-Lys-C(=S)—NH—(1,4-phenylene)-NH—C(=S)—, and
(9) -Met-Ile-NH—(CH$_2$)$_2$—NH—C(=S)—NH—(1,4-phenylene)-NH—C(=S)—, wherein Met represents methionine, Ile represents isoleucine, Gly represents glycine, Lys represents lysine, Z represents a group represented by the following formula (II), -Lys-Z$_2$-represents a group represented by the following formula (III),

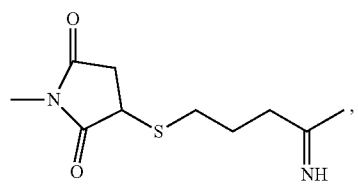
(II)

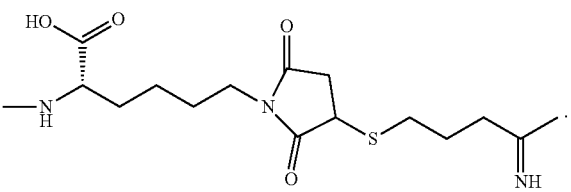
(III)

8. The conjugate according to claim 1, wherein Y is DFO.

9. The conjugate according to claim 1, wherein Y is DOTA.

10. The conjugate according to claim 8, wherein (Y—S$_1$—X)$_p$-Fab is selected from the group consisting of

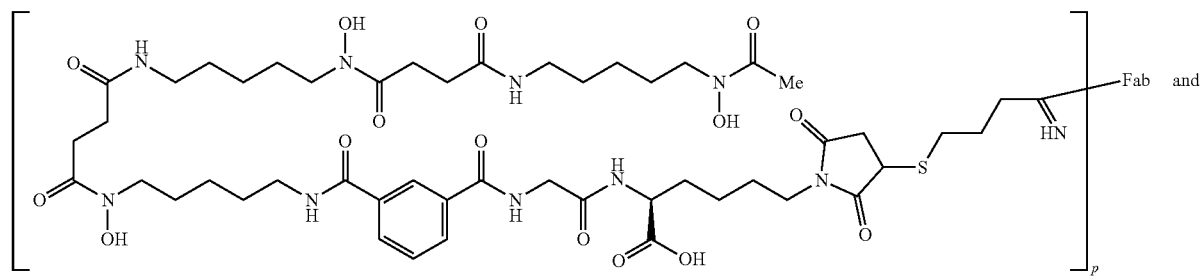

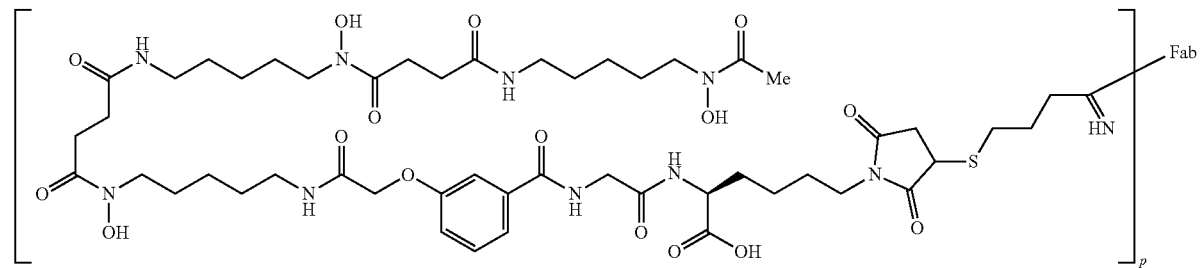

and the nitrogen atom of an amino group contained in Fab is bonded to the carbon atom of the terminal C(=NH) group of X.

11. The conjugate according to claim 9, wherein (Y—S$_1$—X)$_p$-Fab is selected from the group consisting of

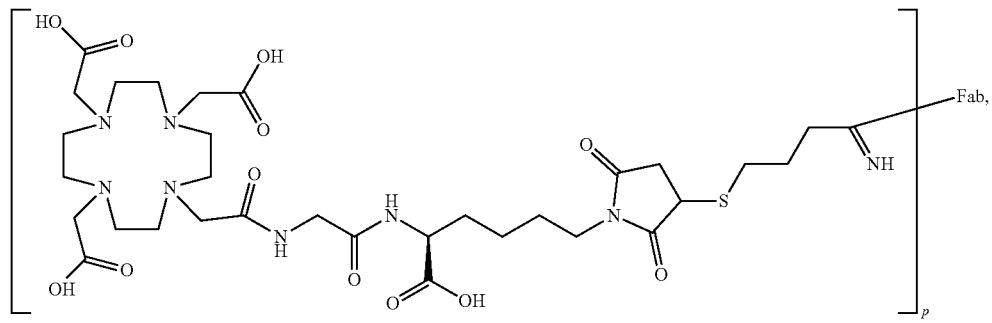

-continued

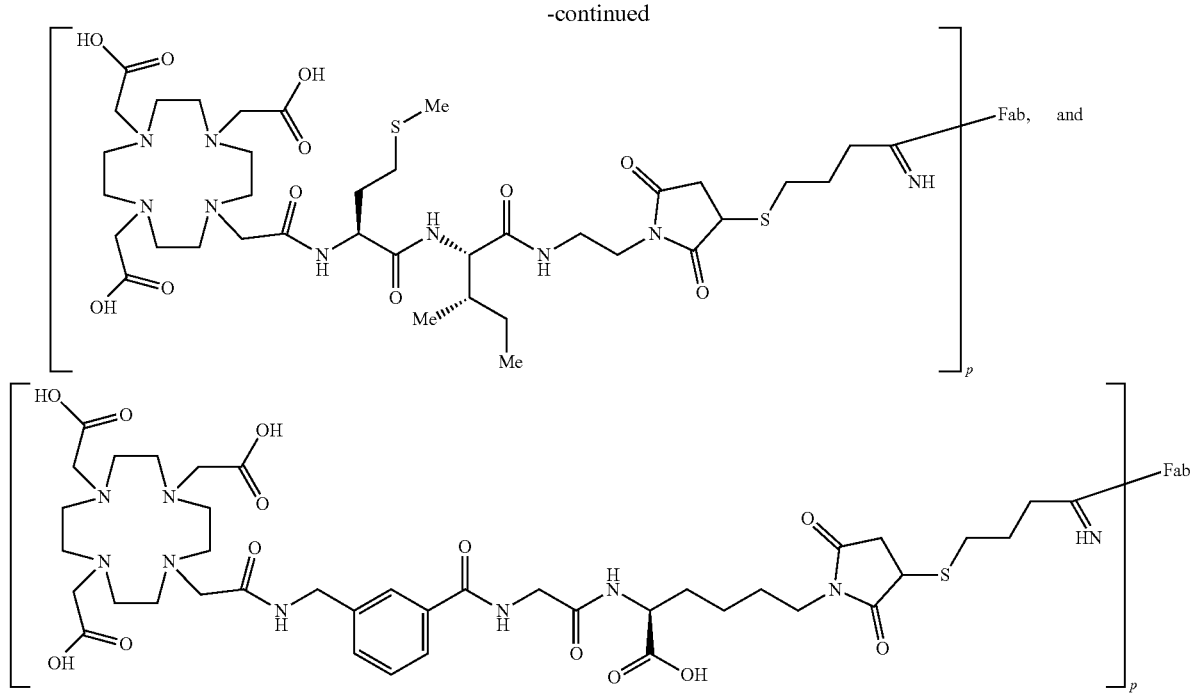

and the nitrogen atom of an amino group contained in Fab is bonded to the carbon atom of the terminal C(=NH) group of X.

12. The conjugate according to claim 1, wherein p is a natural number of 1 to 4.

13. The conjugate according to claim 1, further comprising a metal.

14. The conjugate according to claim 13, wherein the metal is a metal radioisotope.

15. The conjugate according to claim 14, wherein the metal is $^{89}$Zr.

16. The conjugate according to claim 14 which is a PET tracer.

17. A composition for diagnosis comprising one or more conjugate according to claim 13, and a pharmaceutically acceptable carrier.

18. The composition for diagnosis according to claim 17 which is an early diagnostic drug or a staging drug.

19. The composition for diagnosis according to claim 17 which is used in the diagnosis of a cancer expressing human MUC1.

20. The composition for diagnosis according to claim 19, wherein the cancer is breast cancer, lung cancer, colorectal cancer, bladder cancer, skin cancer, thyroid gland cancer, stomach cancer, pancreatic cancer, kidney cancer, ovary cancer, or uterine cervical cancer.

21. A pharmaceutical composition comprising one or more conjugate according to claim 13, and a pharmaceutically acceptable carrier.

22. The pharmaceutical composition according to claim 21 which is a pharmaceutical composition for treating a cancer expressing human MUC1.

23. The pharmaceutical composition according to claim 22, wherein the cancer is breast cancer, lung cancer, colorectal cancer, bladder cancer, skin cancer, thyroid gland cancer, stomach cancer, pancreatic cancer, kidney cancer, ovary cancer, or uterine cervical cancer.

24. A method for diagnosing a cancer, comprising administering a diagnostically effective amount of the conjugate according to claim 13 to a subject in need thereof.

25. A method for treating a cancer, comprising administering a therapeutically effective amount of the conjugate according to claim 13 to a subject in need thereof.

* * * * *

```
                       SEQUENCE LISTING

<160> NUMBER OF SEQ ID NOS: 15

<210> SEQ ID NO 1
<211> LENGTH: 669
<212> TYPE: DNA
<213> ORGANISM: Artificial Sequence
<220> FEATURE:
<223> OTHER INFORMATION: DNA encoding P10-1 Fab heavy chain fragment

<400> SEQUENCE: 1
caggtgcagc tggtgcagtc tggcgccgaa gtgaagaaac aggcgccag cgtgaaggtg      60 tcctgcaagg ccagcggcta caccttcacc aactacggcc tgagctgggt gcgccaggct    120
cctggacagg gactggaatg gatgggcgag aaccaccctg gcagcggcat catctaccac    180
aacgagaagt tccggggcag agtgaccctg accgccgacc ggagcaccag caccgcctac    240
atggaactga gcagcctgcg gagcgaggac accgccgtgt actactgtgc cagaagcagc    300
ggcaccagag gctttgccta ttggggacag ggcaccctcg tgaccgtgtc ctcagcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctta gtagcgtggt gaccgtgccc tccagcagct gggcaccca gacctacatc    600 tgcaacgtga atcacaagcc cagcaacacc aaggtggaca agaaagttga gcccaaatct    660
tgtgactga                                                            669

<210> SEQ ID NO 2
<211> LENGTH: 222
<212> TYPE: PRT
<213> ORGANISM: Artificial Sequence
<220> FEATURE:
<223> OTHER INFORMATION: P10-1 Fab heavy chain fragment

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205

Asn Thr Lys Val Asp Lys Lys Val Glu Pro Lys Ser Cys Asp
                    210                 215                 220

<210> SEQ ID NO 3
<211> LENGTH: 669
<212> TYPE: DNA
<213> ORGANISM: Artificial Sequence
<220> FEATURE:
<223> OTHER INFORMATION: DNA encoding P10-2 Fab heavy chain fragment

<400> SEQUENCE: 3
caggtgcagc tggtgcagtc tggcgccgaa gtgaagaaac aggcgccag cgtgaaggtg      60 tcctgcaagg ccagcggcta caccttcacc aactacggcc tgagctgggt gcgccaggct    120
cctggacagg gactggaatg gatgggcgag aaccaccctg gcagcggcat catctaccac    180
aacgagaagt tccggggcag agtgaccctg accgccgacc ggagcaccag caccgcctac    240
atggaactga gcagcctgcg gagcgaggac accgccgtgt actactgtgc cagaagcagc    300
ggcaccagag gctttgacta ttggggacag ggcaccctcg tgaccgtgtc ctcagcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccggctg tcctacagtc ctcaggactc    540 tactcccta gtagcgtggt gaccgtgccc tccagcagct gggcaccca gacctacatc    600 tgcaacgtga atcacaagcc cagcaacacc aaggtggaca agaaagttga gcccaaatct    660
tgtgactga                                                            669

<210> SEQ ID NO 4
<211> LENGTH: 222
<212> TYPE: PRT
<213> ORGANISM: Artificial Sequence
<220> FEATURE:
<223> OTHER INFORMATION: P10-2 Fab heavy chain fragment

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Leu Ser Trp Val Arg Gln Ala Pro Gly Gln Gly Leu Glu Trp Met
            35                  40                  45

Gly Glu Asn His Pro Gly Ser Gly Ile Ile Tyr His Asn Glu Lys Phe
        50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Asp Tyr Trp Gly Gln Gly Thr
                100                 105                 110
```

```
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp
210                 215                 220
```

<210> SEQ ID NO 5
<211> LENGTH: 660
<212> TYPE: DNA
<213> ORGANISM: Artificial Sequence
<220> FEATURE:
<223> OTHER INFORMATION: DNA encoding antibody light chain

<400> SEQUENCE: 5

```
gacgtcgtga tgacccagac ccctctgagc ctgagcgtga cacctggaca gcctgccagc      60
atcagctgca gatccagcca gagcatcgtg cacagcaacg gcaacaccta cctggaatgg     120
tatctgcaga agcccggcca gagcccccag ctgctgatct acagggtgtc caaccggttc     180
agcggcgtgc ccgacagatt ttctggcagc ggctccggca ccgacttcac cctgaagatc     240
tcccgggtgg aagccgagga cgtgggcgtg tactactgtt tcaaggcag ccacggcccc      300
tggaccttg gccagggaac aaagctggaa atcaagcgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctg     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660
```

<210> SEQ ID NO 6
<211> LENGTH: 219
<212> TYPE: PRT
<213> ORGANISM: Artificial Sequence
<220> FEATURE:
<223> OTHER INFORMATION: Antibody light chain

<400> SEQUENCE: 6

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
```

```
            85                  90                  95
Ser His Gly Pro Trp Thr Phe Gly Gln Gly Thr Lys Leu Glu Ile Lys
        100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 7
<211> LENGTH: 354
<212> TYPE: DNA
<213> ORGANISM: Artificial Sequence
<220> FEATURE:
<223> OTHER INFORMATION: DNA encoding P10-1 Fab heavy chain variable
      region

<400> SEQUENCE: 7
caggtgcagc tggtgcagtc tggcgccgaa gtgaagaaac aggcgccag cgtgaaggtg      60 tcctgcaagg ccagcggcta ccttcacc aactacggcc tgagctgggt gcgccaggct      120
cctggacagg gactggaatg gatgggcgag aaccaccctg gcagcggcat catctaccac    180
aacgagaagt tccggggcag agtgaccctg accgccgacc ggagcaccag caccgcctac    240
atggaactga gcagcctgcg gagcgaggac accgccgtgt actactgtgc cagaagcagc    300
ggcaccagag gctttgccta ttggggacag ggcaccctcg tgaccgtgtc ctca           354

<210> SEQ ID NO 8
<211> LENGTH: 118
<212> TYPE: PRT
<213> ORGANISM: Artificial Sequence
<220> FEATURE:
<223> OTHER INFORMATION: P10-1 Fab heavy chain variable region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Leu Ser Trp Val Arg Gln Ala Pro Gly Gln Gly Leu Glu Trp Met
            35                  40                  45

Gly Glu Asn His Pro Gly Ser Gly Ile Ile Tyr His Asn Glu Lys Phe
        50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Ala Tyr Trp Gly Gln Gly Thr
            100                 105                 110
```

```
Leu Val Thr Val Ser Ser
        115

<210> SEQ ID NO 9
<211> LENGTH: 354
<212> TYPE: DNA
<213> ORGANISM: Artificial Sequence
<220> FEATURE:
<223> OTHER INFORMATION: DNA encoding P10-2 Fab heavy chain variable
      region

<400> SEQUENCE: 9
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccaccctg gcagcggcat catctaccac     180
aacgagaagt tccggggcag agtgaccctg accgccgacc ggagcaccag caccgcctac     240
atggaactga gcagcctgcg gagcgaggac accgccgtgt actactgtgc agaagcagc      300 ggcaccagag gctttgacta ttggggacag ggcaccctcg tgaccgtgtc ctca           354

<210> SEQ ID NO 10
<211> LENGTH: 118
<212> TYPE: PRT
<213> ORGANISM: Artificial Sequence
<220> FEATURE:
<223> OTHER INFORMATION: P10-2 Fab heavy chain variable region

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Asp Tyr Trp Gly Gln Gly Thr
            100                 105                 110

Leu Val Thr Val Ser Ser
        115

<210> SEQ ID NO 11
<211> LENGTH: 339
<212> TYPE: DNA
<213> ORGANISM: Artificial Sequence
<220> FEATURE:
<223> OTHER INFORMATION: DNA encoding antibody light chain variable
      region

<400> SEQUENCE: 11
gacgtcgtga tgacccagac ccctctgagc ctgagcgtga cacctggaca gcctgccagc      60
atcagctgca gatccagcca gagcatcgtg cacagcaacg gcaacaccta cctggaatgg     120
tatctgcaga agcccggcca gagcccccag ctgctgatct acagggtgtc caaccggttc     180
agcggcgtgc ccgacagatt ttctggcagc ggctccggca ccgacttcac cctgaagatc     240
```

```
tcccgggtgg aagccgagga cgtgggcgtg tactactgtt ttcaaggcag ccacggcccc    300
tggacctttg gccagggaac aaagctggaa atcaagcgt                            339
```

```
<210> SEQ ID NO 12
<211> LENGTH: 113
<212> TYPE: PRT
<213> ORGANISM: Artificial Sequence
<220> FEATURE:
<223> OTHER INFORMATION: Antibody light chain variable region

<400> SEQUENCE: 12
```

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Gly Pro Trp Thr Phe Gly Gln Gly Thr Lys Leu Glu Ile Lys
            100                 105                 110

Arg

```
<210> SEQ ID NO 13
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 13
```

Met Glu Trp Ser Trp Val Phe Leu Phe Phe Leu Ser Val Thr Thr Gly
1               5                   10                  15

Val His Ser

```
<210> SEQ ID NO 14
<211> LENGTH: 20
<212> TYPE: PRT
<213> ORGANISM: Artificial Sequence
<220> FEATURE:
<223> OTHER INFORMATION: Light chain signal sequence

<400> SEQUENCE: 14
```

Met Ser Val Pro Thr Gln Val Leu Gly Leu Leu Leu Leu Trp Leu Thr
1               5                   10                  15

Asp Ala Arg Cys
            20

```
<210> SEQ ID NO 15
<211> LENGTH: 20
<212> TYPE: PRT
<213> ORGANISM: Artificial Sequence
<220> FEATURE:
<223> OTHER INFORMATION: Tandem repeat sequence of an extracellular
      domain of MUC1

<400> SEQUENCE: 15
```

```
His Gly Val Thr Ser Ala Pro Asp Thr Arg Pro Ala Pro Gly Ser Thr
1               5                   10                  15
Ala Pro Pro Ala
            20
```